(12) United States Patent
Yourgenlow et al.

(10) Patent No.: US 11,565,082 B2
(45) Date of Patent: Jan. 31, 2023

(54) ENHANCED FLEXIBILITY NEUROVASCULAR CATHETER

(71) Applicant: Imperative Care, Inc., Campbell, CA (US)

(72) Inventors: Ashoor Shahbazi Yourgenlow, San Jose, CA (US); Lex Philip Jansen, Santa Cruz, CA (US); Brandon Yee, Oakland, CA (US); David Blum, San Jose, CA (US); Yi Yang, San Francisco, CA (US); Hao Doan, San Jose, CA (US)

(73) Assignee: Imperative Care, Inc., Campbell, CA (US)

( * ) Notice: Subject to any disclaimer, the term of this patent is extended or adjusted under 35 U.S.C. 154(b) by 0 days.

(21) Appl. No.: 17/475,202

(22) Filed: Sep. 14, 2021

(65) Prior Publication Data
US 2022/0001141 A1 Jan. 6, 2022

Related U.S. Application Data

(63) Continuation-in-part of application No. PCT/US2021/021382, filed on Mar. 8, 2021.
(Continued)

(51) Int. Cl.
*A61M 25/01* (2006.01)
*A61M 25/00* (2006.01)

(52) U.S. Cl.
CPC .... *A61M 25/0138* (2013.01); *A61M 25/0054* (2013.01); *A61M 25/0108* (2013.01); *A61M 2205/32* (2013.01)

(58) Field of Classification Search
CPC .......... A61M 2205/32; A61M 25/0012; A61M 25/0053; A61M 25/0054; A61M 25/0108;
(Continued)

(56) References Cited

U.S. PATENT DOCUMENTS 3,605,750 A 9/1971 Sheridan et al.
3,884,242 A 5/1975 Bazell et al.
(Continued)

FOREIGN PATENT DOCUMENTS

CN 110916768 3/2020
DE 8900059 5/1989
(Continued)

OTHER PUBLICATIONS

U.S. Appl. No. 16/863,723, filed Apr. 30, 2020, Thromboresistant Coatings for Aneurysm Treatment Devices.
(Continued)

*Primary Examiner* — Jason E Flick
(74) *Attorney, Agent, or Firm* — Knobbe, Martens, Olson & Bear, LLP

(57) ABSTRACT

An enhanced flexibility catheter is provided, such as for distal neurovascular access or aspiration. The catheter includes an elongate flexible body, having a proximal end, a distal end, and a side wall defining a central lumen. The side wall is formed from a plurality of adjacent tubular segments. At least one segment has a first end face inclined at a non normal angle to a longitudinal axis of the catheter. An adjacent segment has a second end face inclined at a complementary angle to form an inclined junction at the transition between the two segments. The transition serves to provide superior bending characteristics along the length of the catheter shaft.

24 Claims, 28 Drawing Sheets

Related U.S. Application Data

(60) Provisional application No. 62/987,546, filed on Mar. 10, 2020.

(58) Field of Classification Search
CPC .............. A61M 25/0138; A61M 25/00; A61M 25/0009; A61M 25/0043; A61M 25/005; A61M 25/01; A61M 25/0105; A61M 25/0133

See application file for complete search history.

(56) References Cited

U.S. PATENT DOCUMENTS

| | | |
|---|---|---|
| 3,890,976 A | 6/1975 | Bazell et al. |
| 3,965,901 A | 6/1976 | Penny et al. |
| 4,030,503 A | 6/1977 | Clark, III |
| 4,319,580 A | 3/1982 | Colley et al. |
| 4,611,594 A | 9/1986 | Grayhack et al. |
| 4,617,019 A | 10/1986 | Fecht et al. |
| 4,619,274 A | 10/1986 | Morrison |
| 4,628,168 A | 12/1986 | Nebergall et al. |
| 4,762,129 A | 8/1988 | Bonzel |
| 4,762,130 A | 8/1988 | Fogarty et al. |
| 4,767,399 A | 8/1988 | Bollish |
| 4,810,582 A | 3/1989 | Gould et al. |
| 4,844,064 A | 7/1989 | Thimsen et al. |
| 4,898,575 A | 2/1990 | Fischell et al. |
| 4,923,462 A | 5/1990 | Stevens |
| 5,011,488 A | 4/1991 | Ginsburg |
| 5,040,548 A | 8/1991 | Yock |
| 5,103,827 A | 4/1992 | Smith |
| 5,120,323 A | 6/1992 | Shockey et al. |
| 5,131,391 A | 7/1992 | Sakai et al. |
| 5,217,705 A | 6/1993 | Reno et al. |
| 5,226,909 A | 7/1993 | Evans et al. |
| 5,234,416 A | 8/1993 | Macaulay et al. |
| 5,243,997 A | 9/1993 | Uflacker et al. |
| 5,261,916 A | 11/1993 | Engelson et al. |
| 5,290,247 A | 3/1994 | Crittenden |
| 5,308,327 A | 5/1994 | Heaven et al. |
| 5,328,472 A | 7/1994 | Steinke et al. |
| 5,413,560 A | 5/1995 | Solar |
| 5,417,697 A | 5/1995 | Wilk et al. |
| 5,423,846 A | 6/1995 | Fischell |
| 5,439,445 A | 8/1995 | Kontos |
| 5,441,051 A | 8/1995 | Hileman et al. |
| 5,454,795 A | 10/1995 | Samson |
| 5,466,222 A | 11/1995 | Ressemann et al. |
| 5,474,563 A | 12/1995 | Myler et al. |
| 5,527,292 A | 6/1996 | Adams et al. |
| 5,549,119 A | 8/1996 | Solar |
| 5,569,178 A | 10/1996 | Henley |
| 5,569,277 A | 10/1996 | Evans et al. |
| 5,591,187 A | 1/1997 | Dekel |
| 5,638,818 A | 6/1997 | Diab et al. |
| 5,643,254 A | 7/1997 | Scheldrup et al. |
| 5,658,263 A | 8/1997 | Dang et al. |
| 5,662,622 A | 9/1997 | Gore et al. |
| 5,690,613 A | 11/1997 | Verbeek |
| 5,695,483 A | 12/1997 | Samson |
| 5,702,373 A | 12/1997 | Samson |
| 5,766,191 A | 6/1998 | Trerotola |
| 5,776,141 A | 7/1998 | Klein et al. |
| 5,827,242 A | 10/1998 | Follmer et al. |
| 5,843,103 A | 12/1998 | Wulfman |
| 5,873,882 A | 2/1999 | Straub et al. |
| 5,876,414 A | 3/1999 | Straub |
| 5,885,209 A | 3/1999 | Green |
| 5,891,114 A | 4/1999 | Chien et al. |
| 5,895,398 A | 4/1999 | Wensel et al. |
| 5,899,892 A | 5/1999 | Mortier et al. |
| 5,916,192 A | 6/1999 | Nita et al. |
| 5,935,112 A | 8/1999 | Stevens |
| 5,938,645 A | 8/1999 | Gordon |
| 5,951,539 A | 9/1999 | Nita |
| 6,007,530 A | 12/1999 | Dornhofer et al. |
| 6,056,837 A | 5/2000 | Lieber et al. |
| 6,059,745 A | 5/2000 | Gelbfish |
| 6,090,118 A | 7/2000 | McGuckin, Jr. |
| 6,159,230 A | 12/2000 | Samuels |
| 6,165,163 A | 12/2000 | Chien et al. |
| 6,165,199 A | 12/2000 | Barbut |
| 6,171,295 B1 | 1/2001 | Garabedian et al. |
| 6,179,859 B1 | 1/2001 | Bates et al. |
| 6,197,014 B1 | 3/2001 | Samson et al. |
| 6,206,852 B1 | 3/2001 | Lee |
| 6,217,557 B1 | 4/2001 | Hakansson et al. |
| 6,221,038 B1 | 4/2001 | Brisken |
| 6,228,046 B1 | 5/2001 | Brisken |
| 6,258,052 B1 | 7/2001 | Milo |
| 6,267,783 B1 | 7/2001 | Letendre et al. |
| 6,285,903 B1 | 9/2001 | Rosenthal et al. |
| 6,355,027 B1 | 3/2002 | Le et al. |
| 6,394,976 B1 | 5/2002 | Winston et al. |
| 6,400,971 B1 | 6/2002 | Firanov et al. |
| 6,451,036 B1 | 6/2002 | Heitzmann et al. |
| 6,451,005 B1 | 9/2002 | Saitou et al. |
| 6,458,139 B1 | 10/2002 | Palmer et al. |
| 6,468,219 B1 | 10/2002 | Njemanze |
| 6,482,217 B1 | 11/2002 | Pintor et al. |
| 6,511,492 B1 | 1/2003 | Rosenbluth et al. |
| 6,524,303 B1 | 2/2003 | Garibaldi et al. |
| 6,520,934 B1 | 3/2003 | Lee et al. |
| 6,533,751 B2 | 3/2003 | Cragg et al. |
| 6,554,820 B1 | 4/2003 | Wendlandt et al. |
| 6,554,827 B2 | 4/2003 | Chandrasekaran et al. |
| 6,558,377 B2 | 5/2003 | Lee et al. |
| 6,569,148 B2 | 5/2003 | Bagaoisan et al. |
| 6,579,246 B2 | 6/2003 | Jacobsen et al. |
| 6,582,440 B1 | 6/2003 | Brumbach |
| 6,591,472 B1 | 7/2003 | Noone et al. |
| 6,638,268 B2 | 10/2003 | Niazi |
| 6,666,874 B2 | 12/2003 | Heitzmann |
| 6,669,670 B1 | 12/2003 | Muni et al. |
| 6,719,717 B1 | 4/2004 | Johnson et al. |
| 6,776,770 B1 | 8/2004 | Trerotola |
| 6,805,692 B2 | 10/2004 | Muni et al. |
| 6,824,550 B1 | 11/2004 | Pintor et al. |
| 6,887,199 B2 | 5/2005 | Bridger et al. |
| 6,977,068 B1 | 12/2005 | Nair et al. |
| 7,004,954 B1 | 2/2006 | Voss et al. |
| 7,008,434 B2 | 3/2006 | Kurz et al. |
| 7,029,482 B1 | 4/2006 | Vargas et al. |
| 7,037,267 B1 | 5/2006 | Lipson et al. |
| 7,104,979 B2 | 9/2006 | Jansen et al. |
| 7,112,298 B2 | 9/2006 | Kampa et al. |
| 7,172,620 B2 | 2/2007 | Gilson |
| 7,175,653 B2 | 2/2007 | Gaber |
| 7,207,980 B2 | 4/2007 | Christian et al. |
| 7,223,274 B2 | 5/2007 | Vargas et al. |
| 7,229,461 B2 | 6/2007 | Chin et al. |
| 7,232,452 B2 | 6/2007 | Adams et al. |
| 7,235,088 B2 | 6/2007 | Pintor et al. |
| 7,306,585 B2 | 12/2007 | Ross |
| 7,309,334 B2 | 12/2007 | von Hoffmann |
| 7,335,216 B2 | 2/2008 | Bender et al. |
| 7,491,210 B2 | 2/2009 | Dubrul et al. |
| 7,507,229 B2 | 3/2009 | Hewitt et al. |
| 7,537,568 B2 | 5/2009 | Moehring |
| 7,558,622 B2 | 7/2009 | Tran |
| 7,601,138 B2 | 10/2009 | Goebel et al. |
| 7,678,100 B2 | 3/2010 | Chin et al. |
| 7,713,227 B2 | 5/2010 | Wholey et al. |
| 7,763,196 B2 | 7/2010 | Goebel et al. |
| 7,771,358 B2 | 8/2010 | Moehring et al. |
| 7,803,136 B2 | 9/2010 | Schatz |
| 7,837,692 B2 | 11/2010 | Mulholland et al. |
| 7,842,055 B2 | 11/2010 | Pintor et al. |
| 7,850,623 B2 | 12/2010 | Griffin et al. |
| 7,905,891 B2 | 3/2011 | Self |
| 7,931,659 B2 | 4/2011 | Bose et al. |
| 7,938,820 B2 | 5/2011 | Webster et al. |
| 7,988,646 B2 | 8/2011 | Taber |
| 8,021,351 B2 | 9/2011 | Boldenow et al. |

(56) References Cited

U.S. PATENT DOCUMENTS

| | | | |
|---|---|---|---|
| 8,048,032 | B2 | 11/2011 | Root et al. |
| 8,057,497 | B1 | 11/2011 | Raju et al. |
| 8,062,316 | B2 | 11/2011 | Patel et al. |
| 8,070,694 | B2 | 12/2011 | Galdonik et al. |
| 8,084,246 | B2 | 12/2011 | Hoon et al. |
| 8,114,106 | B2 | 2/2012 | Straub |
| 8,142,413 | B2 | 3/2012 | Root et al. |
| 8,114,032 | B2 | 4/2012 | Ferry et al. |
| 8,157,792 | B2 | 4/2012 | Dolliver et al. |
| 8,211,023 | B2 | 7/2012 | Swan et al. |
| 8,235,968 | B2 | 8/2012 | Tremaglio |
| 8,246,641 | B2 | 8/2012 | Osborne et al. |
| 8,292,850 | B2 | 10/2012 | Root et al. |
| 8,298,591 | B2 | 10/2012 | Srivastava et al. |
| 8,361,095 | B2 | 1/2013 | Osborne |
| 8,366,735 | B2 | 2/2013 | Bose et al. |
| 8,382,739 | B2 | 2/2013 | Walak et al. |
| 8,394,078 | B2 | 3/2013 | Torrance et al. |
| 8,403,912 | B2 | 3/2013 | McFerran et al. |
| 8,460,312 | B2 | 6/2013 | Bose et al. |
| 8,485,969 | B2 | 7/2013 | Grayzel et al. |
| 8,517,955 | B2 | 8/2013 | Keast et al. |
| 8,535,293 | B2 | 9/2013 | Faherty et al. |
| 8,568,432 | B2 | 10/2013 | Straub |
| 8,608,754 | B2 | 12/2013 | Wensel et al. |
| 8,609,426 | B2 | 12/2013 | Silver |
| 8,663,259 | B2 | 3/2014 | Levine et al. |
| 8,682,411 | B2 | 3/2014 | Kassab et al. |
| 8,684,963 | B2 | 4/2014 | Qiu et al. |
| 8,696,698 | B2 | 4/2014 | Chomas et al. |
| 8,702,680 | B2 | 4/2014 | Jimenez et al. |
| 8,725,249 | B2 | 5/2014 | Bar-Yoseph et al. |
| 8,734,374 | B2 | 5/2014 | Aklog et al. |
| 8,758,325 | B2 | 6/2014 | Webster et al. |
| 8,764,779 | B2 | 7/2014 | Levine et al. |
| 8,814,892 | B2 | 8/2014 | Galdonik et al. |
| 8,864,792 | B2 | 10/2014 | Eckhouse et al. |
| 8,876,854 | B2 | 11/2014 | Christiansen et al. |
| 8,900,257 | B2 | 12/2014 | Straub et al. |
| 8,932,320 | B1 | 1/2015 | Janardhan et al. |
| RE45,380 | E | 2/2015 | Root et al. |
| 8,968,383 | B1 | 3/2015 | Johnson et al. |
| 8,974,411 | B2 | 3/2015 | McKinnon |
| 8,992,506 | B2 | 3/2015 | Gulachenski |
| 8,996,095 | B2 | 3/2015 | Anderson et al. |
| 8,998,946 | B2 | 4/2015 | Morero |
| 9,014,786 | B2 | 4/2015 | Carmeli et al. |
| 9,017,309 | B2 | 4/2015 | Tanikawa et al. |
| 9,023,070 | B2 | 5/2015 | Levine et al. |
| 9,039,715 | B2 | 5/2015 | Diamant et al. |
| 9,079,000 | B2 | 7/2015 | Hanson et al. |
| 9,107,691 | B2 | 8/2015 | Fojtik |
| 9,119,625 | B2 | 9/2015 | Bachman et al. |
| 9,119,656 | B2 | 9/2015 | Bose et al. |
| 9,144,383 | B2 | 9/2015 | Zharov |
| 9,144,662 | B2 | 9/2015 | DiCaprio et al. |
| RE45,760 | E | 10/2015 | Root et al. |
| RE45,776 | E | 10/2015 | Root et al. |
| 9,199,064 | B2 | 12/2015 | Morero |
| 9,238,124 | B2 | 1/2016 | Grayzel et al. |
| 9,241,699 | B1 | 1/2016 | Kume et al. |
| 9,259,215 | B2 | 2/2016 | Chou et al. |
| 9,259,228 | B2 | 2/2016 | Cruise et al. |
| 9,265,512 | B2 | 2/2016 | Garrison et al. |
| 9,278,201 | B2 | 3/2016 | Rapaport et al. |
| 9,282,992 | B2 | 3/2016 | Levine et al. |
| 9,295,817 | B2 | 3/2016 | Chang |
| 9,314,268 | B2 | 4/2016 | Cahill |
| 9,345,856 | B2 | 5/2016 | Witte |
| 9,351,993 | B2 | 5/2016 | Cruise et al. |
| 9,370,639 | B2 | 6/2016 | Plassman et al. |
| 9,375,223 | B2 | 6/2016 | Wallace |
| 9,381,278 | B2 | 7/2016 | Constant et al. |
| 9,399,118 | B2 | 7/2016 | Kume et al. |
| RE46,116 | E | 8/2016 | Root et al. |
| 9,408,916 | B2 | 8/2016 | Cruise et al. |
| 9,414,819 | B2 | 8/2016 | Fitz et al. |
| 9,421,328 | B2 | 8/2016 | Brueckner et al. |
| 9,439,791 | B2 | 9/2016 | Vong et al. |
| 9,440,018 | B2 | 9/2016 | Levin et al. |
| 9,446,216 | B2 | 9/2016 | Olesky et al. |
| 9,451,884 | B2 | 9/2016 | Palovich et al. |
| 9,451,963 | B2 | 9/2016 | Cruise et al. |
| 9,463,006 | B2 | 10/2016 | Forde et al. |
| 9,480,813 | B2 | 11/2016 | Fukuoka et al. |
| 9,486,221 | B2 | 11/2016 | Cruise et al. |
| 9,492,637 | B2 | 11/2016 | Garrison et al. |
| 9,504,476 | B2 | 11/2016 | Gulachenski |
| 9,510,855 | B2 | 12/2016 | Rapaport et al. |
| 9,526,504 | B2 | 12/2016 | Chang |
| 9,526,505 | B2 | 12/2016 | Marks et al. |
| 9,532,792 | B2 | 1/2017 | Galdonik et al. |
| 9,533,344 | B2 | 1/2017 | Monetti et al. |
| 9,539,022 | B2 | 1/2017 | Bowman |
| 9,539,122 | B2 | 1/2017 | Burke et al. |
| 9,546,236 | B2 | 1/2017 | Cruise et al. |
| 9,561,121 | B2 | 2/2017 | Sudin et al. |
| 9,561,125 | B2 | 2/2017 | Bowman et al. |
| 9,561,345 | B2 | 2/2017 | Garrison et al. |
| 9,597,101 | B2 | 3/2017 | Galdonik et al. |
| 9,597,212 | B2 | 3/2017 | Thompson et al. |
| 9,615,832 | B2 | 3/2017 | Bose et al. |
| 9,622,753 | B2 | 4/2017 | Cox |
| 9,623,228 | B2 | 4/2017 | Ryan et al. |
| 9,655,633 | B2 | 5/2017 | Leynov et al. |
| 9,655,755 | B2 | 5/2017 | Chou et al. |
| 9,655,989 | B2 | 5/2017 | Cruise et al. |
| 9,662,118 | B2 | 5/2017 | Chang |
| 9,662,129 | B2 | 5/2017 | Galdonik et al. |
| 9,662,480 | B2 | 5/2017 | Kume et al. |
| 9,669,183 | B2 | 6/2017 | Chang |
| 9,669,191 | B2 | 6/2017 | Chou et al. |
| 9,681,882 | B2 | 6/2017 | Garrison et al. |
| 9,688,788 | B2 | 6/2017 | Plotkin et al. |
| 9,693,789 | B2 | 7/2017 | Garrison et al. |
| 9,693,852 | B2 | 7/2017 | Lam et al. |
| 9,707,380 | B2 | 7/2017 | Qiu et al. |
| 9,717,500 | B2 | 8/2017 | Tieu et al. |
| 9,724,103 | B2 | 8/2017 | Cruise et al. |
| 9,724,491 | B2 | 8/2017 | Solar et al. |
| 9,764,111 | B2 | 9/2017 | Gulachenski |
| 9,770,251 | B2 | 9/2017 | Bowman et al. |
| 9,775,730 | B1 | 10/2017 | Waltzman |
| 9,789,242 | B2 | 10/2017 | Criado et al. |
| 9,789,283 | B2 | 10/2017 | Richter et al. |
| 9,801,643 | B2 | 10/2017 | Hansen et al. |
| 9,803,043 | B2 | 10/2017 | Cruise et al. |
| 9,808,610 | B2 | 11/2017 | Li et al. |
| 9,820,761 | B2 | 11/2017 | Garrison et al. |
| 9,827,047 | B2 | 11/2017 | Fudaba et al. |
| 9,855,072 | B2 | 1/2018 | Moberg et al. |
| 9,861,783 | B2 | 1/2018 | Garrison et al. |
| 9,877,731 | B2 | 1/2018 | Cruise et al. |
| 9,883,885 | B2 | 2/2018 | Hendrick et al. |
| 9,907,880 | B2 | 3/2018 | Cruise et al. |
| 9,913,960 | B2 | 3/2018 | Blanchard et al. |
| 9,987,028 | B2 | 6/2018 | Lowinger et al. |
| 9,999,355 | B2 | 6/2018 | Kirenko |
| 10,010,698 | B2 | 7/2018 | Watanabe et al. |
| 10,028,854 | B2 | 7/2018 | Tatalovich et al. |
| 10,039,906 | B2 | 8/2018 | Kume et al. |
| 10,070,878 | B2 | 9/2018 | Ma |
| 10,086,169 | B2 | 10/2018 | Grayzel et al. |
| 10,105,154 | B1 | 10/2018 | Green |
| 10,179,224 | B2 | 1/2019 | Yang et al. |
| 10,183,145 | B2 | 1/2019 | Yang et al. |
| 10,183,146 | B2 | 1/2019 | Yang et al. |
| 10,183,147 | B2 | 1/2019 | Yang et al. |
| 10,207,077 | B2 | 2/2019 | Griggin et al. |
| 10,213,582 | B2 | 2/2019 | Garrison et al. |
| 10,226,277 | B2 | 3/2019 | Smith et al. |
| 10,238,833 | B2 | 3/2019 | Christian et al. |
| 10,258,452 | B2 | 4/2019 | Eckhouse et al. |
| 10,265,086 | B2 | 4/2019 | Vale |

(56) References Cited

U.S. PATENT DOCUMENTS

| | | |
|---|---|---|
| 10,271,864 B2 | 4/2019 | Greenhalgh et al. |
| 10,278,678 B2 | 5/2019 | Peliks |
| 10,278,816 B2 | 5/2019 | Miller |
| 10,327,790 B2 | 6/2019 | Garrison et al. |
| 10,335,186 B2 | 7/2019 | Rosenbluth et al. |
| 10,342,570 B2 | 7/2019 | Richter et al. |
| 10,383,691 B2 | 8/2019 | Hendrick et al. |
| 10,384,034 B2 | 8/2019 | Garrison et al. |
| 10,420,581 B2 | 9/2019 | Hehrlein |
| 10,441,745 B2 | 10/2019 | Yang et al. |
| 10,456,552 B2 | 10/2019 | Goyal |
| 10,471,233 B2 | 11/2019 | Garrison et al. |
| 10,524,814 B2 | 1/2020 | Chang et al. |
| 10,531,883 B1 | 1/2020 | Deville et al. |
| 10,537,706 B2 | 1/2020 | Kanemasa et al. |
| 10,569,049 B2 | 2/2020 | Garrison et al. |
| 10,610,668 B2 | 4/2020 | Burkholz et al. |
| 10,646,239 B2 | 5/2020 | Garrison et al. |
| 10,653,426 B2 | 5/2020 | Yang et al. |
| 10,653,434 B1 | 5/2020 | Yang et al. |
| 10,661,053 B2 | 5/2020 | Yang et al. |
| 10,668,192 B2 | 6/2020 | Raney et al. |
| 10,695,159 B2 | 6/2020 | Hauser |
| 10,716,880 B2 | 7/2020 | Culbert et al. |
| 10,716,915 B2 | 7/2020 | Ogle et al. |
| 10,722,251 B2 | 7/2020 | Garrison et al. |
| 10,722,253 B2 | 7/2020 | Deville et al. |
| 10,722,683 B2 | 7/2020 | Solar et al. |
| 10,743,893 B2 | 8/2020 | Garrison et al. |
| 10,786,270 B2 | 9/2020 | Yang et al. |
| 10,835,272 B2 | 11/2020 | Yang et al. |
| 10,835,711 B2 | 11/2020 | Yang et al. |
| 10,856,898 B2 | 12/2020 | Matsushita et al. |
| 10,888,280 B2 | 1/2021 | Newberry |
| 10,905,850 B2 | 2/2021 | Christian et al. |
| 11,020,030 B2 | 6/2021 | Tao et al. |
| 11,065,018 B2 | 7/2021 | Buck et al. |
| 11,076,876 B2 | 8/2021 | Vale |
| 11,123,090 B2 | 9/2021 | Yang et al. |
| 11,134,859 B2 | 10/2021 | Strasser |
| 11,147,949 B2 | 10/2021 | Yang et al. |
| 11,197,683 B1 | 12/2021 | Teigen et al. |
| 11,207,096 B2 | 12/2021 | To et al. |
| 11,207,497 B1 | 12/2021 | Yee et al. |
| 2001/0031980 A1 | 10/2001 | Wensel et al. |
| 2001/0031981 A1 | 10/2001 | Evans et al. |
| 2001/0049486 A1 | 12/2001 | Evans et al. |
| 2002/0016565 A1 | 2/2002 | Zadno-Azizi et al. |
| 2002/0026145 A1 | 2/2002 | Bagaoisan et al. |
| 2002/0074276 A1 | 6/2002 | Nakashima |
| 2002/0091372 A1 | 7/2002 | Cragg et al. |
| 2002/0156459 A1 | 10/2002 | Ye et al. |
| 2002/0156460 A1 | 10/2002 | Ye et al. |
| 2002/0169467 A1 | 11/2002 | Heitzmann et al. |
| 2002/0177899 A1 | 11/2002 | Eum et al. |
| 2002/0188314 A1 | 12/2002 | Anderson et al. |
| 2003/0088266 A1 | 5/2003 | Bowlin |
| 2003/0135193 A1 | 7/2003 | Hilgers et al. |
| 2003/0135198 A1 | 7/2003 | Berhow et al. |
| 2003/0153874 A1 | 8/2003 | Tai |
| 2003/0195467 A1 | 10/2003 | Mickley |
| 2003/0195546 A1 | 10/2003 | Solar et al. |
| 2003/0225336 A1 | 12/2003 | Callister et al. |
| 2004/0010280 A1 | 1/2004 | Adams et al. |
| 2004/0059290 A1 | 3/2004 | Palasis |
| 2004/0138693 A1 | 7/2004 | Eskuri et al. |
| 2004/0153049 A1 | 8/2004 | Hewitt et al. |
| 2004/0199201 A1 | 10/2004 | Kellett et al. |
| 2004/0236215 A1 | 11/2004 | Mihara et al. |
| 2004/0243102 A1 | 12/2004 | Berg et al. |
| 2005/0004523 A1 | 1/2005 | Osborne et al. |
| 2005/0004553 A1 | 1/2005 | Douk |
| 2005/0021002 A1 | 1/2005 | Deckman et al. |
| 2005/0055047 A1 | 3/2005 | Greenhalgh |
| 2005/0059957 A1 | 3/2005 | Campbell et al. |
| 2005/0080400 A1* | 4/2005 | Corcoran .......... A61M 25/0043 604/523 |
| 2005/0103332 A1 | 5/2005 | Gingles et al. |
| 2005/0137680 A1 | 6/2005 | Ortiz et al. |
| 2005/0182386 A1 | 8/2005 | Aggerholm |
| 2006/0030835 A1 | 2/2006 | Sherman et al. |
| 2006/0064036 A1 | 3/2006 | Osborne et al. |
| 2006/0095062 A1 | 5/2006 | Stephens |
| 2006/0100530 A1 | 5/2006 | Kliot et al. |
| 2006/0111649 A1 | 5/2006 | Zhou |
| 2006/0124212 A1 | 6/2006 | Zhou |
| 2006/0149355 A1 | 7/2006 | Mitelberg et al. |
| 2006/0217664 A1 | 9/2006 | Hattler et al. |
| 2006/0247755 A1 | 11/2006 | Pal et al. |
| 2006/0264759 A1 | 11/2006 | Moehring et al. |
| 2007/0016132 A1 | 1/2007 | Oepen et al. |
| 2007/0043333 A1 | 2/2007 | Kampa et al. |
| 2007/0060888 A1 | 3/2007 | Goff et al. |
| 2007/0185521 A1 | 8/2007 | Bui et al. |
| 2007/0197956 A1 | 8/2007 | Le et al. |
| 2007/0225614 A1 | 9/2007 | Naghavi et al. |
| 2008/0064984 A1 | 3/2008 | Pflueger et al. |
| 2008/0086110 A1 | 4/2008 | Galdonik et al. |
| 2008/0097251 A1 | 4/2008 | Babaev et al. |
| 2008/0188928 A1 | 8/2008 | Salahieh et al. |
| 2008/0234715 A1 | 9/2008 | Pesce |
| 2008/0262350 A1 | 10/2008 | Unger |
| 2008/0300544 A1 | 12/2008 | Palm et al. |
| 2008/0312639 A1 | 12/2008 | Weber |
| 2009/0030400 A1 | 1/2009 | Bose et al. |
| 2009/0043330 A1 | 2/2009 | To |
| 2009/0182370 A1 | 7/2009 | Volobuyev et al. |
| 2009/0187143 A1 | 7/2009 | Vreeman |
| 2009/0209857 A1 | 8/2009 | Secretain et al. |
| 2009/0210048 A1 | 8/2009 | Amplatz et al. |
| 2009/0227992 A1 | 9/2009 | Nir et al. |
| 2009/0234321 A1 | 9/2009 | Shapland et al. |
| 2009/0264865 A1 | 10/2009 | Kawai |
| 2009/0270888 A1 | 10/2009 | Patel et al. |
| 2009/0275974 A1 | 11/2009 | Marchand et al. |
| 2009/0312699 A1 | 12/2009 | Pudelko |
| 2010/0030256 A1 | 2/2010 | Dubrul et al. |
| 2010/0049168 A1 | 2/2010 | Parker et al. |
| 2010/0057051 A1 | 3/2010 | Howat et al. |
| 2010/0114017 A1 | 5/2010 | Lenker et al. |
| 2010/0125253 A1 | 5/2010 | Olson et al. |
| 2010/0217235 A1 | 8/2010 | Thorstenson et al. |
| 2010/0217276 A1 | 8/2010 | Garrison et al. |
| 2010/0312141 A1 | 12/2010 | Keast et al. |
| 2011/0009875 A1 | 1/2011 | Grandfield et al. |
| 2011/0034986 A1 | 2/2011 | Chou |
| 2011/0054504 A1 | 3/2011 | Porter |
| 2011/0082373 A1 | 4/2011 | Gurley et al. |
| 2011/0106200 A1 | 5/2011 | Ziegler |
| 2011/0137399 A1 | 6/2011 | Chomas et al. |
| 2011/0152998 A1 | 6/2011 | Berez et al. |
| 2011/0172700 A1 | 7/2011 | Bose et al. |
| 2011/0178418 A1 | 7/2011 | Avidor et al. |
| 2011/0230859 A1 | 9/2011 | Galdonik et al. |
| 2011/0238041 A1 | 9/2011 | Lim et al. |
| 2011/0295217 A1 | 12/2011 | Tanaka et al. |
| 2012/0040858 A1 | 2/2012 | Ford et al. |
| 2012/0041474 A1 | 2/2012 | Eckhouse |
| 2012/0065479 A1 | 3/2012 | Lahiji et al. |
| 2012/0065490 A1 | 3/2012 | Zharov et al. |
| 2012/0078140 A1 | 3/2012 | Nita |
| 2012/0083868 A1 | 4/2012 | Shrivastava et al. |
| 2012/0123327 A1 | 5/2012 | Miller |
| 2012/0143237 A1 | 6/2012 | Cam et al. |
| 2012/0150147 A1 | 6/2012 | Leynov et al. |
| 2012/0290067 A1 | 11/2012 | Cam et al. |
| 2012/0330196 A1 | 12/2012 | Nita |
| 2013/0006225 A1 | 1/2013 | Cucin |
| 2013/0018318 A1 | 1/2013 | Ravichandran et al. |
| 2013/0018359 A1 | 1/2013 | Coyle |
| 2013/0035628 A1 | 2/2013 | Garrison et al. |
| 2013/0046285 A1 | 2/2013 | Griffin et al. |
| 2013/0046374 A1 | 2/2013 | Jones-McMeans |
| 2013/0116701 A1 | 5/2013 | Wang et al. |

(56) References Cited

U.S. PATENT DOCUMENTS

| | | |
|---|---|---|
| 2013/0131641 A1 | 5/2013 | Jimenez et al. |
| 2013/0131710 A1 | 5/2013 | Carmeli et al. |
| 2013/0158578 A1 | 6/2013 | Ghodke et al. |
| 2014/0025043 A1 | 1/2014 | Wang et al. |
| 2014/0074144 A1 | 3/2014 | Shrivastava et al. |
| 2014/0114287 A1 | 4/2014 | Beasley et al. |
| 2014/0121746 A1 | 5/2014 | Kusleika et al. |
| 2014/0155932 A1 | 6/2014 | Bose et al. |
| 2014/0155980 A1 | 6/2014 | Turjman et al. |
| 2014/0163367 A1 | 6/2014 | Eskuri |
| 2014/0228808 A1 | 8/2014 | Webster et al. |
| 2014/0243882 A1 | 8/2014 | Ma |
| 2014/0249508 A1 | 9/2014 | Wang et al. |
| 2014/0273920 A1 | 9/2014 | Smith |
| 2014/0275832 A1 | 9/2014 | Muehlsteff et al. |
| 2014/0275852 A1 | 9/2014 | Hong et al. |
| 2014/0276167 A1 | 9/2014 | Dasgupta et al. |
| 2014/0276618 A1 | 9/2014 | Di Caprio et al. |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296889 A1 | 10/2014 | Avneri et al. |
| 2014/0309533 A1 | 10/2014 | Yamashita et al. |
| 2014/0330286 A1 | 11/2014 | Wallace |
| 2014/0343537 A1 | 11/2014 | Eversull et al. |
| 2014/0350645 A1 | 11/2014 | Diller et al. |
| 2014/0358123 A1 | 12/2014 | Ueda |
| 2014/0371718 A1 | 12/2014 | Alvarez et al. |
| 2015/0005704 A1 | 1/2015 | Heisei et al. |
| 2015/0046148 A1 | 2/2015 | Oh et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0157220 A1 | 6/2015 | Fish et al. |
| 2015/0157772 A1 | 6/2015 | Li et al. |
| 2015/0173782 A1 | 6/2015 | Garrison et al. |
| 2015/0174363 A1 | 6/2015 | Sutermeister et al. |
| 2015/0257659 A1 | 9/2015 | Broers et al. |
| 2015/0290390 A1 | 10/2015 | Ring et al. |
| 2015/0335288 A1 | 11/2015 | Toth et al. |
| 2015/0335857 A1 | 11/2015 | Ishikawa |
| 2015/0359547 A1 | 12/2015 | Vale et al. |
| 2015/0366518 A1 | 12/2015 | Sampson |
| 2016/0000443 A1 | 1/2016 | Lilburn et al. |
| 2016/0008572 A1 | 1/2016 | Di Caprio |
| 2016/0030079 A1 | 2/2016 | Cohen |
| 2016/0038174 A1 | 2/2016 | Bruzzi et al. |
| 2016/0051386 A1 | 2/2016 | Haarmann-Theimann |
| 2016/0058459 A1 | 3/2016 | Bowman |
| 2016/0081825 A1 | 3/2016 | Sudin et al. |
| 2016/0100819 A1 | 4/2016 | Tieu |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0144157 A1 | 5/2016 | Gulachenski et al. |
| 2016/0151010 A1 | 6/2016 | Erez |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney et al. |
| 2016/0206216 A1 | 7/2016 | Kirenko |
| 2016/0206322 A1 | 7/2016 | Fitz et al. |
| 2016/0213396 A1 | 7/2016 | Dowell et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346508 A1 | 12/2016 | Williams et al. |
| 2016/0346515 A1 | 12/2016 | Buller |
| 2016/0354532 A1 | 12/2016 | Olesky et al. |
| 2016/0361180 A1 | 12/2016 | Vong et al. |
| 2016/0361459 A1 | 12/2016 | Baldwin |
| 2016/0367274 A1 | 12/2016 | Wallace |
| 2016/0367275 A1 | 12/2016 | Wallace |
| 2017/0007264 A1 | 1/2017 | Cruise et al. |
| 2017/0007277 A1 | 1/2017 | Drapeau et al. |
| 2017/0020540 A1 | 1/2017 | Chou et al. |
| 2017/0027604 A1 | 2/2017 | Wallace |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0043124 A1 | 2/2017 | Vreeman |
| 2017/0056061 A1 | 3/2017 | Ogle et al. |
| 2017/0071624 A1 | 3/2017 | McGuckin et al. |
| 2017/0072163 A1 | 3/2017 | Lim et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0100142 A1 | 4/2017 | Look et al. |
| 2017/0105743 A1 | 4/2017 | Vale et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0181835 A1 | 6/2017 | Kleshinski et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0239440 A1* | 8/2017 | Yang ............... A61M 25/0147 |
| 2017/0246014 A1 | 8/2017 | Rapaport et al. |
| 2017/0252057 A1 | 9/2017 | Bonnette et al. |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0303949 A1 | 10/2017 | Jacobi et al. |
| 2017/0340867 A1 | 11/2017 | Accisano |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou et al. |
| 2017/0367713 A1 | 12/2017 | Green et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Paniam |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0042623 A1 | 2/2018 | Batiste |
| 2018/0055364 A1 | 3/2018 | Pierro |
| 2018/0055516 A1 | 3/2018 | Bagaoisan et al. |
| 2018/0104390 A1 | 4/2018 | Kilcran |
| 2018/0200478 A1 | 7/2018 | Lorenzo et al. |
| 2018/0207395 A1 | 7/2018 | Bulman et al. |
| 2018/0207399 A1 | 7/2018 | Chou et al. |

(56) References Cited

U.S. PATENT DOCUMENTS

| | | |
|---|---|---|
| 2018/0207412 A1 | 7/2018 | Malek et al. |
| 2018/0228502 A1 | 8/2018 | Shaffer et al. |
| 2018/0242962 A1* | 8/2018 | Walen .............. A61B 17/1631 |
| 2018/0242980 A1 | 8/2018 | Lubock et al. |
| 2018/0242989 A1 | 8/2018 | Nita |
| 2018/0242999 A1 | 8/2018 | Thatipelli |
| 2018/0250013 A1 | 9/2018 | Wallace et al. |
| 2018/0263632 A1 | 9/2018 | Seifert et al. |
| 2018/0263642 A1 | 9/2018 | Nita |
| 2018/0279965 A1 | 10/2018 | Pandit et al. |
| 2018/0289340 A1 | 10/2018 | Trindade Rodrigues et al. |
| 2018/0296236 A1 | 10/2018 | Goldfarb et al. |
| 2018/0353194 A1 | 12/2018 | Shaffer et al. |
| 2019/0022363 A1 | 1/2019 | Grayzel et al. |
| 2019/0029825 A1 | 1/2019 | Fitterer et al. |
| 2019/0070387 A1 | 3/2019 | Goyal |
| 2019/0105477 A1 | 4/2019 | Heilman et al. |
| 2019/0105478 A1 | 4/2019 | Malek et al. |
| 2019/0108540 A1 | 4/2019 | Look et al. |
| 2019/0167124 A1 | 6/2019 | Verkruijsse et al. |
| 2019/0175030 A1 | 6/2019 | Verkruijsse et al. |
| 2019/0200871 A1 | 7/2019 | De Haan |
| 2019/0239910 A1 | 8/2019 | Brade et al. |
| 2019/0275290 A1 | 9/2019 | Yamashita et al. |
| 2019/0290884 A1 | 9/2019 | Kanemasa et al. |
| 2019/0329003 A1 | 10/2019 | Watanabe |
| 2019/0336142 A1 | 11/2019 | Torrie |
| 2019/0351182 A1 | 11/2019 | Chou et al. |
| 2020/0001046 A1 | 1/2020 | Yang et al. |
| 2020/0008820 A1 | 1/2020 | Aboytes et al. |
| 2020/0009301 A1 | 1/2020 | Yee |
| 2020/0009350 A1 | 1/2020 | Goyal |
| 2020/0022712 A1 | 1/2020 | Deville et al. |
| 2020/0023160 A1 | 1/2020 | Chou et al. |
| 2020/0046368 A1 | 2/2020 | Merritt et al. |
| 2020/0046937 A1 | 2/2020 | Nakagawa et al. |
| 2020/0170521 A1 | 6/2020 | Gupta et al. |
| 2020/0171276 A1 | 6/2020 | Onozuka |
| 2020/0171277 A1 | 6/2020 | Garrison et al. |
| 2020/0188630 A1 | 6/2020 | Fujita et al. |
| 2020/0025845 A1 | 7/2020 | Yang et al. |
| 2020/0205845 A1 | 7/2020 | Yang et al. |
| 2020/0276411 A1 | 9/2020 | Ogle et al. |
| 2020/0289136 A1 | 9/2020 | Chou |
| 2020/0297362 A1 | 9/2020 | Deville et al. |
| 2020/0297972 A1 | 9/2020 | Yee et al. |
| 2020/0306501 A1 | 10/2020 | Yee et al. |
| 2020/0323535 A1 | 10/2020 | Yang et al. |
| 2020/0337716 A1 | 10/2020 | Garrison et al. |
| 2020/0345979 A1 | 11/2020 | Loh et al. |
| 2021/0045758 A1 | 2/2021 | Garrison et al. |
| 2021/0052296 A1 | 2/2021 | Garrison |
| 2021/0068852 A1 | 3/2021 | Spence |
| 2021/0093336 A1 | 4/2021 | Roue |
| 2021/0106792 A1 | 4/2021 | Rafiee |
| 2021/0128182 A1 | 5/2021 | Teigen et al. |
| 2021/0146094 A1 | 5/2021 | Christian et al. |
| 2021/0153744 A1 | 5/2021 | Pierro |
| 2021/0186537 A1 | 6/2021 | Buck et al. |
| 2021/0186542 A1 | 6/2021 | Buck et al. |
| 2021/0187244 A1 | 6/2021 | Buck et al. |
| 2021/0315596 A1 | 10/2021 | Buck et al. |
| 2021/0315597 A1 | 10/2021 | Buck et al. |
| 2021/0315598 A1 | 10/2021 | Buck et al. |
| 2021/0316121 A1 | 10/2021 | Buck et al. |
| 2021/0316127 A1 | 10/2021 | Buck et al. |
| 2021/0361909 A1 | 11/2021 | Cottone et al. |
| 2021/0378527 A1 | 12/2021 | Strasser et al. |
| 2021/0378696 A1 | 12/2021 | Yang et al. |
| 2022/0047849 A1 | 2/2022 | Yee et al. |
| 2022/0211975 A1 | 7/2022 | Yang et al. |

FOREIGN PATENT DOCUMENTS

| | | |
|---|---|---|
| DE | 10 2010 053111 | 6/2012 |
| DE | 10 2012 112732 | 6/2014 |
| EP | 0 330 843 | 12/1993 |
| EP | 0 582 533 | 2/1994 |
| EP | 0 309 471 | 8/1996 |
| EP | 1 349 486 | 3/2008 |
| EP | 2 069 528 | 3/2013 |
| EP | 2 937 108 | 10/2015 |
| EP | 2 928 360 | 1/2017 |
| EP | 2 211 732 | 5/2018 |
| EP | 3 539 486 | 9/2019 |
| EP | 3 698 740 | 8/2020 |
| GB | 2077132 | 12/1981 |
| JP | 2002-535049 | 10/2002 |
| JP | 2003-527925 | 9/2003 |
| JP | 2006-102222 | 4/2006 |
| JP | 2006-521881 | 9/2006 |
| JP | 2008-502378 | 1/2008 |
| JP | 2013-504388 | 2/2013 |
| JP | 2014-515670 | 7/2014 |
| JP | 2015-504327 | 2/2015 |
| WO | WO 1995/009659 | 4/1995 |
| WO | WO 2000/000100 | 1/2000 |
| WO | WO 2009/054968 | 4/2009 |
| WO | WO 2009/132218 | 10/2009 |
| WO | WO 2010/126786 | 11/2010 |
| WO | WO 2014/151209 | 9/2014 |
| WO | WO 2014/203336 | 12/2014 |
| WO | WO 2017/025775 | 2/2017 |
| WO | WO 2018/121363 | 7/2018 |
| WO | WO 2019/178165 | 9/2019 |
| WO | WO 2019/222518 | 11/2019 |
| WO | WO 2019/246583 | 12/2019 |
| WO | WO 2020/145928 | 7/2020 |
| WO | WO 2021/016213 | 1/2021 |
| WO | WO 2021/064955 | 4/2021 |
| WO | WO 2021/090821 | 5/2021 |
| WO | WO 2021/105658 | 6/2021 |
| WO | WO 2021/242734 | 12/2021 |

OTHER PUBLICATIONS

U.S. Appl. No. 16/542,657, filed Aug. 16, 2019, Method of Making an Enhanced Flexibility Neurovascular Catheter.

U.S. Appl. No. 16/400,263, filed May 1, 2019, Neurovascular Catheter Having Atraumatic Angled Tip.

U.S. Appl. No. 16/570,084, filed Sep. 13, 2019, Enhanced Flexibility Neurovascular Catheter With Tensile Support.

U.S. Appl. No. 17/070,832, filed Oct. 14, 2020, Systems and Methods for Multivariate Stroke Detection.

U.S. Appl. No. 17/125,743, filed Dec. 17, 2020, Systems for Accessing a Central Pulmonary Artery.

U.S. Appl. No. 17/357,558, filed Jun. 24, 2021, Aspiration System With Accelerated Response.

U.S. Appl. No. 17/343,004, filed Jun. 9, 2021, Catheter With Enhanced Tensile Strength.

Abay et al., 2014, Investigation of photoplethysmography and Near Infrared Spectroscopy for the assessment of tissue blood perfusion, 36th Annual International Conference of the IEEE Engineering in Medicine and Biology Society, Chicago, IL, pp. 5361-5364, doi: 10.1109/EMBC.2014.6944837.

Guidezilla Guide Extension Catheter, Boston Scientific 510k Submission, Feb. 20, 2017.

Korpelainen et al., 1995, Asymmetrical skin temperature in ischemic stroke, Stroke, 26(9):1543-1547.

Merit Medical Systems Acquired Distal Access's SPINR Platform, Jul. 15, 2015, Digital Access, LLC; Merit Medical Systems, 5 pages.

Simon et al., *Exploring the efficacy of cyclic vs. static aspiration in a cerebral thrombectomy model: an initial proof of concept study*, J. NeuroIntervent Surg 2014, 6 pp. 677-683.

Simon et al., *Hydrodynamic comparison of the Penumbra system and commonly available syringes in forced—suction thrombectomy*, J. NeuroIntervent Surg 2014, 6, pp. 205-211.

(56) References Cited

OTHER PUBLICATIONS

Spiotta et al., Evolution of thrombectomy approaches and devices for acute stroke: a technical review, J. NeuroIntervent Surg 2015, 7, pp. 2-7.
International Search Report and Written Opinion dated Jul. 8, 2021 in application No. PCT/US2021/021382.
Bernava et al., Sep. 23, 2019, Direct trhomboaspiration efficacy for mechanical thrombectomy is related to the angle of interaction between the catheter and the clot, J. NeuroIntervent Surg., 0:1-6, doi:10.1136/neurintsurg-2019-015113.
U.S. Appl. No. 16/589,563, filed Oct. 1, 2019, Devices and Methods for Removing Obstructive Material From an Intravascular Site.
U.S. Appl. No. 15/862,488 (U.S. Pat. No. 10,653,426), filed Jan. 4, 2018 (May 19, 2020), Thromboresistant Coatings for Aneurysm Treatment Devices.
U.S. Appl. No. 16/863,723 (U.S. Pat. No. 11,224,434), filed Apr. 30, 2020 (Jan. 18, 2022), Thromboresistant Coatings for Aneurysm Treatment Devices.
U.S. Appl. No. 17/574,907, filed Jan. 13, 2022, Thromboresistant Coatings for Aneurysm Treatment Devices.
U.S. Appl. No. 15/442,393 (U.S. Pat. No. 10,183,145), filed Feb. 24, 2017 (Jan. 22, 2019), Enhanced Flexibility Neurovascular Catheter.
U.S. Appl. No. 15/443,874 (U.S. Pat. No. 10,835,711), filed Feb. 27, 2017 (Nov. 17, 2020), Telescoping Neurovascular Catheter With Enlargeable Distal Opening.
U.S. Appl. No. 15/443,841 (U.S. Pat. No. 10,661,053), filed Feb. 27, 2017 (May 26, 2020), Method of Pulsatile Neurovascular Aspiration With Telescoping Catheter.
U.S. Appl. No. 15/443,838 (U.S. Pat. No. 10,179,224), filed Feb. 27, 2017 (Jan. 15, 2019), Enhanced Flexibility Neurovascular Catheter With Tensile Support.
U.S. Appl. No. 15/443,877 (U.S. Pat. No. 10,183,146), filed Feb. 27, 2017 (Jan. 22, 2019), Method of Making an Enhanced Flexibility Neurovascular Catheter.
U.S. Appl. No. 15/443,948 (U.S. Pat. No. 10,441,745), filed Feb. 27, 2017 (Oct. 15, 2019), Neurovascular Catheter With Enlargeable Distal End.
U.S. Appl. No. 16/542,657 (U.S. Pat. No. 11,147,949), filed Aug. 16, 2019 (Oct. 19, 2021), Method of Making an Enhanced Flexibility Neurovascular Catheter.
U.S. Appl. No. 17/502,389, filed Oct. 15, 2021, Neurovascular Catheter With Enlargeable Distal End.
U.S. Appl. No. 15/444,038 (U.S. Pat. No. 10,183,147), filed Feb. 27, 2017 (Jan. 22, 2019), Neurovascular Catheter Extension Segment.
U.S. Appl. No. 16/833,585, filed Mar. 28, 2020, Enhanced Flexibility Neurovascular Catheter.
U.S. Appl. No. 16/503,899, filed Jul. 5, 2019, Sealed Neurovascular Extendable Catheter.
U.S. Appl. No. 16/802,317, filed Feb. 26, 2020, Catheter With Seamless Flexibility Transitions.
U.S. Appl. No. 16/503,886, filed Jul. 5, 2019, Vacuum Transfer Tool for Extendable Catheter.
U.S. Appl. No. 16/398,626 (U.S. Pat. No. 10,835,272), filed Apr. 30, 2019 (Nov. 17, 2020), Devices and Methods for Removing Obstructive Material From an Intravascular Site.
U.S. Appl. No. 16/400,263 (U.S. Pat. No. 11,123,090), filed May 1, 2019 (Sep. 21, 2021), Neurovascular Catheter Having Atraumatic Angled Tip.
U.S. Appl. No. 16/570,084 (U.S. Pat. No. 11,311,303), filed Sep. 13, 2019 (Apr. 26, 2022), Enhanced Flexibility Neurovascular Catheter With Tensile Support.
U.S. Appl. No. 16/683,718 (U.S. Pat. No. 10,653,434), filed Nov. 14, 2019 (May 19, 2020), Devices and Methods for Removing Obstructive Material From an Intravascular Site.
U.S. Appl. No. 16/704,330 (U.S. Pat. No. 10,786,270), filed Dec. 5, 2019 (Sep. 29, 2020), Neurovascular Aspiration Catheter With Elliptical Aspiration Port.
U.S. Appl. No. 17/410,162, filed Aug. 24, 2021, Neurovascular Catheter Having Angled Tip.
U.S. Appl. No. 16/589,563 (U.S. Pat. No. 11,395,665), filed Oct. 1, 2019 (Jul. 26, 2022), Devices and Methods for Removing Obstructive Material From an Intravascular Site.
U.S. Appl. No. 17/036,258, filed Sep. 29, 2020, Embolic Retrieval Catheter.
U.S. Appl. No. 17/070,832 (U.S. Pat. No. 11,134,859), filed Oct. 14, 2020 (Oct. 5, 2021), Systems and Methods for Multivariate Stroke Detection.
U.S. Appl. No. 17/407,852, filed Aug. 20, 2021, Systems and Methods for Multivariate Stroke Detection.
U.S. Appl. No. 16/728,469, filed Dec. 27, 2019, Neurovascular Access With Dynamic Assistance.
U.S. Appl. No. 17/125,723 (U.S. Pat. No. 11,065,018), filed Dec. 17, 2020 (Jul. 20, 2021), Methods and Systems for Advancing a Catheter to a Target Site.
U.S. Appl. No. 17/125,217, filed Dec. 17, 2020, Methods and Systems for Treating a Pulmonary Embolism.
U.S. Appl. No. 17/125,743 (U.S. Pat. No. 11,253,277), filed Dec. 17, 2020 (Feb. 22, 2022), Systems for Accessing a Central Pulmonary Artery.
U.S. Appl. No. 17/125,742, filed Dec. 17, 2020, Methods and Systems for Accessing and Retrieving Thrombo-Emboli.
U.S. Appl. No. 17/357,490, filed Jun. 24, 2021, Catheter System for Treating Thromboembolic Disease.
U.S. Appl. No. 17/357,558 (U.S. Pat. No. 11,259,821), filed Jun. 24, 2021 (Mar. 1, 2022), Aspiration System With Accelerated Response.
U.S. Appl. No. 17/357,643, filed Jun. 24, 2021, Hemostasis Valve.
U.S. Appl. No. 17/357,672, filed Jun. 24, 2021, Split Dilator Aspiration System.
U.S. Appl. No. 17/357,715, filed Jun. 24, 2021, Methods of Placing Large Bore Aspiration Catheters.
U.S. Appl. No. 17/343,004 (U.S. Pat. No. 11,207,497), filed Jun. 9, 2021 (Dec. 28, 2021), Catheter With Enhanced Tensile Strength.
U.S. Appl. No. 17/398,244, filed Aug. 10, 2021, Catheter With a Preset Curve.
U.S. Appl. No. 29/811,884, filed Oct. 18, 2021, Inline Fluid Filter.
U.S. Appl. No. 17/527,393, filed Nov. 16, 2021, Catheter Drive System for Supra-Aortic Access.
U.S. Appl. No. 17/527,379, filed Nov. 16, 2021, Robotically Driven Interventional Device.
U.S. Appl. No. 17/527,460, filed Nov. 16, 2021, Sterile Packaging Assembly for Robotic Interventional Device.
U.S. Appl. No. 17/527,452, filed Nov. 16, 2021, Method of Robotically Performing a Neurovascular Procedure.
U.S. Appl. No. 17/527,456, filed Nov. 16, 2021, Multi Catheter Method of Performing a Robotic Neurovascular Procedure.

\* cited by examiner

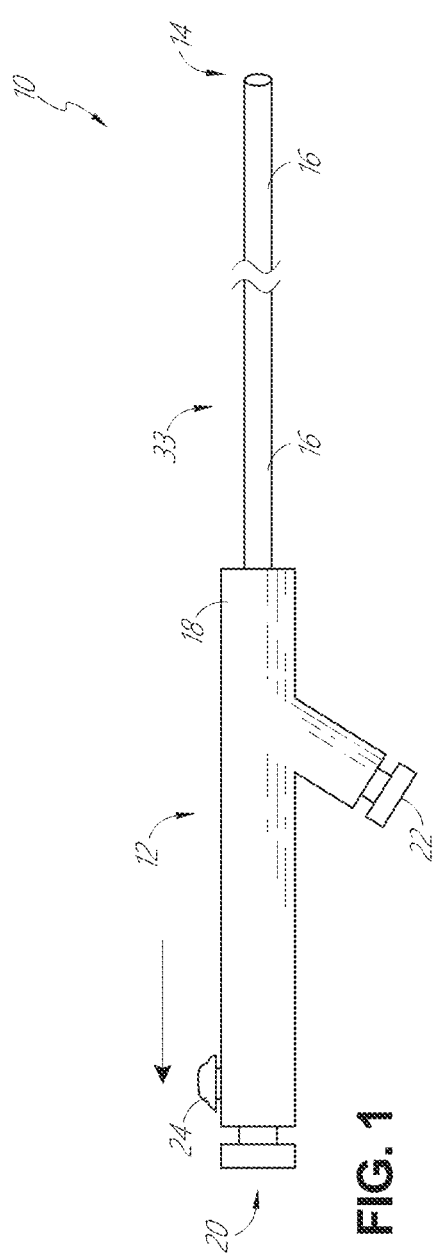
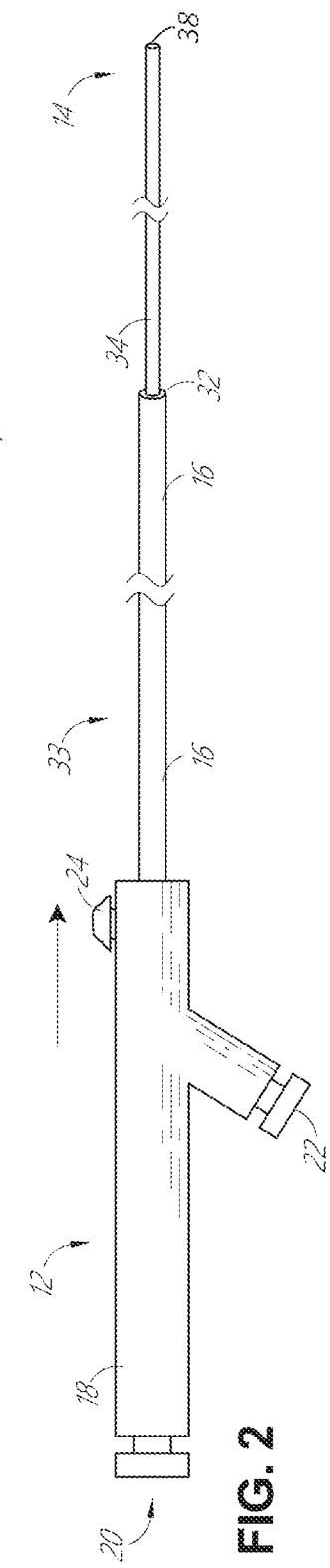
FIG. 1
FIG. 2

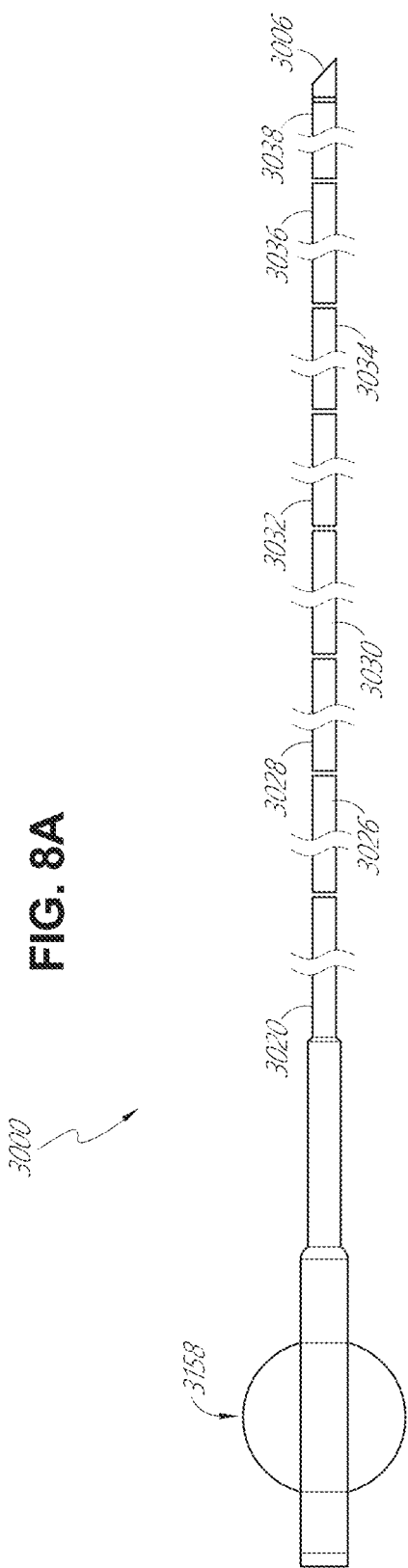
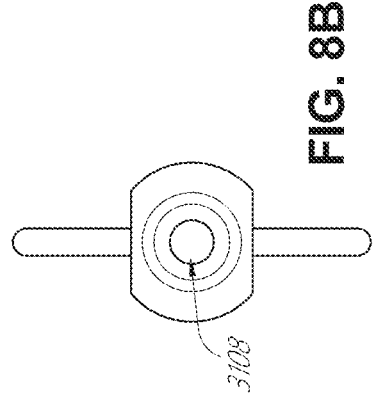

ENHANCED FLEXIBILITY NEUROVASCULAR CATHETER

CROSS-REFERENCE TO RELATED APPLICATIONS

This application claims priority as a continuation-in-part of International Patent Application No. PCT/US2021/021382, filed Mar. 8, 2021, which claims the priority benefit under 35 U.S.C. § 119(e) of U.S. Provisional Patent Application No. 62/987,546, filed Mar. 10, 2020, the entirety of each of which is hereby incorporated by reference herein.

BACKGROUND

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. When a patient presents with neurological symptoms and signs which resolve completely within 1 hour, the term transient ischemic attack (TIA) is used. Etiologically, TIA and stroke share the same pathophysiologic mechanisms and thus represent a continuum based on persistence of symptoms and extent of ischemic insult.

Emboli occasionally form around the valves of the heart or in the left atrial appendage during periods of irregular heart rhythm and then are dislodged and follow the blood flow into the distal regions of the body. Those emboli can pass to the brain and cause an embolic stroke. As will be discussed below, many such occlusions occur in the middle cerebral artery (MCA), although such is not the only site where emboli come to rest.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

Traditionally, emergent management of acute ischemic stroke consisted mainly of general supportive care, e.g. hydration, monitoring neurological status, blood pressure control, and/or anti-platelet or anti-coagulation therapy. In 1996, the Food and Drug Administration approved the use of Genentech Inc.'s thrombolytic drug, tissue plasminogen activator (t-PA) or Activase®, for treating acute stroke. A randomized, double-blind trial, the National Institute of Neurological Disorders and t-PA Stroke Study, revealed a statistically significant improvement in stroke scale scores at 24 hours in the group of patients receiving intravenous t-PA within 3 hours of the onset of an ischemic stroke. Since the approval of t-PA, an emergency room physician could, for the first time, offer a stroke patient an effective treatment besides supportive care.

However, treatment with systemic t-PA is associated with increased risk of intracerebral hemorrhage and other hemorrhagic complications. Patients treated with t-PA were more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include the following: if the patient has had a previous stroke or serious head trauma in the preceding 3 months, if the patient has a systolic blood pressure above 185 mm Hg or diastolic blood pressure above 110 mmHg, if the patient requires aggressive treatment to reduce the blood pressure to the specified limits, if the patient is taking anticoagulants or has a propensity to hemorrhage, and/or if the patient has had a recent invasive surgical procedure. Therefore, only a small percentage of selected stroke patients are qualified to receive t-PA.

Obstructive emboli have also been mechanically removed from various sites in the vasculature for years. Mechanical therapies have involved capturing and removing the clot, dissolving the clot, disrupting and suctioning the clot, and/or creating a flow channel through the clot. One of the first mechanical devices developed for stroke treatment is the MERCI Retriever System (Concentric Medical, Redwood City, Calif.). A balloon-tipped guide catheter is used to access the internal carotid artery (ICA) from the femoral artery. A microcatheter is placed through the guide catheter and used to deliver the coil-tipped retriever across the clot and is then pulled back to deploy the retriever around the clot. The microcatheter and retriever are then pulled back, with the goal of pulling the clot, into the balloon guide catheter while the balloon is inflated and a syringe is connected to the balloon guide catheter to aspirate the guide catheter during clot retrieval. This device has had initially positive results as compared to thrombolytic therapy alone.

Other thrombectomy devices utilize expandable cages, baskets, or snares to capture and retrieve clot. Temporary stents, sometimes referred to as stentrievers or revascularization devices, are utilized to remove or retrieve clot as well as restore flow to the vessel. A series of devices using active laser or ultrasound energy to break up the clot have also been utilized. Other active energy devices have been used in conjunction with intra-arterial thrombolytic infusion to accelerate the dissolution of the thrombus. Many of these devices are used in conjunction with aspiration to aid in the removal of the clot and reduce the risk of emboli. Suctioning of the clot has also been used with single-lumen catheters and syringes or aspiration pumps, with or without adjunct disruption of the clot. Devices which apply powered fluid vortices in combination with suction have been utilized to improve the efficacy of this method of thrombectomy. Finally, balloons or stents have been used to create a patent lumen through the clot when clot removal or dissolution was not possible.

Notwithstanding the foregoing, there remains a need for new devices and methods for treating vasculature occlusions in the body, including acute ischemic stroke and occlusive cerebrovascular disease.

SUMMARY

In accordance with one aspect of the present invention, there is provided an enhanced flexibility catheter for navigating remote, tortuous vasculature such as for neurovascular procedures. The catheter comprises an elongate flexible tubular body, having a proximal end, a distal end, a longitudinal axis and a side wall defining a central lumen. The elongate flexible tubular body may comprise an outer jacket formed from a plurality of axially adjacent tubular segments. A distal end face of a first proximal tubular segment and a proximal end face of an adjacent distal tubular segment are inclined at a non normal angle with respect to the longitudinal axis, and joined together to form an inclined junction between the first proximal tubular segment and the adjacent first distal tubular segment.

A midpoint along the axial length of the first inclined junction may be within the range of from about 40 mm to about 80 mm from the distal end, or within the range of from about 55 mm to about 65 mm from the distal end.

The catheter may further comprise a second inclined junction having a midpoint within the range of from about 70 mm to about 110 mm from the distal end, or within the range of from about 80 mm to about 100 mm from the distal end. The first inclined junction may be inclined by an angle within the range of from about 10 degrees to about 20 degrees from the longitudinal axis. The second inclined junction may be inclined by an angle within the range of from about 20 degrees to about 30 degrees from the longitudinal axis.

The first proximal tubular segment may have a higher durometer than the first distal tubular segment. The first inclined junction and the second inclined junction may be formed at the axial ends of the first proximal tubular segment. The first proximal tubular segment may have an axial length within the range of from about 10 mm to about 50 mm or within the range of from about 20 mm to about 40 mm.

The catheter may further comprise an axially extending filament within the side wall, extending at least about the most distal 10 cm of the length of the catheter. The catheter may further comprise a tubular radiopaque marker in the side wall. The filament may wrap around the marker, and may comprise multiple fibers. The side wall may further comprise an inner liner and a spring coil, and the filament may extend axially in between the coil and the inner liner.

The outer jacket may be formed from at least five discrete tubular segments, or from at least nine discrete tubular segments. A difference in durometer between a proximal one of the tubular segments and a distal one of the tubular segments may be at least about 20 D, or at least about 30 D.

The catheter may be able to withstand at least about 3.5 pounds tension, or at least about 5 pounds tension before failure in the form of marker band detachment. An axial length of the marker band on a leading edge side of the tubular body may be at least about 20% longer than an axial length of the marker band on a trailing edge side of the tubular body. An axial length of the marker band on a leading edge side of the tubular body may be within the range of from about 1 mm to about 5 mm.

In another aspect of the present invention, there is provided a catheter comprising: an elongate flexible body, having a proximal end, a distal end and a side wall defining a central lumen, a distal zone of the side wall comprising: a tubular inner liner; a soft tie layer separated from the lumen by the inner liner; a helical coil surrounding the tie layer, adjacent windings of the coil spaced progressively further apart in the distal direction; and an outer jacket surrounding the helical coil, the outer jacket formed from a plurality of tubular segments positioned coaxially about the coil; wherein a proximal one of the tubular segments has a durometer of at least about 60 D and a distal one of the tubular segments has a durometer of no more than about 35 D. In one aspect of present disclosure, the tubular liner is formed by dip coating a removable mandrel. In another aspect of present disclosure, the tubular liner comprises PTFE.

In yet another aspect of present disclosure, the tie layer comprises polyurethane. The tie layer may have a wall thickness of no more than about 0.005 inches and may extend along at least the most distal 20 cm of the flexible body. In one aspect of present disclosure, the coil comprises a shape memory material. The coil may comprise Nitinol, and the Nitinol may comprise an Austenite state at body temperature.

In one aspect of present disclosure, the outer jacket is formed from at least five discrete tubular segments. The outer jacket may be formed from at least nine discrete tubular segments. The difference in durometer between a proximal one of the tubular segments and a distal one of the tubular segments may be at least about 20 D. The difference in durometer between a proximal one of the tubular segments and a distal one of the tubular segments may be at least about 30 D.

In another aspect of present disclosure, the enhanced flexibility neurovascular catheter, further comprises a tension support for increasing the tension resistance in the distal zone. The tension support may comprise a filament and may comprise an axially extending filament. The axially extending filament may be carried between the inner liner and the helical coil. The axially extending filament may increase the tensile strength to at least about 5 pounds.

In accordance with one aspect, there is provided an enhanced flexibility catheter, comprising: an elongate flexible body having a proximal end, a distal end and a side wall defining a central lumen, wherein the side wall comprises a distal zone comprising a helical coil, and a transition between the distal zone and a proximal zone of the side wall, wherein the transition comprises a distal surface that matches at least a portion of a proximal surface of the helical coil of the distal zone. In some embodiments, the matching creates a uniform gap between the at least a portion of the proximal surface of the helical coil of the distal zone and the distal surface of the transition. In some embodiments, the distal surface of the transition comprises a step. In some embodiments, the distal surface of the transition comprises a step wherein a tangential surface of the step matches a termination of the helical coil of the distal zone. In some embodiments, the transition comprises a tubular body. In some embodiments, the transition comprises a tubular body comprising a planar proximal surface. In some embodiments, the transition comprises a durometer between a durometer of the proximal zone and a durometer of the distal zone. In some embodiments, the transition comprises platinum and a platinum alloy. In some embodiments, the platinum alloy comprises about 90% Platinum and about 10% Iridium. In some embodiments, the proximal zone of the side wall comprises a braid. In some embodiments, the side wall further comprises a tubular inner liner and a tie layer separated from the lumen by the inner liner, wherein the helical coil of the distal zone surrounds the tie layer and the braid of the proximal zone surrounds the tie layer. In some embodiments, the elongate flexible body further comprises an outer jacket formed from a plurality of tubular segments and extending coaxially about the helical coil, wherein a proximal one of the tubular segments has a durometer of at least about 60 D and a distal one of the tubular segments has a durometer of no more than about 35 D. In some embodiments, the elongate flexible body further comprises an axially extending filament within the side wall.

In accordance with one aspect, there is provided an enhanced flexibility catheter comprising: an elongate flexible body having a proximal end, a distal end and a side wall defining a central lumen, wherein the side wall comprises a distal zone comprising a helical coil, and a transition between the distal zone and a proximal zone of the side wall, wherein the transition comprises a distal surface comprising a step, and the distal surface matches at least a portion of a proximal surface of the helical coil of the distal zone. In some embodiments, the matching creates a uniform gap between the at least a portion of the proximal surface of the helical coil of the distal zone and the distal surface of the transition. In some embodiments, the step of the distal surface of the transition comprises a 5/1000 pitch cut from the distal surface. In some embodiments, a tangential surface of the step matches a termination of the helical coil of the distal zone. In some embodiments, the transition comprises a tubular body. In some embodiments, the transition comprises a tubular body comprising a planar proximal surface. In some embodiments, the transition comprises a durometer between a durometer of the proximal zone and a durometer of the distal zone. In some embodiments, the transition comprises platinum and a platinum alloy. In some embodiments, the platinum alloy comprises about 90% Platinum and about 10% Iridium. In some embodiments, the proximal zone of the side wall comprises a braid. In some embodiments, the side wall further comprises a tubular inner liner and a tie layer separated from the lumen by the inner liner, wherein the helical coil of the distal zone surrounds the tie layer and the braid of the proximal zone surrounds the tie layer. In some embodiments, the elongate flexible body further comprises an outer jacket formed from a plurality of tubular segments and extending coaxially about the helical coil, wherein a proximal one of the tubular segments has a durometer of at least about 60 D and a distal one of the tubular segments has a durometer of no more than about 35 D. In some embodiments, the elongate flexible body further comprises an axially extending filament within the side wall.

Any of the foregoing catheters may be provided with a transition support over a junction between two dissimilar wall constructions, such as over the braid to coil junction, to improve bending characteristics of the catheter. Thus, there is provided an enhanced flexibility catheter, comprising: an elongate flexible body having a proximal end, a distal end, and a side wall defining a central lumen, wherein the side wall comprises: a proximal zone comprising a tubular braid and a first helical coil; a distal zone comprising a second helical coil, and a transition between the distal zone and the proximal zone, wherein the transition comprises a distal end of the tubular braid within 1 cm of a proximal end of the second helical coil, and the first helical coil extends distally beyond the transition.

The distal end of the tubular braid may be within 5 mm, within 2 mm or in contact with the proximal end of the second helical coil. The first helical coil may be formed from a wire having a first diameter, and the second helical coil may be formed from a wire having a second, larger diameter. The first helical coil may comprise stainless steel, and the second helical coil may comprise Nitinol.

A distal section of the braid may be heat annealed for a length of at least about one or two cm and typically no more than 10 cm or 5 cm. The first and second helical coils may be provided with an axial overlapping intertwined zone having a length of at least about 5 mm or 2 cm or 5 cm but generally no more than about 20 cm The side wall may further comprise a tubular inner liner and a tie layer separated from the lumen by the inner liner, wherein the second helical coil of the distal zone is adjacent the tie layer and the braid of the proximal zone is adjacent the tie layer. The elongate flexible body may further comprise an outer jacket formed from a plurality of axially adjacent tubular segments wherein a proximal one of the tubular segments has a durometer of at least about 60 D and a distal one of the tubular segments has a durometer of no more than about 35 D. The elongate flexible body may further comprise an axially extending filament within the side wall.

The catheter may further comprise a tubular support having a proximal end surrounding a distal portion of the braid and a distal end surrounding a proximal portion of the second coil. The tubular support may comprise a slotted metal tube.

There is also provided an enhanced flexibility catheter, comprising: an elongate flexible body having a proximal end, a distal end, and a side wall defining a central lumen, wherein the side wall comprises: a proximal tubular braid having a distal end adjacent a proximal end of a helical coil to form a junction, a tubular metal support spanning the junction; and an outer jacket surrounding the tubular support. The catheter may further comprise an axial filament extending distally from beneath the tubular support.

The side wall may further comprise a tubular inner liner and a tie layer separated from the lumen by the inner liner, wherein the helical coil of the distal zone surrounds the tie layer and the braid of the proximal zone surrounds the tie layer. The elongate flexible body may further comprise an outer jacket formed from a plurality of axially adjacent tubular segments extending coaxially about the helical coil, wherein a proximal one of the tubular segments has a durometer of at least about 60 D and a distal one of the tubular segments has a durometer of no more than about 35 D.

There is also provided a method of making an enhanced flexibility catheter. The method comprises forming a catheter comprising a braid in a proximal zone of the catheter; placing at least a portion of the braid of the catheter over a mandrel; annealing a distal section of the braid comprising induction heating the braid and mandrel in a coil; and visibly monitoring a parameter change of the braid. Induction heating the braid may comprise placing the braid and mandrel within an ERDO induction heater. The parameter change comprises a color change of the braid. The distal annealed section may have an axial length of no more than about 2 cm.

Any feature, structure, or step disclosed herein can be replaced with or combined with any other feature, structure, or step disclosed herein, or omitted. Further, for purposes of summarizing the disclosure, certain aspects, advantages, and features of the embodiments have been described herein. It is to be understood that not necessarily any or all such advantages are achieved in accordance with any particular embodiment disclosed herein. No individual aspects of this disclosure are essential or indispensable. Further features and advantages of the embodiments will become apparent to those of skill in the art in view of the Detailed Description which follows when considered together with the attached drawings and claims.

BRIEF DESCRIPTION OF THE DRAWINGS

FIG. 1 is a side elevational schematic view of an intracranial aspiration catheter in accordance with the some embodiments, with a distal segment in a proximally retracted configuration.

FIG. 2 is a side elevational view as in FIG. 1, with the distal segment in a distally extended configuration.

FIG. 8A illustrates a side elevational view of a progressively enhanced flexibility catheter according to some embodiments.

FIG. 8B is a proximal end view of the enhanced flexibility catheter of FIG. 8A.

DETAILED DESCRIPTION

Figure 3A:
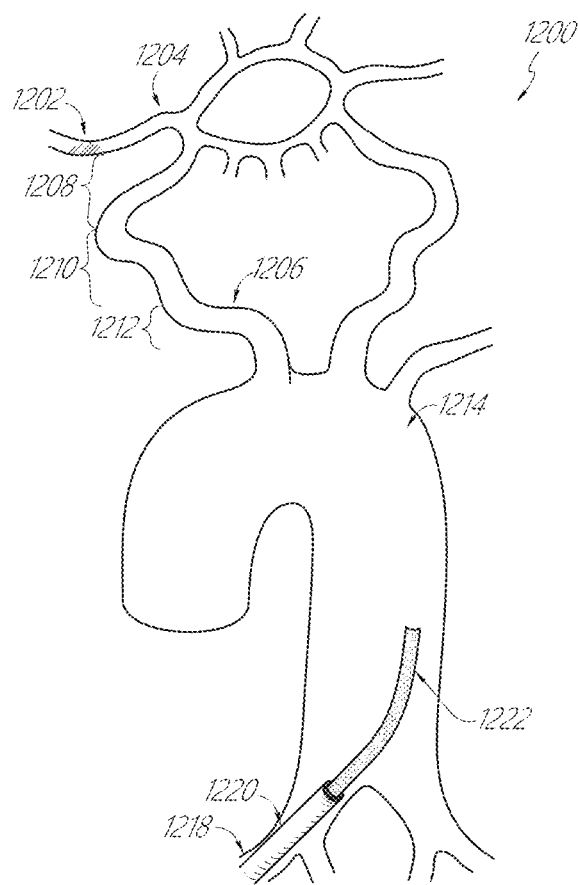
FIGS. 3A-3F depict a sequence of steps in accordance with some embodiments involved in accessing a neurovascular occlusion for aspiration.

Referring to FIG. 1 and FIG. 2, there is disclosed a catheter 10 in accordance with one aspect of present embodiments. Although primarily described in the context of an axially extendable distal segment aspiration catheter with a single central lumen, catheters of present embodiments can readily be modified to incorporate additional structures, such as permanent or removable column strength enhancing mandrels, two or more lumen such as to permit drug, contrast or irrigant infusion or to supply inflation media to one or more inflatable balloons carried by the catheter, or combinations of these features, as will be readily apparent to one of skill in the art in view of the disclosure herein. In addition, present embodiments will be described primarily in the context of removing obstructive material from remote arteries, veins or vasculature in the brain, but have applicability as access catheters for delivery and removal of any of a variety of diagnostics or therapeutic devices with or without aspiration.

The catheters disclosed herein may readily be adapted for use throughout the body wherever it may be desirable to distally advance a low profile or small diameter distal catheter segment from a larger diameter proximal segment. For example, axially extendable catheter shafts in accordance with the present embodiments may be dimensioned for use throughout the coronary and peripheral vasculature, the gastrointestinal tract, the urethra, ureters, Fallopian tubes and other lumens and potential lumens, as well. The telescoping structure of the present embodiments may also be used to provide minimally invasive percutaneous tissue access, such as for diagnostic or therapeutic access to a solid tissue target (e.g., breast or liver or brain biopsy or tissue excision), delivery of laparoscopic tools or access to bones such as the spine for delivery of screws, bone cement or other tools or implants.

The catheter 10 generally comprises an elongate tubular body 16 extending between a proximal end 12 and a distal functional end 14. The length of the tubular body 16 depends upon the desired application. For example, lengths in the area of from about 120 cm to about 140 cm or more are typical for use in femoral access percutaneous transluminal coronary applications. Intracranial or other applications may call for a different catheter shaft length depending upon the vascular access site, as will be understood in the art.

In the illustrated embodiment, the tubular body 16 is divided into at least a fixed proximal section 33 and an axially extendable and retractable distal section 34 separated at a transition 32. However, the catheter sidewall constructions disclosed herein have applicability in catheters without the use of an extension segment, such as a first single lumen aspiration catheter having a first diameter and optionally a second single lumen aspiration catheter having a second, smaller diameter and greater length than the first catheter so that the second catheter can be advanced through the first catheter.

Simplified method for aspirating a thrombotic occlusion in accordance with present embodiments is described in connection with FIGS. 3A-3F. The steps for aspirating a thrombotic occlusion make use of a transitional guidewire and a transitional guide sheath. The transitional guidewire has a soft and trackable distal segment that can include a smaller diameter guidewire than in other situations so that the transitional guidewire may be advanced deeper. In addition, the transitional guide sheath has a soft and trackable distal segment such that the transitional guide sheath may be advanced deeper than previous guide sheaths. Using a transitional guidewire and a transitional guide sheath that can be advanced to an area near the clot eliminates the need to use a second guidewire or a reperfusion catheter to reach the clot.

Figure 3B:
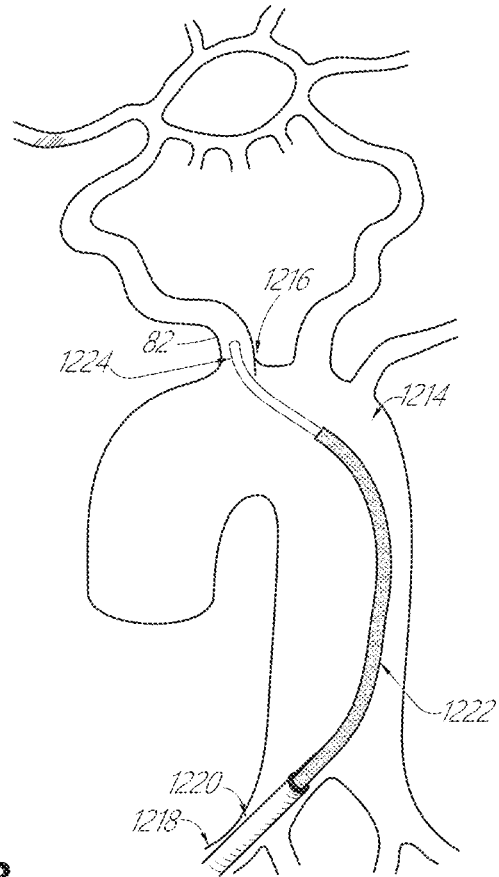

Referring to FIG. 3A, an introducer sheath 1220 is introduced at the femoral artery 1218. The outer diameter of the introducer sheath 1220 may be equal to or less than about 12 F, 11 F, 10 F, 9 F, 8 F, 7 F, or 6 F. Then, a transitional guide sheath 1222 such as the combination access and aspiration catheter discussed in greater detail below is inserted through the introducer sheath 1220 at the femoral artery 1218. The outer diameter of the guide sheath 1222 may be equal to or less than about 9 F, 8 F, 7 F, 6 F, 5 F, 4 F, or 3 F. Referring to FIG. 3B, an insert catheter 1224 is inserted through the transitional guide sheath 1222. The outer diameter of the insert catheter 1224 may be less than about 9 F, 8 F, 7 F, 6 F, 5 F, 4 F, or 3 F, and the inner diameter of the transitional guide sheath 1222 may be greater than the outer diameter of the insert catheter 1224. In some cases, a first guidewire may be introduced through the insert catheter 1224 (not shown in FIG. 3B). The diameter of the proximal section of the first guidewire may be equal to or less than about 0.079", about 0.066", about 0.053", about 0.038", about 0.035", about 0.030", or about 0.013".

The transitional guide sheath 1222, the insert catheter 1224, and optionally the first guidewire are tracked up to the aortic arch 1214. See FIG. 3B. The insert catheter 1224 may be used to select the origin of a vessel. In FIG. 3B, the insert catheter 1224 engages the origin 1216 of the brachiocephalic artery 82. An angiographic run may be performed by injecting contrast media through the insert catheter 1224. In the cases where the first guidewire is used before the angiographic run, the first guidewire may be removed prior to injecting the contrast media.

Figure 3C:
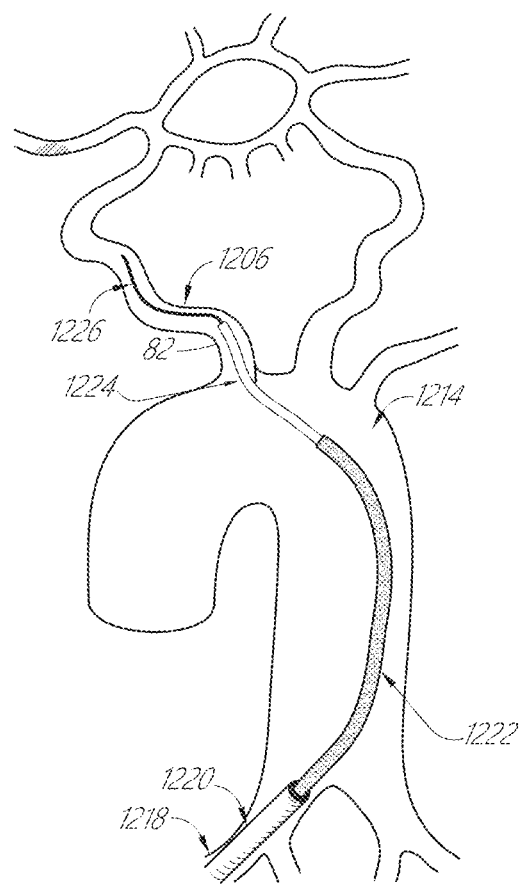
Figure 3D:
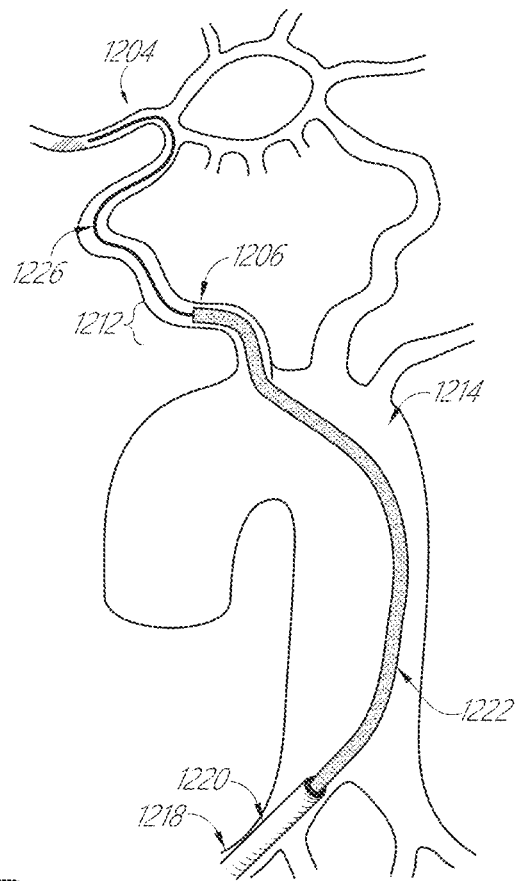

Referring to FIG. 3C, the transitional guidewire 1226 is inserted through the lumen of the insert catheter 1224 or guide sheath 1222. The diameter of at least a portion of the transitional guidewire 1226 (e.g., proximal diameter) is substantially similar to that of the first guidewire 1126. The diameter of at least a portion of the transitional guidewire 1226 (e.g., distal diameter) may be smaller than that of the first guidewire 1126 and may have a diameter along a proximal segment of at least about 0.030" and in some embodiments about 0.038". A transition begins within the range of from about 15 cm to 30 cm from the distal end, and typically no more than about 20 cm or 25 cm from the distal end, distally of which the diameter tapers down to no more than about 0.018" and in some embodiments about 0.016". Referring to FIG. 3D, if utilized, the insert catheter 1224 may be removed because it may be too stiff to be advanced to the MCA 1204. In some embodiments, the transitional guidewire 1226 provides sufficient back up support that the combination access and aspiration catheter 1224 may be advanced directly over the transitional guidewire without any intervening devices. Then, the transitional guidewire 1226 is advanced to the MCA 1204. The transitional guidewire 1226 has a distal segment that has a smaller diameter than that of the first guidewire 1126 described in FIG. 9C. The distal segment of the transitional guidewire 1226 comprises a soft and atraumatic tip and can be tracked to the remote neurovasculature such as the MCA 1204, which is distal to the petrous segment 1212 of the ICA 1206.

Figure 3E:
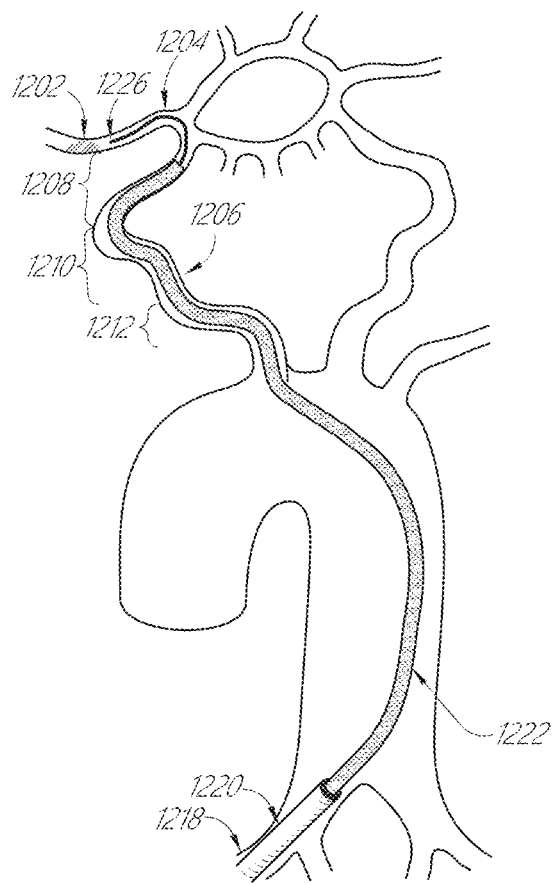

Referring to FIG. 3E, the transitional guide sheath 1222 is advanced to or beyond the cavernous segment 1210 or the cerebral 1208 segment of the ICA 1206. Unlike the guide sheath 1122 described in FIG. 9D, the transitional guide sheath 1222 may be advanced to the cavernous segment 1210 or the cerebral 1208 segment of the ICA 1206 beyond the petrous segment 1212 because the transitional guide sheath 1222 has a soft yet trackable distal segment described in further detail below, for example in connection with FIG. 14. The larger proximal diameter and stiffer body of the transitional guidewire 1226 may provide better support for the transitional guide sheath 1222 to track through the vasculature.

Figure 3F:
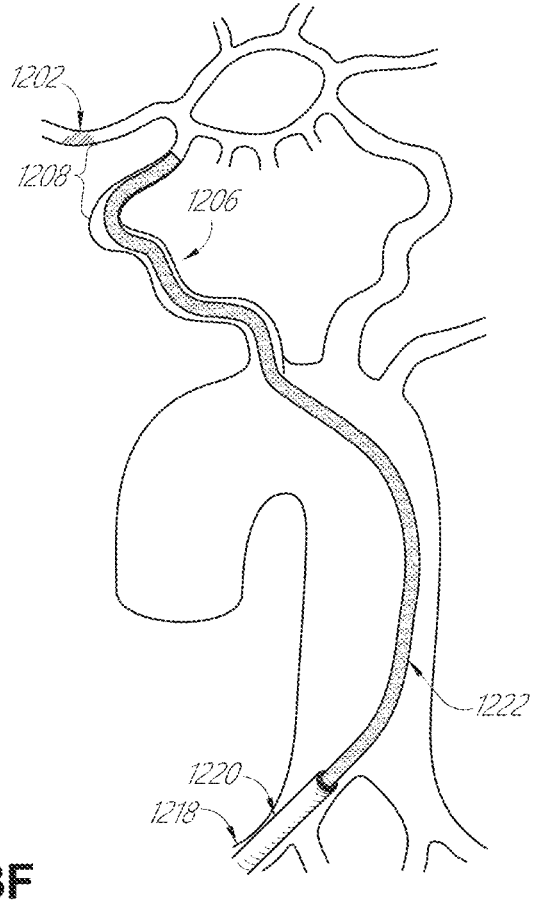

Referring to FIG. 3F, after the transitional guide sheath 1222 is advanced to the cerebral segment 1208 of the ICA 1206, the transitional guidewire 1226 is removed. Then, a vacuum pressure is applied at the proximal end of the transitional guide sheath 1222 to aspirate the occlusion 1202 through the central lumen of the transitional guide sheath 1222. The inner diameter of the transitional guide sheath 1222 may be equal to about or greater than about 0.100", about 0.088", about 0.080", about 0.070", or about 0.060". The inner diameter of the transitional guide sheath 1222 is larger than prior aspiration catheters, which translates to more effective aspiration. The cross-sectional area of the central lumen of the transitional guide sheath 1222 may be almost twice as large as that of the largest aspiration catheter 1128 currently available.

If the guide sheath 1222 is not able to track deep enough into the distal vasculature to reach the occlusion or other desired target site, a telescopic extension segment as discussed elsewhere herein may be introduced into the proximal end of sheath 1222 and advanced distally to extend beyond the distal end of the sheath 1222 and thereby extend the reach of the aspiration system. In some embodiments, the extension segment has an ID of about 0.070".

If thrombotic material is not able to be drawn into the sheath 1222 or extension segment under constant vacuum, pulsatile vacuum may be applied as discussed below. If pulsatile vacuum does not satisfactorily capture the occlusion, an agitator may be advanced through the sheath 1222 and extension segment to facilitate drawing the clot into the central lumen. Additional details of the agitator and its use are disclosed below.

A pulsatile vacuum pressure aspirator may be used in order to improve effectiveness of aspiration for vascular thrombectomy and to improve catheter trackability through tortuous vasculatures. In some embodiments, a pulsatile vacuum pressure aspirator may apply intermittent or pulsatile vacuum to lumen 40 or a lumen of the various embodiments described herein. A pulsatile vacuum pressure aspirator can be in fluid connection with the proximal end 12 of the catheter 10 and comprises one or more of vacuum generator, vacuum chamber, collection canister, solenoid valve, frequency modulator, valve controller, or remote controller.

Figure 4:
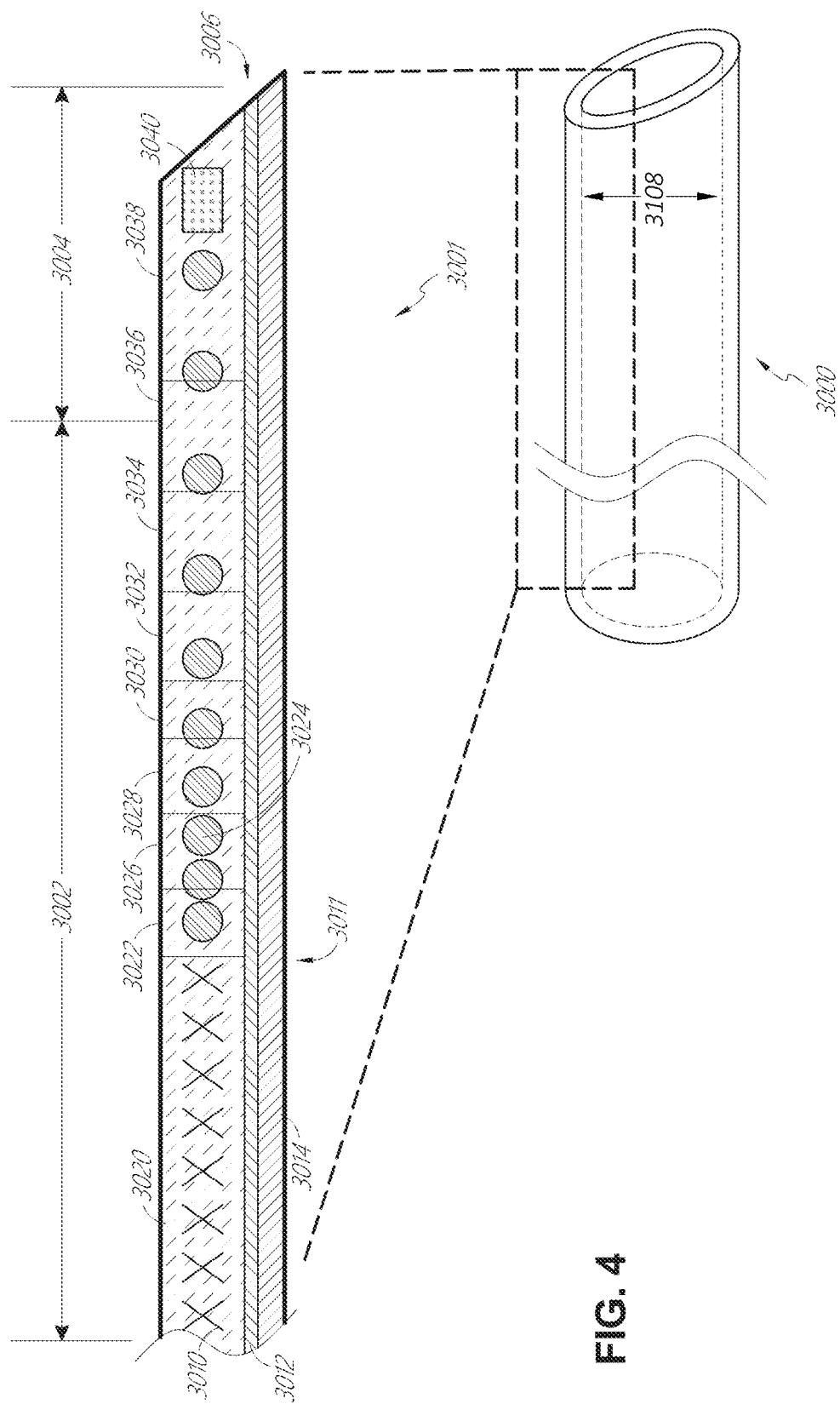
FIG. 4 illustrates a cross-sectional elevational view of a catheter wall according to some embodiments.

In some embodiments, referring to FIG. 4, the catheter 3000 may have an effective length from the manifold to distal tip from about 70 cm to about 150 cm, from about 80 cm to about 140 cm, from about 90 cm to about 130 cm, from about 100 cm to about 120 cm, or from about 105 cm to about 115 cm. The outer diameter of the catheter 3000 may be from about 0.07 inches to about 0.15 inches, from about 0.08 inches to about 0.14 inches, from about 0.09 inches to about 0.13 inches, from about 0.1 inches to about 0.12 inches, or from about 0.105 inches to about 0.115 inches, and may be less in a distal segment than in a proximal segment. The inner diameter 3108 of the catheter 3000 in a single central lumen embodiment may be greater than or equal to about 0.11 inches, greater than or equal to about 0.1 inches, greater than or equal to about 0.09 inches, greater than or equal to about 0.088 inches, greater than or equal to about 0.08 inches, greater than or equal to about 0.07 inches, greater than or equal to about 0.06 inches, or greater than or equal to about 0.05 inches. The inner diameter 3108 of the catheter 3000 in a single central lumen embodiment may be less than or equal to about 0.11 inches, less than or equal to about 0.1 inches, less than or equal to about 0.09 inches, less than or equal to about 0.088 inches, less than or equal to about 0.08 inches, less than or equal to about 0.07 inches, less than or equal to about 0.06 inches, or less than or equal to about 0.05 inches. Referring to FIG. 4, an inner liner 3014 may be formed by dip coating a mandrel (not shown) to provide a thin walled tubular inside layer of the catheter body 3000. The dip coating may be produced by coating a wire such as a silver coated copper wire in PTFE. The mandrel may thereafter be axially elongated to reduce its diameter, and removed to leave the tubular inner liner. The outside surface of the tubular inner liner 3014 may thereafter be coated with a soft tie layer 3012 such as polyurethane (e.g., Tecoflex™), to produce a layer having a thickness of no more than about 0.005 inches, and in some implementations approximately 0.001 inches. The tie layer 3012 will generally extend along at least about the most distal 10 cm or 20 cm of the catheter 3000, generally less than about 50 cm and may in some embodiments extend approximately the distal 30 cm of the catheter 3000.

A braid such as a 75 ppi or 85 ppi stainless steel braid 3010 may thereafter be wrapped around the inner liner 3014 through a proximal zone up to a distal transition 3011. From the distal transition 3011 to the distal end of the catheter 3000, a coil 3024 comprising a shape memory material such as a Nitinol alloy may thereafter be wrapped around the inner liner 3014. In some embodiments, the Nitinol coil has a transition temperature below body temperature so that the Nitinol resides in the austenite (springy/super elastic) state at body temperature. Adjacent loops or filars of the coil may be closely tightly wound in a proximal zone with a distal section having looser spacing between adjacent loops. In embodiments having a coil section 3024 with an axial length of between about 20% and 30% of the overall catheter length, (e.g., 28 cm coil length in a 110 cm catheter 3000), at least the distal 1 or 2 or 3 or 4 cm of the coil will have a spacing that is at least about 130%, and in some implementations at least about 150% or more than the spacing in the proximal coil section. In a 110 cm catheter 3000 having a Nitinol coil the spacing in the proximal coil may be about 0.004 inches or 0.005 inches and in the distal section may be at least about 0.006 inches or 0.007 inches or more. In some implementations, there may be a linear transition in Nitinol coil spacing along a length of the catheter from about 0.005 inches in the proximal coil to about 0.007 inches or more in the distal section of the catheter. For example, the transition may be along a length in the range of between about 0.5 cm to about 1.5 cm; between about 1 cm to about 5 cm; between about 0.5 cm to about 3 cm; between about 2 cm to about 3 cm; preferably about 2.5 cm or preferably about 1 cm.

The distal end of the coil 3024 may be spaced proximally from the distal end of the inner liner 3014 to provide room for an annular radiopaque marker 3040. In some embodiments, the distal end of the catheter 3000 is provided with a beveled distal surface 3006 residing on a plane having an angle of at least about 10° or 20° and in some embodiments about 30° with respect to a longitudinal axis of the catheter 3000. The radiopaque marker 3040 may reside in a plane that is transverse to the longitudinal axis. Alternatively, at least the distally facing edge of the annular radiopaque (RO) marker 3040 may be an ellipse, residing on a plane which is inclined with respect to the longitudinal axis to complement the bevel angle of the distal surface 3006.

After applying the proximal braid 3010, the distal coil 3024 and the RO marker 3040, an outer sleeve or jacket 3020 may be applied such as a shrink wrap tube to enclose the body of catheter 3000. The outer shrink-wrapped sleeve 3020 may comprise any of a variety of materials, such as polyethylene, polyurethane, PEBAX, nylon or others known in the art. In some embodiments, the outer shrink-wrapped sleeve or jacket 3020 may comprise a hydrophilic material. Sufficient heat is applied to cause the polymer to flow into and embed the proximal braid and distal coil.

In some embodiments, the outer shrink wrap jacket 3020 is formed by sequentially advancing a plurality of short tubular segments 3022, 3026, 3028, 3030, 3032, 3034, 3036, 3038 concentrically over the catheter shaft subassembly, and applying heat to shrink the sections on to the catheter 3000 and provide a smooth continuous outer tubular body. The foregoing construction may extend along at least the most distal 10 cm, and in some embodiments at least about the most distal 20 or 25 cm of the catheter 3000.

The durometer of the outer wall segments may decrease in a distal direction. For example, proximal segments such as 3022 and 3026 may have a durometer of at least about 60 or 70 D, with gradual decrease in durometer of successive segments in a distal direction to a durometer of no more than about 35 D or 25 D or lower. A 25 cm section may have at least about 3 or 5 or 7 or more segments and the catheter 3000 overall may have at least about 6 or 8 or 10 or more distinct flexibility zones. The distal 1 or 2 or 4 or more segments 3036, 3038, may have a smaller OD following shrinking than the more proximal segments 3022-3034 to produce a step down in OD for the finished body of catheter 3000. The length of the smaller OD section 3004 may be within the range of from about 3 cm to about 15 cm and in some embodiments is within the range of from about 5 cm to about 10 cm such as about 7 cm or 8 cm, and may be accomplished by providing the distal segments 3036, 3038 with a smaller wall thickness.

Figure 5A:
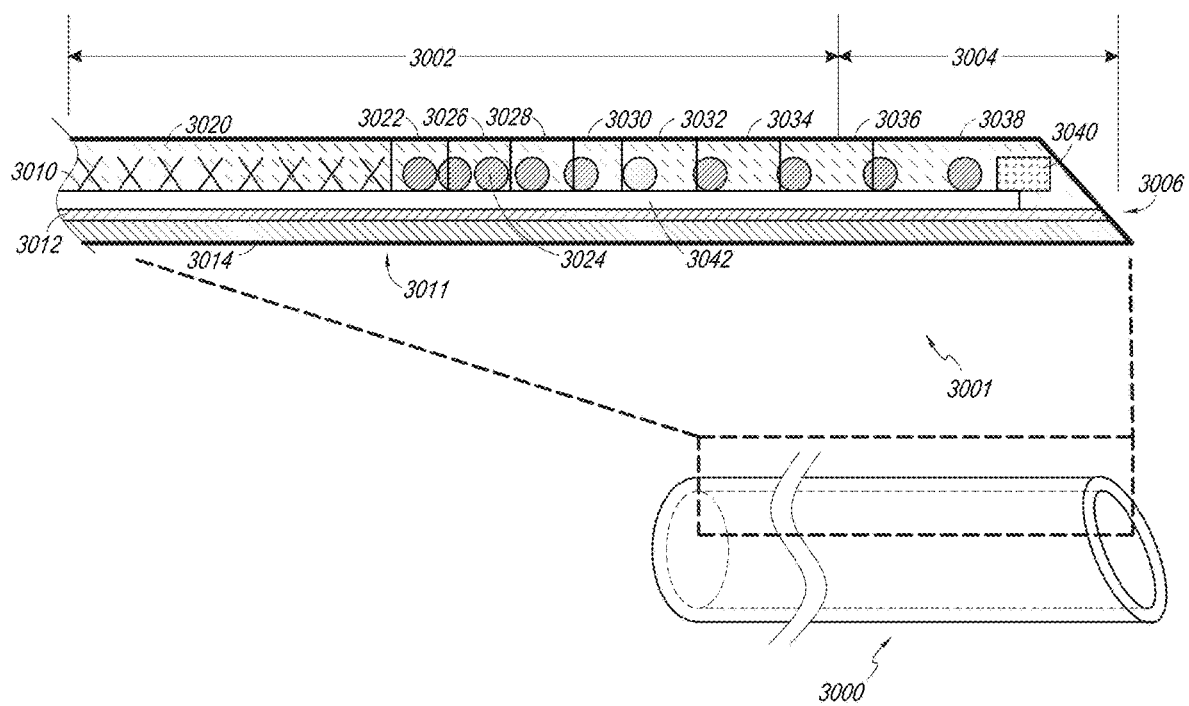
FIG. 5A illustrates a cross-sectional elevational view of a catheter wall according to some embodiments, showing one or more axially extending filaments.
Figure 5B:
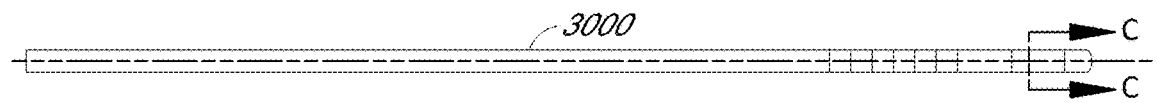
FIG. 5B describes a side elevational view of the catheter of FIG. 5A
Figure 5C:
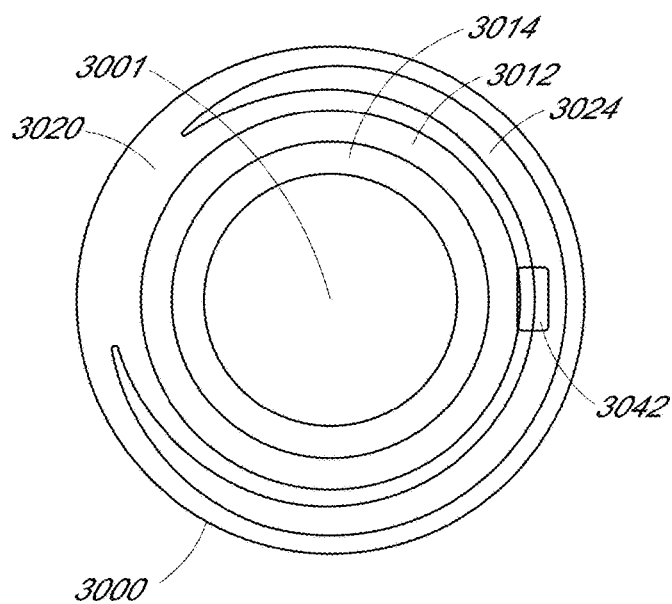
FIG. 5C illustrates a cross-sectional view taken along the line C-C of FIG. 5B, showing one or more axially extending filaments.

Referring to FIGS. 5A-5C, the catheter may further comprise a tension support for increasing the tension resistance in the distal zone. The tension support may comprise a filament and, more specifically, may comprise one or more axially extending filaments 3042. The one or more axially extending filaments 3042 may be axially placed inside the catheter wall near the distal end of the catheter. The one or more axially extending filaments 3042 serve as a tension support and resist elongation of the catheter wall under tension (e.g., when the catheter is being proximally retracted through tortuous vasculature). At least one of the one or more axially extending filaments 3042 may proximally extend along the length of the catheter wall from near the distal end of the catheter to less than about 5 cm from the distal end of the catheter, less than about 10 cm from the distal end of the catheter, less than about 15 cm from the distal end of the catheter, less than about 20 cm from the distal end of the catheter, less than about 25 cm from the distal end of the catheter, less than about 30 cm from the distal end of the catheter, less than about 35 cm from the distal end of the catheter, less than about 40 cm from the distal end of the catheter, or less than about 50 cm from the distal end of the catheter. The one or more axially extending filaments 3042 may have a length greater than or equal to about 50 cm, greater than or equal to about 40 cm, greater than or equal to about 35 cm, greater than or equal to about 30 cm, greater than or equal to about 25 cm, greater than or equal to about 20 cm, greater than or equal to about 15 cm, greater than or equal to about 10 cm, or greater than or equal to about 5 cm. At least one of the one or more axially extending filaments 3042 may have a length less than or equal to about 50 cm, less than or equal to about 40 cm, less than or equal to about 35 cm, less than or equal to about 30 cm, less than or equal to about 25 cm, less than or equal to about 20 cm, less than or equal to about 15 cm, less than or equal to about 10 cm, or less than or equal to about 5 cm. At least one of the one or more axially extending filaments 3042 may extend at least about the most distal 50 cm of the length of the catheter, at least about the most distal 40 cm of the length of the catheter, at least about the most distal 35 cm of the length of the catheter, at least about the most distal 30 cm of the length of the catheter, at least about the most distal 25 cm of the length of the catheter, at least about the most distal 20 cm of the length of the catheter, at least about the most distal 15 cm of the length of the catheter, at least about the most distal 10 cm of the length of the catheter, or at least about the most distal 5 cm of the length of the catheter.

The one or more axially extending filaments 3042 may be placed near or radially outside the tie layer 3012 or the inner liner 3014. The one or more axially extending filaments 3042 may be placed near or radially inside the braid 3010 and/or the coil 3024. The one or more axially extending filaments 3042 may be carried between the inner liner 3014 and the helical coil 3024.

When more than one axially extending filaments 3042 are placed in the catheter wall, the axially extending filaments 3042 may be placed in a radially symmetrical manner. For example, the angle between the two axially extending filaments 3042 with respect to the radial center of the catheter may be about 180 degree. Alternatively, depending on desired clinical performances (e.g., flexibility, trackability), the axially extending filaments 3042 may be placed in a radially asymmetrical manner. The angle between any two axially extending filaments 3042 with respect to the radial center of the catheter may be less than about 180 degree, less than or equal to about 165 degree, less than or equal to about 150 degree, less than or equal to about 135 degree, less than or equal to about 120 degree, less than or equal to about 105 degree, less than or equal to about 90 degree, less than or equal to about 75 degree, less than or equal to about 60 degree, less than or equal to about 45 degree, less than or equal to about 30 degree, less than or equal to about 15 degree, less than or equal to about 10 degree, or less than or equal to about 5 degree.

The one or more axially extending filaments 3042 may be made of materials such as Kevlar, Polyester, Meta-Para-Aramide, or any combinations thereof. At least one of the one or more axially extending filaments 3042 may comprise a single fiber or a multi-fiber bundle, and the fiber or bundle may have a round, rectangular, or other cross-sectional shape. The terms fiber or filament do not convey composition, and they may comprise any of a variety of high tensile strength polymers, metals or alloys depending upon design considerations such as the desired tensile failure limit and wall thickness. The cross-sectional dimension of the one or more axially extending filaments 3042, as measured in the radial direction, may be no more than about 1%, 2%, 3%, 4%, 5%, 6%, 7%, 8%, 9%, 10%, 11%, 12%, 13%, 14%, 15%, 20%, 25%, or 30% of that of the catheter 3000. The cross-sectional dimension of the one or more axially extending filaments 3042, as measured in the radial direction, may be no more than about 0.001 inches, about 0.002 inches, about 0.003 inches, about 0.004 inches, about 0.005 inches, about 0.006 inches, about 0.007 inches, about 0.008 inches, about 0.009 inches, about 0.010 inches, about 0.015 inches, about 0.020 inches, about 0.025 inches, or about 0.030 inches.

The one or more axially extending filaments 3042 may increase the tensile strength of the distal zone of the catheter to at least about 1 pound, at least about 2 pounds, at least about 3 pounds, at least about 4 pounds, at least about 5 pounds, at least about 6 pounds, at least about 7 pounds, at least about 8 pounds, or at least about 10 pounds or more.

Figure 6A:
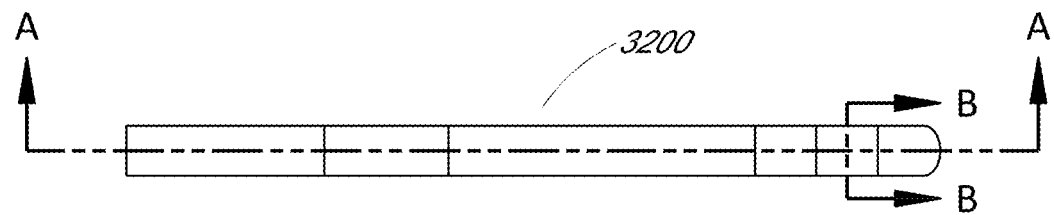
FIG. 6A depicts a side elevational view of a catheter according to some embodiments.
Figure 6B:
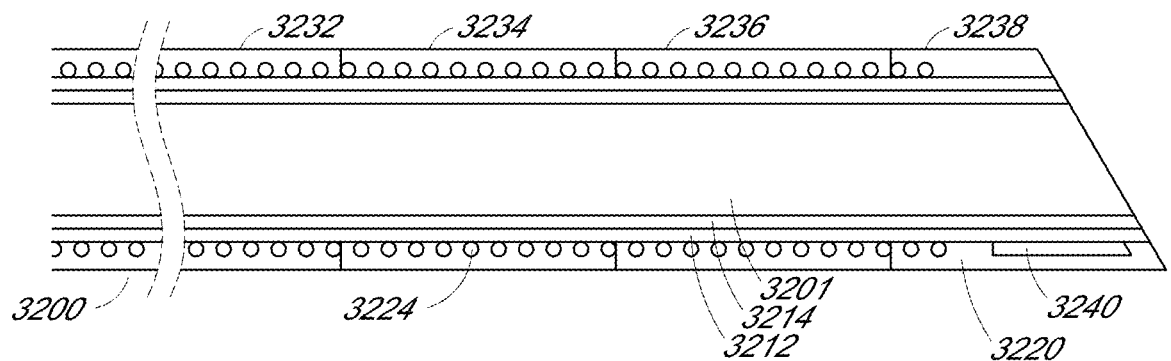
FIG. 6B describes a cross-sectional elevational view taken along the line A-A of FIG. 6A.
Figure 6C:
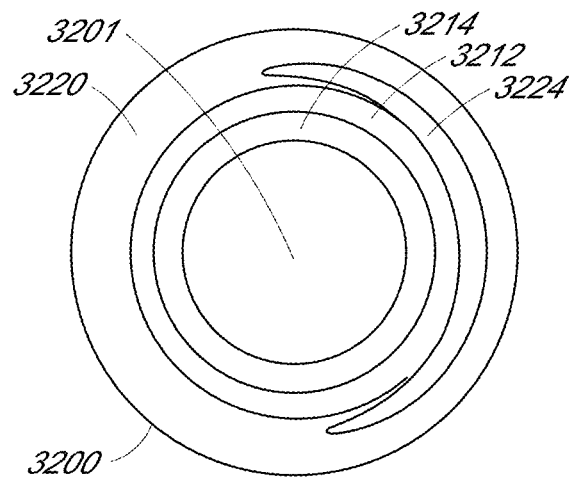
FIG. 6C illustrates a cross-sectional view taken along the line B-B of FIG. 6A.

Referring to FIGS. 6A-6C, depending on whether the catheter 3000 is able to navigate sufficiently distally to reach the target site, an intraluminal catheter 3200 such as a telescopic extension segment having a proximally extending control wire as has been described elsewhere herein may be inserted through the catheter 3000 from the proximal end of the catheter 3000. The intraluminal catheter 3200 is inserted such that the distal end of the intraluminal catheter 3200 reaches further distally beyond the distal end of the catheter 3000. The outer diameter of the intraluminal catheter 3200 is smaller than the inner diameter of the catheter 3000. This way, the intraluminal catheter 3200 can slide inside the lumen of the catheter 3000.

The intraluminal catheter 3200 incorporates characteristics of the side wall construction of the catheter 3000 described herein. The axial length of the tubular extension segment may be less than about 50% and typically less than about 25% of the length of the catheter 3000. The axial length of the tubular extension segment will generally be at least about 10 cm or 15 cm or 20 cm or 25 cm or more but generally no more than about 70 cm or 50 cm or 30 cm.

Figure 7A:
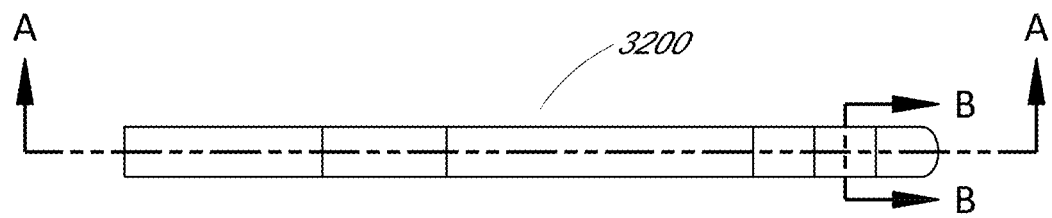
FIG. 7A depicts a side elevational view of a catheter according to some embodiments.
Figure 7B:
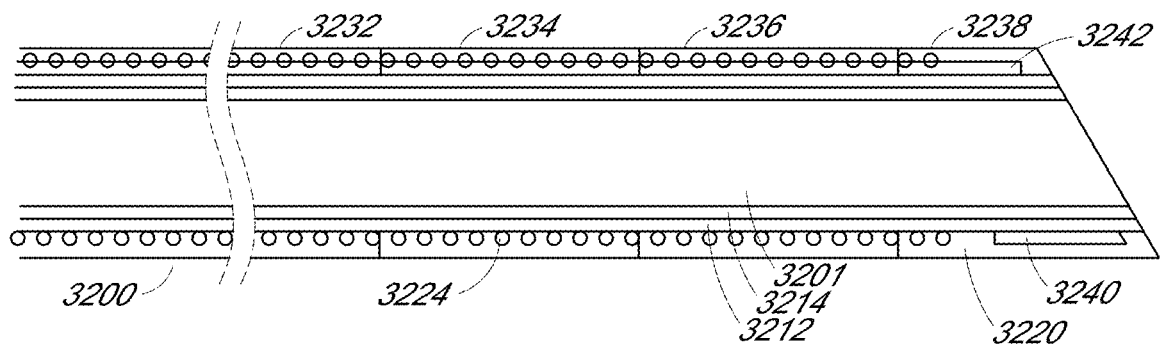
FIG. 7B describes a cross-sectional elevational view taken along the line A-A of FIG. 7A, showing one or more axially extending filaments.
Figure 7C:
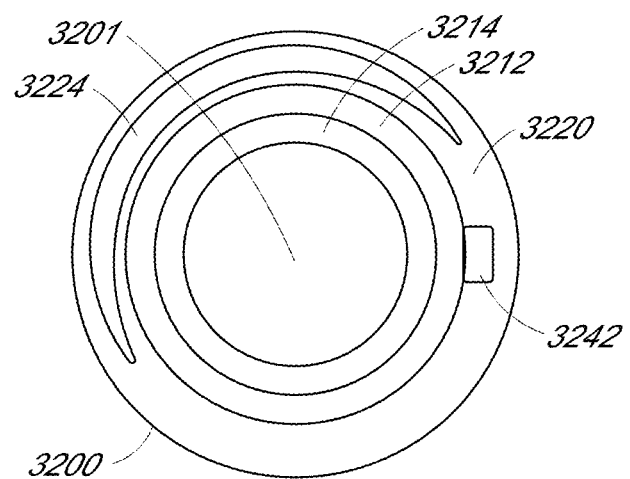
FIG. 7C illustrates a cross-sectional view taken along the line B-B of FIG. 7A, showing one or more axially extending filaments.

Referring to FIGS. 7A-7C, the intraluminal catheter 3200 may have one or more axially extending filaments 3242. The one or more axially extending filaments 3242 incorporate characteristics of the one or more axially extending filaments 3042 of the catheter 3000, except the cross-sectional dimension as measured in the radial direction of the one or more axially extending filaments 3242 of the intraluminal catheter 3200 may be less than the corresponding dimension of the filament 3042 in the catheter 3000.

Referring to FIGS. 8A-8B, there is illustrated one example of an outer jacket segment stacking pattern for a progressive flexibility catheter of the type discussed in connection with FIG. 4. A distal segment 3038 may have a length within the range of about 1-3 cm, and a durometer of less than about 35 D or 30 D. An adjacent proximal segment 3036 may have a length within the range of about 4-6 cm, and a durometer of less than about 35 D or 30 D. An adjacent proximal segment 3034 may have a length within the range of about 4-6 cm, and a durometer of about 35 D or less. An adjacent proximal segment 3032 may have a length within the range of about 1-3 cm, and a durometer within the range of from about 35 D to about 45 D (e.g., 40D). An adjacent proximal segment 3030 may have a length within the range of about 1-3 cm, and a durometer within the range of from about 50 D to about 60 D (e.g., about 55 D). An adjacent proximal segment 3028 may have a length within the range of about 1-3 cm, and a durometer within the range of from about 35 D to about 50 D to about 60 D (e.g., about 55 D). An adjacent proximal segment 3026 may have a length within the range of about 1-3 cm, and a durometer of at least about 60 D and typically less than about 75 D. More proximal segments may have a durometer of at least about 65 D or 70 D. The distal most two or three segments may comprise a material such as Tecothane, and more proximal segments may comprise PEBAX or other catheter jacket materials known in the art. At least three or five or seven or nine or more discrete segments may be utilized, having a change in durometer between highest and lowest along the length of the catheter shaft of at least about 10 D, preferably at least about 20 D and in some implementations at least about 30 D or 40 D or more.

Figure 26:
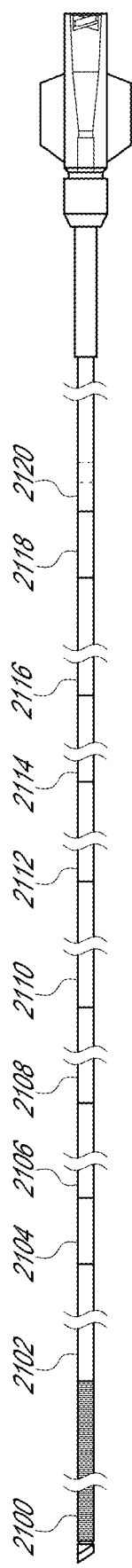
FIG. 26 illustrates a side elevational view of a progressively enhanced flexibility catheter according to some embodiments.

Referring to FIG. 26, there is illustrated another example of an outer jacket segment stacking pattern for a progressive flexibility catheter of the type discussed in connection with FIG. 4. A distal segment 2100 may have a length within the range of about 0.5 cm to about 3 cm, and a durometer of less than about 35 D or 30 D. An adjacent proximal segment 2102 may have a length within the range of about 4-6 cm, and a durometer of less than about 35 D or 30 D. An adjacent proximal segment 2104 may have a length within the range of about 1 cm to about 3 cm, and a durometer of about 35 D or less (e.g., about 25 D). An adjacent proximal segment 2106 may have a length within the range of about 1 cm to about 3 cm or about 1 cm to about 5 cm, and a durometer within the range of from about 30 D to about 45 D (e.g., about 35 D or about 37 D or about 40 D). An adjacent proximal segment 2108 may have a length within the range of about 1 cm to about 3 cm, and a durometer within the range of from about 35 D to about 50 D or about 40 D to about 55 D (e.g., about 40 D or about 47 D). An adjacent proximal segment 2110 may have a length within the range of about 1 cm to about 3 cm, and a durometer within the range of from about 40 D to about 50 D to about 55 D or about 60 D (e.g., about 47 D or about 55 D). An adjacent proximal segment 2112 may have a length within the range of about 1 cm to about 20 cm or about 10 cm to about 20 cm, and a durometer of at least about 35 D to about 50 D to about 60 D or about 65 D (e.g., about 55 D or about 59 D). An adjacent proximal segment 2114 may have a length within the range of about 1 cm to about 3 cm or about 2 to about 4 cm, and a durometer of at least about 60 D and typically less than about 75 D (e.g., about 63 D). An adjacent proximal segment 2116 may have a length within the range of about 1 cm to about 3 cm or about 2 cm to about 4 cm, and a durometer of at least about 65 D and typically less than about 80 D (e.g., about 72 D). More proximal segments may have a durometer of at least about 65 D or about 70 D. Any one or more of the foregoing intervening segments may be omitted as desired, depending upon the desired performance.

The distal most two or three segments may comprise a material such as Tecothane, and more proximal segments may comprise PEBAX, a Vestamid blend, or other catheter jacket materials known in the art. At least three or five or seven or nine or more discrete segments may be utilized, having a change in durometer between highest and lowest along the length of the catheter shaft of at least about 5 D or at least about 10 D or between about 3D to about 10 D, preferably at least about 20 D and in some implementations at least about 30 D or 40 D or more.

In any of the embodiments described herein, for example such as those of FIGS. 8A-8B and FIG. 26, one or more proximal segments may be further reinforced by including a coil under the braid. For example, the spacing between adjacent filars in the coil under the braid may be within the range of from about 0.003" to about 0.010" such as about 0.004 inches or about 0.005 inches or about 0.006 inches. The coil may be formed of stainless steel, Nitinol, or other materials known to one of skill in the art. The coil under the braid in one or more proximal segments increases pushability and kink resistance of the catheter.

Figure 27A:
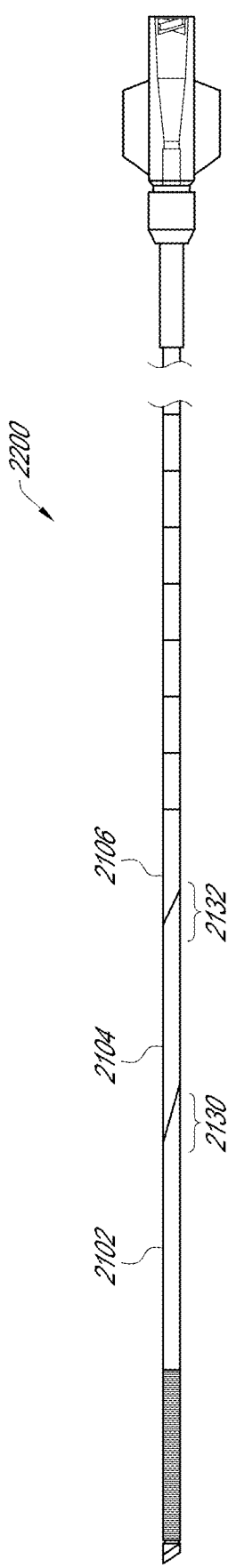
FIG. 27A illustrates a side elevational view of various configurations of distal one or more transition zones according to some embodiments.
Figure 27B:
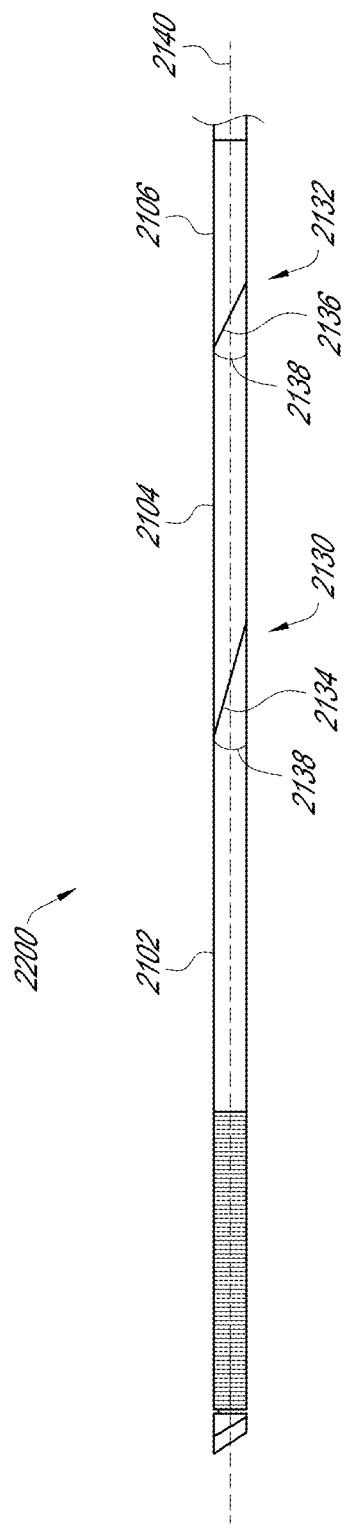
FIG. 27B illustrates a distal end view of the embodiment of FIG. 27A.

In any of the embodiments described herein, for example such as those of FIGS. 8A-8B and FIG. 26, one or more transition zones 2130, 2132 between adjacent segments, for example segments 2102-2104, and 2104-2106 shown in FIGS. 27A-27B, may comprise an inclined junction between a proximal and adjacent distal segment. The adjacent surfaces are thus complementary inclined faces on adjacent cut cylinder shaped segments, rotationally offset from each other to form a seamless tube.

The inclined distal surfaces 2134, 2136 thus reside on a plane having an angle 2138 of at least about 10° or about 15° and in some embodiments at least about 20° but generally no more than about 80° or 65° with respect to a longitudinal axis 2140 of the catheter 2200. The angle 2138 of the inclined distal surfaces 2134, 2136 may be in the range of between about 10° to about 45°; about 5° to about 30°; approximately about 15° or about 25°. The inclined proximal surface of the adjacent segment may be inclined at the same angles as described above for the distal surfaces. In a particular transition, the complementary inclined surfaces will have the same inclined angle. The edge of the tubular sidewall at the inclined surfaces of transition zones 2130, 2132 form an ellipse, residing on a plane which is inclined with respect to the longitudinal axis 2140

In the illustrated embodiment, relatively distal segment 2102 has an inclined proximal face and a transverse (substantially perpendicular to the longitudinal axis) distal face. Complementary segment 2104 has an inclined distal face. The proximal face on segment 2104 is illustrated as inclined because this is a two inclined transition zone embodiment with only a single segment in between. However it may alternatively be transverse depending upon the desired spacing and sidewall construction between the 1st and 2nd inclined junctions. There may be at least one or two or five or more segments having two transverse segment ends in between the first and second inclined injunctions depending upon the desired flexibility profile. Generally all segments proximal to segment 2106 having the proximal inclined junction will have two transverse junctions and there may be at least five or eight or ten or more such segments.

In some embodiments, the axial length of the inclined junction may be in the range of between about 0.4 cm to about 1.0 cm or 1.5 cm. In one implementation, the distal transition 2130 is inclined at an angle of about 15 degrees and has an axial length of about 0.8 centimeters. The proximal transition 2132 is inclined at an angle of about 25 degrees and has an axial length of about 0.6 cm.

The axial length of distal segment 2102 is at least about 10 millimeters or at least about 20 millimeters and generally no more than about 50 mm or 40 millimeters. In one implementation, the axial length is between about 15 millimeters and 45 millimeters. The axial length of proximal segment 2104 is at least about 10 millimeters or at least about 20 millimeters and generally no more than about 50 millimeters or 40 millimeters. In one implementation the axial length of proximal segment 2104 is between about 25 millimeters and about 35 millimeters. In one implementation the first distal segment 2102 is longer than the first proximal segment 2104. The first proximal segment 2104 may have a smaller outside diameter than the next adjacent proximal segment 2106.

In one implementation, the catheter includes a proximal inclined junction and a distal inclined junction. The distance between the proximal and distal inclined junctions may be within the range of from about 10 millimeters to about 50 millimeters or within the range of from about 25 millimeters to about 35 millimeters. In one implementation, the distance is about 30 millimeters. The catheter sidewall between the proximal inclined junction and distal inclined junction may be formed from at least one or two or three or more individual segments. In one implementation, the proximal inclined junction and distal inclined junction are separated by a single tubular segment having an inclined proximal face and an inclined distal face. The angles of inclination of the proximal and distal inclined faces may be the same, or maybe dissimilar. The distal inclined junction may be inclined at a smaller angle than the proximal inclined junction. In one implementation, the distal inclined face is inclined at an angle of about 15 degrees from the longitudinal axis, and the proximal inclined face is inclined at an angle of about 25 degrees with respect to the longitudinal axis.

Figure 27C:
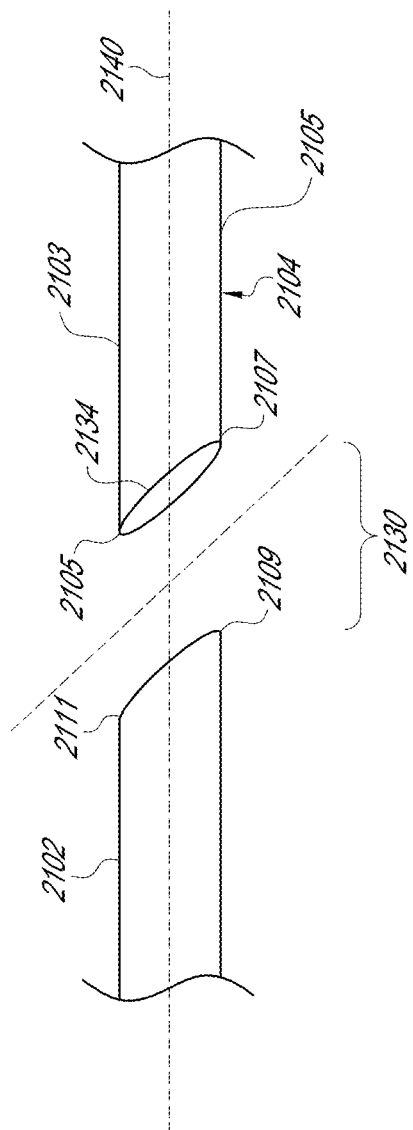
FIG. 27C illustrates an exploded view of an adjacent distal segment and proximal segment about a transition zone of a progressively enhanced flexibility catheter.

Referring to FIG. 27C, there is illustrated an exploded view of adjacent distal segment 2102 and proximal segment 2104. Distal inclined surface 2134 on proximal segment 2104 extends between a distal acute vertex 2105 at the intersection of the distal surface 2134 and long sidewall 2103, and a proximal obtuse vertex 2107 formed at the intersection of the distal surface 2134 and second, opposing short sidewall 2105. The proximal obtuse vertex 2107 is spaced axially proximally apart from the distal acute vertex 2105 by a distance corresponding to the angle of inclination and the diameter of the catheter shaft.

The proximal obtuse vertex 2107 is rotationally aligned with a complementary proximal acute vertex 2109 on distal segment 2102. Similarly, the distal acute vertex 2105 is rotationally aligned with the proximal obtuse vertex 2111 on distal segment 2102. The adjacent segments can thus nest together and upon heating above the softening point of the respective opposing dissimilar polymeric segments form a seamless tubular body having graduated bending characteristics along its length.

Successive inclined transition zones along the length of the catheter body can have a uniform rotational alignment. For example, all successive proximal obtuse vertexes on inclined end faces can be rotationally aligned along a single axial line. Alternatively, the rotational orientation of each successive transition zone can be rotationally offset such as by 90 degrees or 180 degrees or other angle depending upon the desired bending characteristics.

Figure 27D:
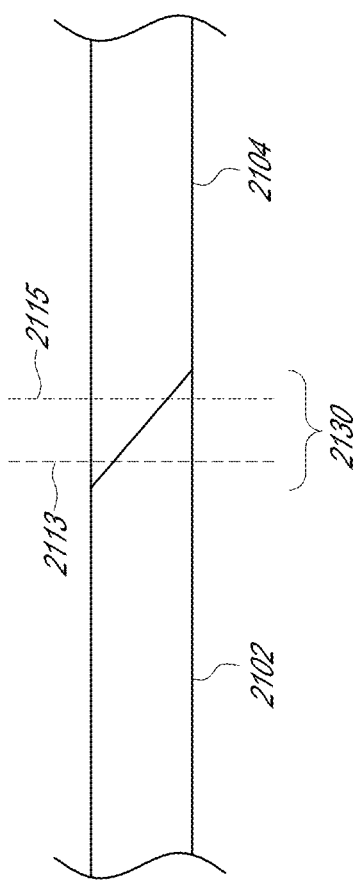
FIG. 27D illustrates a side wall composition of a cross section taken through the transition zone of a progressively enhanced flexibility catheter.
Figure 27E:
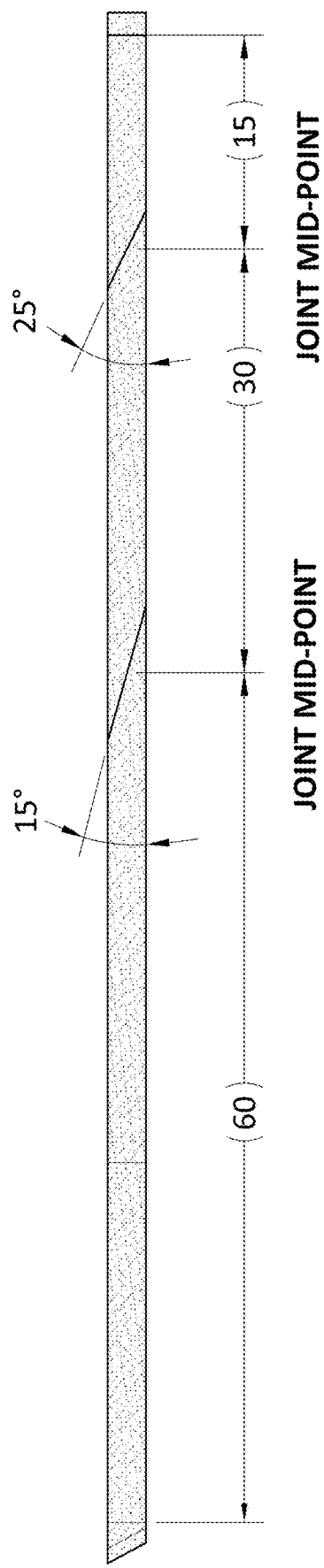
FIG. 27E is a side elevational view of a distal portion of the catheter shown in FIG. 27B

Referring to FIG. 27D, the side wall composition of a cross section 2113 taken through the transition zone 2130 distally of the axial midpoint of the transition zone 2130 will be a blend primarily of the composition of distal segment 2102. Similarly, the composition of a cross section 2115 taken through the transition zone 2130 proximally of the midpoint of the transition zone 2130 will be a blend primarily of the composition of the proximal segment 2104. The composition of a cross section through the midpoint of the transition zone 2130 will be a 50:50 blend of the materials of the two adjacent segments, The resulting catheter transition zone thus exhibits a seamless graduated transition in the ratio of the different polymers or durometer of a first segment and complementary second segment and corresponding graduated transition in the resulting flexibility characteristics across the transition zone 2130 from the first durometer of proximal segment 2104 to the second durometer of distal segment 2102.

Typically the outer jacket segments decrease in durometer in a distal direction. For example the durometer of segment 2106 maybe at least about 70 A or 74 A. The durometer of distally adjacent segment 2104 may also be at least about 70 A or 74 A, having a slightly smaller outside diameter as a result of a slightly smaller wall thickness. The inside diameter of the central lumen remains substantially constant throughout. The durometer of distally adjacent segment 2102 is preferably less than 78 A and maybe no more than about 62 A. The durometer of the next adjacent segment proximal to segment 2106 may be at least about 3533 D. A proximal most segment on the catheter shaft may have a durometer of at least about 6333 D or at least about 7233 D.

At least one or two or four or more inclined junctions as described above can be included on any of the catheter shafts disclosed herein. For example, the catheter shaft may include a coil embedded in the sidewall extending proximally from the distal marker band at least about 100 millimeters and in some embodiments at least about 150 millimeters or 200 millimeters. The axially extending tensile element described previously herein may also be provided in the sidewall. Typically, the tensile element will reside beneath the coil, and be secured to the marker band as previously described. The tensile element may extend proximally from the marker band for at least about 100 mms, in some embodiments at least about 150 millimeters or 200 millimeters.

Thus, the distal coil and tensile element preferably extend proximally beyond the inclined transition zones 2130 and 2132. In some implementations, the distal coil comprises stainless steel. The proximal end of the distal stainless steel coil may overlap with the distal end of a proximal coil. The proximal coil may extend to the hub at the proximal end of the catheter shaft, and may comprise stainless steel or nitinol. The length of the overlap between the distal and proximal coils maybe at least about 2 or four or six millimeters but typically less than about 50 or 30 millimeters. The distal coil and proximal coil may be intertwined throughout the length of the overlap.

The catheter shaft may also include a tubular braid surrounding the proximal coil and beneath the polymer jacket, and extending distally from the hub. The braid may extend distally to within about one or two or five centimeters of the proximal end of the distal coil. In one implementation, the distal end of the braid terminates approximately at the proximal end of the distal coil so that the braid does not overlap the intertwined section of the proximal and distal coils. In one implementation, the distal end of the braid ends at the proximal end of the distal coil since the wire diameter of the Niti coil is slightly larger than the stainless steel coil. The braid may be a 32 wire, 1 over 2 under 2 herringbone pattern, 80-90 PPI.

Figure 9:
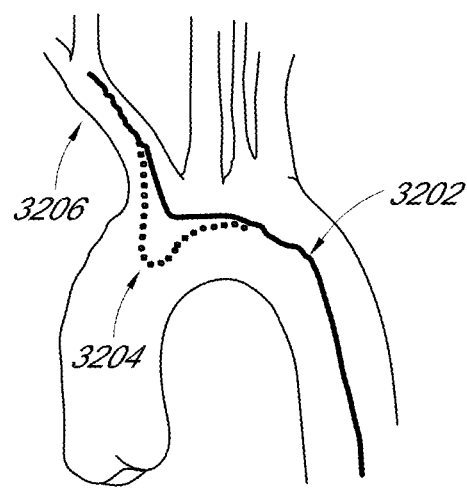
FIG. 9 illustrates back-up support of the catheter in accordance with some embodiments.

Performance metrics of a catheter include back-up support, trackability, pushability, and kink resistance. Back-up support means ability of the catheter to remain in position within anatomy and provide a stable platform through which endoluminal devices may advance. Referring to FIG. 9, when the devices are pushed through the catheter 3202, if there is not enough back-up support in the catheter 3202, the distal portion 3204 of the catheter 3202 may prolapse, pull out, or back out of a vessel 3206 that branches out of a main blood vessel (e.g., brachiocephalic artery 82, common carotid artery 80, or subclavian artery 84). Back-up support for the catheter 3202 may be improved by providing a proximal region with high durometer or modulus and a distal region with low durometer or modulus. Durometer or modulus of the proximal region of the catheter 3202 may be improved by braid reinforcement. The region of the catheter at which durometer or modulus is strengthened may be placed near branching points at which the aortic arch 1114, 1214 branches into brachiocephalic artery 82, common carotid artery 80, or subclavian artery 84 or near other anatomical structures (i.e., branching points) at which a main vessel branches into one or more smaller vessels, providing an opportunity for a catheter with poor back-up support to prolapse. For example, the region of the catheter at which durometer or modulus is strengthened may be placed within about 0.5 cm, about 1 cm, about 2 cm, about 3 cm, about 4 cm, about 5 cm, or about 6 cm from a branching point at which a main vessel branches into one or more smaller vessels.

Trackability means ability of the catheter to track further distally than other catheters (e.g., to M1). For example, a catheter that can reach a cerebral segment of the internal carotid artery (ICA) has better trackability than a catheter that can reach a cavernous or petrous segment of the ICA. Trackability of the catheter may be improved by using a catheter wall with low durometer or modulus or by adding a coating (e.g., a hydrophilic coating) on at least a portion of the catheter wall. In some embodiments, the hydrophilic coating may be placed along the distal most region of the catheter. The hydrophilic coating on the catheter may extend to about 1 cm, about 5 cm, about 10 cm, about 15 cm, or about 20 cm from the distal end of the catheter. The region with lower durometer or modulus may locate at the distal most region of the catheter. The region with lower durometer or modulus may extend to about 1 cm, about 5 cm, about 10 cm, about 15 cm, or about 20 cm from the distal end of the catheter.

Pushability means rigidity of the catheter sufficient to push through anatomy without "buckling". Pushability of the catheter may be improved by increasing its durometer or modulus. Pushability of the catheter may also be improved by providing a proximal region with high durometer or modulus and a distal region with low durometer or modulus. A transition region of the catheter in which durometer or modulus changes along its longitudinal length (e.g., decreasing durometer or modulus from the proximal end to the distal end) may begin at about 50%, 60%, 70%, 75%, 80%, or more of the length of the catheter from its proximal end.

Kink resistance means resistance of the catheter to kinking. In addition, if the catheter does kink, kink resistance of the catheter helps it return to its original shape. Kink resistance is important in the distal segment of the catheter, which is more prone to kinking than the proximal segment. Kink resistance of the catheter may be improved by adding one or more NiTi coils (or a coil at least a portion of which is Nitinol) to the catheter wall.

Figure 10:
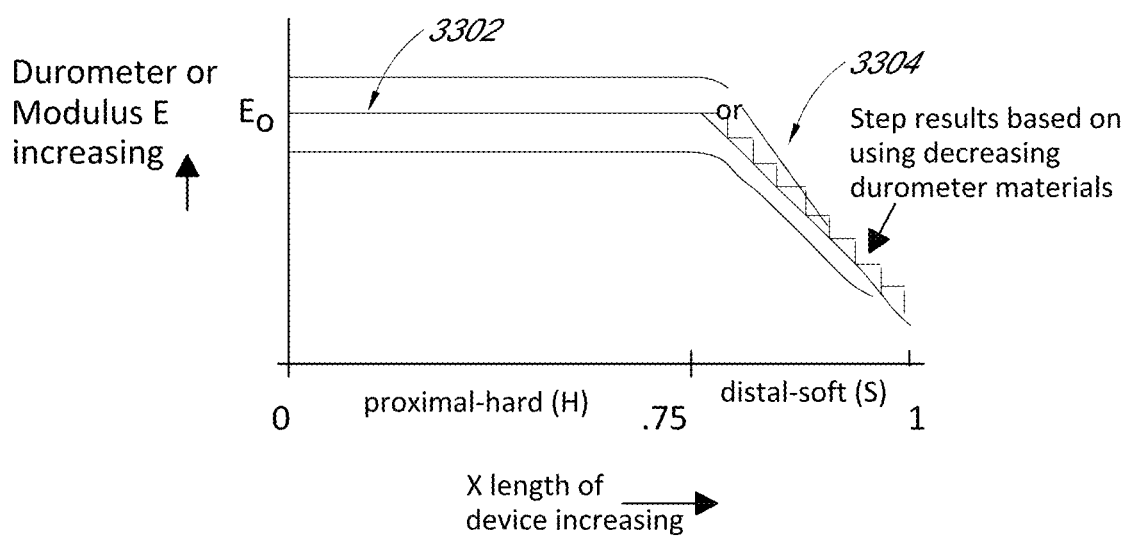
FIG. 10 depicts a graph of modulus or durometer of the catheter along the length of the catheter, from the proximal end to the distal end.

FIG. 10 describes a graph of durometer or modulus of a catheter in accordance with the embodiments herein along the length of the catheter, from the proximal end (x=0) to the distal end (x=1). The catheter according to some embodiments may have a decreasing durometer or modulus (E) approaching its distal end. The proximal end of the catheter has higher durometer or modulus than that of the distal end of the catheter. High durometer or modulus near the proximal end provides superior back-up support of the catheter. Durometer or modulus of the catheter is substantially constant along its length near the proximal end 3302 of the catheter. Then, durometer or modulus of the catheter decreases near the distal end 3304 of the catheter. Durometer or modulus of the catheter may begin to decrease (i.e., transition region) at about 50%, 70%, 75%, 80%, or 90% of the length of the catheter from its proximal end. The catheter may have successively decreasing durometer or modulus near its distal end by using materials with less durometer or modulus, having a thinner catheter wall near the distal end, or both. Decreased durometer or modulus near the distal end provides superior trackability of the catheter.

Figure 11:
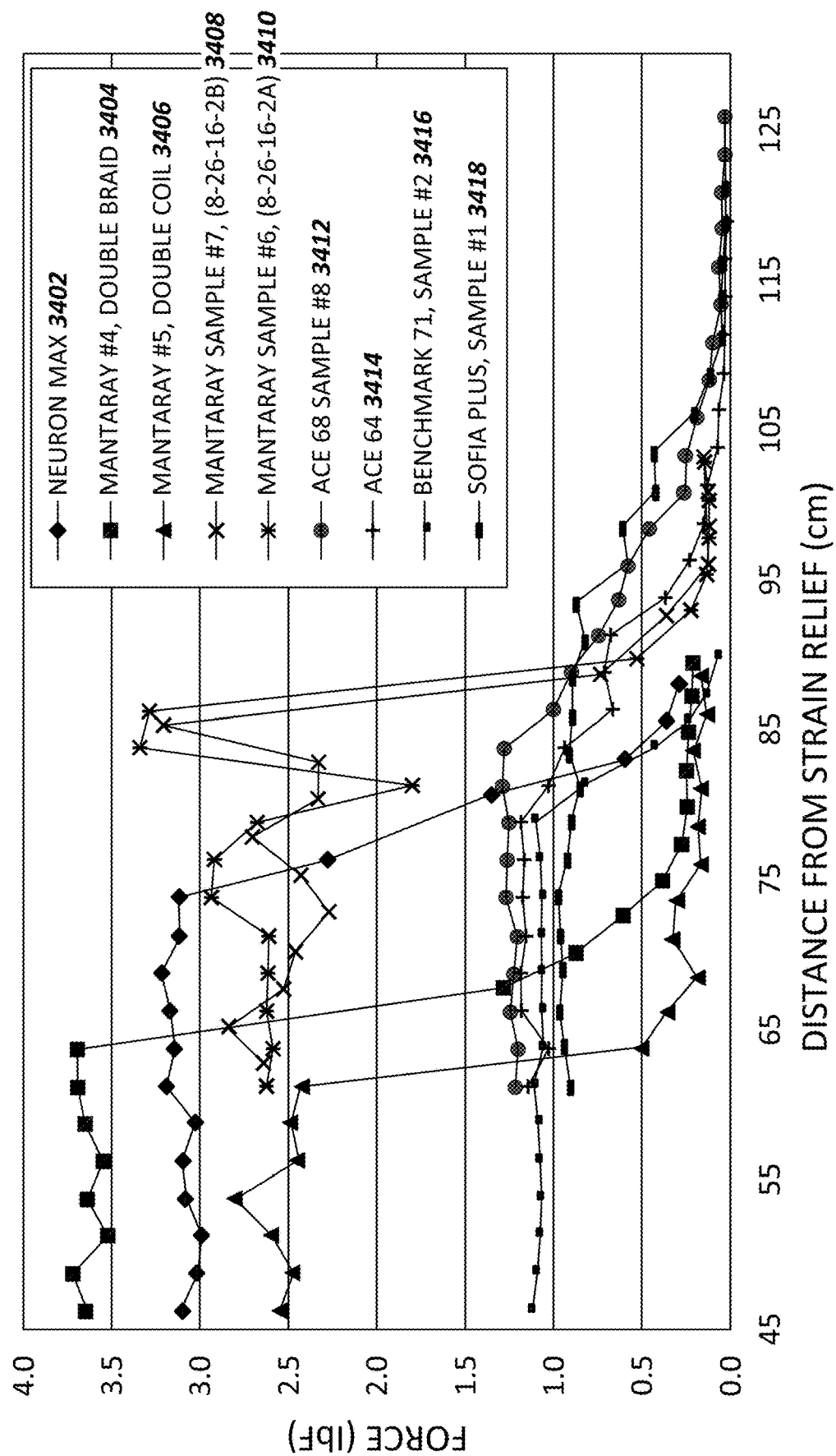
FIG. 11 depicts a graph of flexure test profiles of catheters in accordance with some embodiments compared with conventional catheters.

FIG. 11 describes flexibility test profiles of catheters in accordance with the embodiments herein compared with conventional catheters. Flexibility of a catheter was measured by the three point flexural test with a span of one inch and a displacement of 2 mm. In other words, FIG. 11 describes a force (i.e., flexural load) necessary to vertically displace a one-inch-long catheter segment by 2 mm with respect to distance from strain relief (i.e., proximal end of the catheter) to the point of force application. All catheters tested in FIG. 21 show modulus or flexibility profiles similar to the one shown in FIG. 10. Modulus of the catheters stays substantially constant along its length near the proximal end and then gradually decreases near the distal end.

Catheters according to some embodiments herein may have a flexural load that is substantially constant along the longitudinal length near the proximal end and a rapidly decreasing flexural load near the distal end. In a catheter having a length of about 125 cm, the catheters may have a flexural load greater than or equal to about 1.0 lbF, about 1.5 lbF, about 2.0 lbF, about 2.5 lbF, about 3.0 lbF, or about 3.5 lbF at about 85 cm from the proximal end. The catheters may have a flexural load less than or equal to about 2.5 lbF, about 2.0 lbF, about 1.5 lbF, about 1.0 lbF, or about 0.5 lbF at about 95 cm from the proximal end. The catheters may have a flexural load less than or equal to about 1.5 lbF, about 1.0 lbF, about 0.75 lbF, about 0.5 lbF, about 0.25 lbF, or about 0.1 lbF at about 105 cm from the proximal end. The catheters may have a flexural load less than or equal to about 1.0 lbF, about 0.75 lbF, about 0.5 lbF, about 0.4 lbF, about 0.3 lbF, about 0.2 lbF, or about 0.1 lbF at about 115 cm from the proximal end. For catheters having different lengths, the foregoing dimensions can be scaled from the distal end of the catheter as a percentage of catheter length.

In some embodiments constructed in accordance with FIG. 4, the flexural load may be less than about 3.0 or 3.25 lbF at 65 cm from the proximal end and greater than about 2.25 or 2.5 lbF on average from 65 cm to 85 cm from the proximal end. Flexural load may drop to no more than about 1.0 and preferably no more than about 0.5 lbF at about 95 cm from the proximal end. This provides enhanced backup support in the aorta while maintaining enhanced trackability into the distal vasculature.

In some embodiments, the catheters may have a flexural load greater than or equal to about 1.0 lbF, about 1.5 lbF, about 2.0 lbF, about 2.5 lbF, about 3.0 lbF, or about 3.5 lbF at about 60 cm from the proximal end. The catheters may have a flexural load less than or equal to about 2.0 lbF, about 1.5 lbF, about 1.0 lbF, or about 0.5 lbF at about 70 cm from the proximal end. The catheters may have a flexural load less than or equal to about 1.0 lbF, about 0.75 lbF, about 0.5 lbF, about 0.4 lbF, about 0.3 lbF, about 0.2 lbF, or about 0.1 lbF at about 80 cm from the proximal end. The catheters may have a flexural load less than or equal to about 1.0 lbF, about 0.75 lbF, about 0.5 lbF, about 0.4 lbF, about 0.3 lbF, about 0.2 lbF, or about 0.1 lbF at about 90 cm from the proximal end.

The catheters may have a transition region, in which its flexural load changes by greater than or equal to about 1.0 lbF, about 1.5 lbF, about 2.0 lbF, about 2.5 lbF, about 3.0 lbF, or about 3.5 lbF. The longitudinal length of the transition region may be less than or equal to about 20 cm, about 15 cm, about 10 cm, about 5 cm, about 3 cm, or about 1 cm.

Compared to Neuron Max (Penumbra, Inc.) 3402, catheters according to some of the embodiments described herein (e.g., 3404, 3406, 3408, 3410) have comparable modulus near their proximal end. This way, the catheters according to some embodiments provide back-up support comparable to that of Neuron Max 3402. In addition, the catheters may have modulus that decrease more rapidly near the transition region (between the proximal end and the distal end) than that of Neuron Max.

Compared to Ace 68 catheter (Penumbra) 3412, Ace 64 catheter (Penumbra) 3414, Benchmark 71 catheter (Penumbra) 3416, and Sofia Plus (MicroVention) 3418, the catheters according to some embodiments herein have greater modulus near their proximal end and comparable modulus near their distal end. This way, the catheters according to some embodiments herein provide superior back-up support with comparable trackability compared to conventional catheters. The catheters according to some embodiments herein may achieve this modulus profile even when their inner diameters (and thus lumen volumes) are greater than or equal to those of Ace 68, Ace 64, Benchmark 71, and Sofia Plus, which range from 0.064 inch to 0.071 inch.

Many of the catheters in accordance with the present invention include a side wall junction such as transition 3011 in FIG. 4, between a proximal tubular support structure such as a braid 3010 and an axially adjacent different tubular support structure such as coil 3024. A variety of structural features may be included to distribute force and improve the bending characteristics across the transition, as illustrated in FIGS. 12-25.

The location of the junction along the axial length of the catheter may be varied depending upon the desired performance. In some implementations, the catheter segment distal of the junction will have a length within the range of from about 12 cm to about 20 cm or within the range of from about 14 cm and 18 cm, in a catheter having an overall length within the range of from about 80 cm to about 110 cm. In other implementations, the catheter segment distal of the junction will have a length within the range of from about 35 cm to about 45 cm or within the range of from about 38 cm to about 42 cm, in a catheter having an overall length within the range of from about 150 cm to about 170 cm or within the range of from about 155 cm to about 161 cm.

Figure 12:
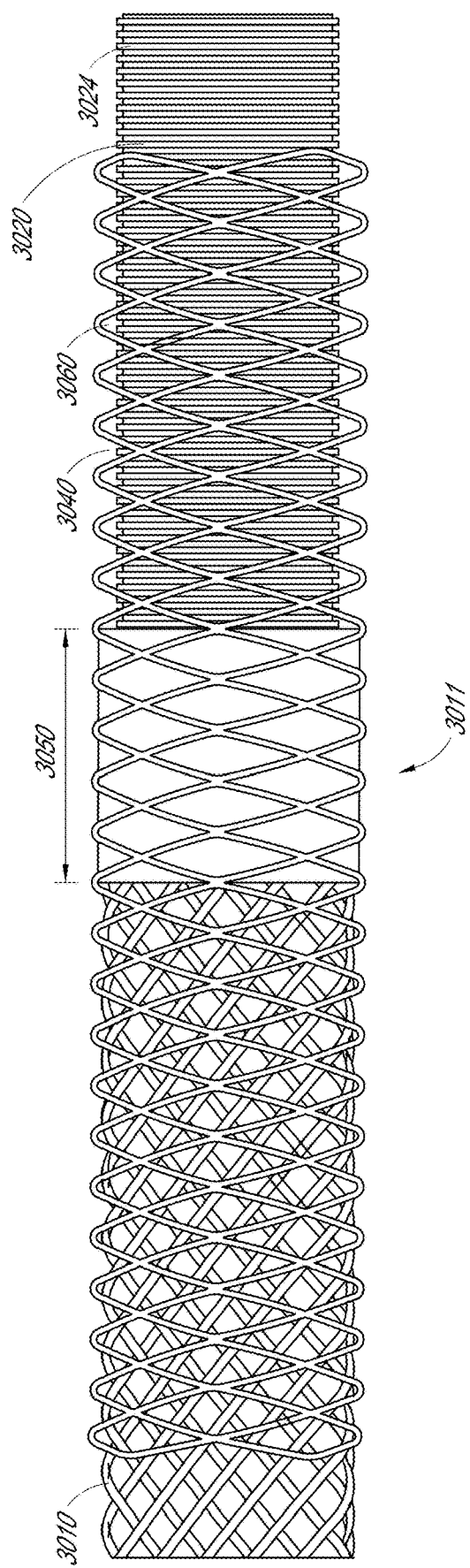
FIG. 12 shows a side view of a catheter with a distal transition cover according to some embodiments.
Figure 13:
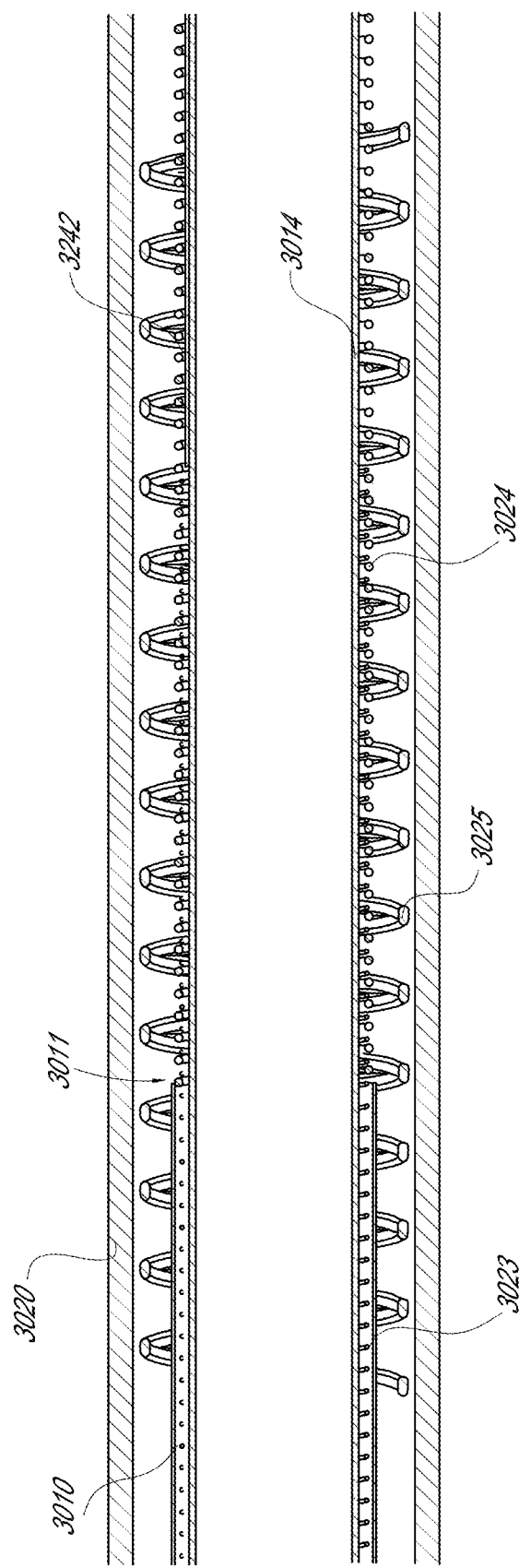
FIG. 13 is a longitudinal cross-sectional view of the catheter wall segment shown in FIG. 12.

Referring to FIGS. 12 and 13, shown is a side view and longitudinal cross section of an example catheter with a force dissipation support or cover 3060 embedded in the side wall and spanning the junction between a proximal braid 3010 and a distal coil 3024. The support may be a tubular segment such as a stent. In this embodiment, the stent was made by laser cutting a section of thin-walled Nitinol tubing followed by electro polishing the stent, creating, as shown, a stent with struts oriented in a predominantly circumferential direction with a strut thickness of about 0.0015". The stent may have an axial length of at least about 2 cm or at least about 3 cm or at least about 5 cm but generally no more than about 20 cm or 15 cm or less.

The stent may be loaded on the catheter comprising a proximal zone comprising a braid 3010 and a distal zone comprising a coil 3024 at a distal transition 3011 by loading it onto a mandrel before assembly. Further as shown in this example, a distal transition cover jacket 3070 overlays the stent and comprises a thin-walled PET sleeve of about 0.00025" thickness that was heat shrunk over the stent.

The stent thus spans the junction between the distal end of the braid 3010 and the proximal end of the coil 3024. An optional proximal coil 3023 may extend distally along the braid such as from the hub and across the junction, thus axially overlapping with the distal coil 3024 along an intertwined zone in which the two coils are intertwined. The intertwined zone may have an axial length within the range of from about 5 mm to about 10 mm or may extend up to a length of 5 cm or 10 cm or more depending upon desired performance characteristics.

The proximal coil 3023 may extend distally across the intertwined zone to end within the axial length of the support. In the illustrated implementation, the distal end of the coil 3023 is approximately adjacent the proximal end of the axially extending filament 3242. The proximal coil may be formed from stainless steel wire, having a larger diameter than the distal coil 3024 which may be formed from NiTi wire. SS has a significantly higher modulus than NiTi, so reducing the relative diameter of the SS coil is useful to keep the transition from one to the other 'smooth' in terms of stiffness.

Also as shown in this example, the braid 3010 of the proximal zone comprises a zone of reduced thickness 3050 leading up to the junction in distal transition 3011. In particular, the zone of reduced thickness 3050 was created by etching about 2 cm of axial length of the braid 3010, which comprises stainless steel ribbon with a thickness of about 0.0015" and a width of about 0.004", down to a ribbon thickness of about 0.0012"; since the braid as shown in this example comprises two interwoven stainless steel ribbons, the etching process reduced the overall braid outer diameter from about 0.0030" down to about 0.0024", which closely matches the about 0.0025" outer diameter of the coil 3024 comprising Nitinol. Catheters made with this configuration kinked in the U-bend kink test as described herein over a pin with a 24 mm diameter (this diameter is slightly smaller than the typical inner diameter of the aortic arch), which would allow such a catheter to prolapse inside an aortic arch of a human without kinking.

In another example, a distal transition cover 3060 comprising a Nitinol braid made with 0.001" outer diameter wire was placed over a proximal zone and a distal zone of a catheter as described herein. In this example, the catheter comprised a stainless steel braid with a wire ribbon of 0.0015" thickness and 0.004" width that was etched 2 cm at its distal end to reduce its overall thickness to 0.0024" (the stainless steel braid comprised two wire ribbons, with each ribbon being reduced in thickness from the etching process to 0.0012" thickness). This created a thickness of the stainless steel braid of the proximal zone (0.0024") that closely matched a thickness of a Nitinol coil of a distal zone (0.0025"). Catheters made with this configuration kinked in the U-bend kink test as described herein over a pin with a 24 mm diameter (this diameter is slightly smaller than the typical inner diameter of the aortic arch), which would allow such a catheter to prolapse inside an aortic arch of a human without kinking.

In another example, a distal transition cover 3060 comprising the liquid crystal polymer Vectran was placed over a proximal zone and a distal zone of a catheter as described herein. In this example, the Vectran was laminated with a thin layer of Vestamid over a mandrel before assembly onto the catheter. Further in this example, fibers of the Vectran were oriented about the longitudinal axis of the catheter to increase the tensile strength of the catheter in its location (i.e., not braided in order to minimize the overall thickness of this distal transition cover embodiment). In another example, fibers of the Vectran were oriented at about 45 degrees to the longitudinal axis of the catheter.

Referring to FIGS. 14A-14F and FIGS. 15A-15F, catheters of the various embodiments described herein may comprise a distal transition 3011. FIGS. 14A-14F and FIGS. 15A-15F illustrate cross-sectional elevational views of a catheter wall with various embodiments of the distal transition 3011 wherein a proximal braid 3010 has a zone of reduced thickness 3050 at the distal transition 3011.

In some embodiments, a zone 3050 of increased flexibility (e.g., reduced thickness) may comprise a length of about 0.5 cm, about 1.0 cm, about 1.5 cm, about 2.0 cm, about 2.5 cm, about 3.0 cm and about 3.5 cm. In some embodiments, a zone of reduced thickness 3050 may comprise a length of at least about 0.5 cm. In some embodiments, a zone of reduced thickness 3050 may comprise a length of less than about 3.0 cm. In some embodiments, a zone of reduced thickness 3050 may comprise a length of about 1.5 cm to about 2.5 cm. In some embodiments, a zone of reduced thickness 3050 may comprise a braid of a proximal zone of a catheter as described herein with a reduced thickness. In some embodiments, a zone of reduced thickness 3050 may comprise a braid of a proximal zone of a catheter as described herein with a reduced outer diameter. In some embodiments, a zone of reduced thickness 3050 may comprise a braid of a proximal zone of a catheter as described herein with an enlarged inner diameter. In some embodiments, a zone of reduced thickness 3050 may comprise a braid of a proximal zone of a catheter as described herein with a reduced outer diameter and an enlarged inner diameter. In some embodiments, a zone of reduced thickness 3050 may comprise a smooth, a curved, a curvilinear, a linear, and a stepped transition in thickness. In some embodiments, a zone of reduced thickness 3050 may comprise a smooth, a curved, a curvilinear, a linear, and a stepped transition in catheter stiffness between a proximal zone and a distal zone of the catheter and provide superior kink resistance. In some embodiments, a zone of reduced thickness 3050 may create a transition in catheter stiffness between a proximal zone and a distal zone of the catheter and provide superior kink resistance. In some embodiments, a zone of reduced thickness 3050 may reduce a stiffness of a proximal zone of a catheter and provide superior kink resistance. In some embodiments, a zone of reduced thickness 3050 may reduce a stiffness of a braid of a proximal zone of a catheter and provide superior kink resistance.

A reduced thickness of a proximal braid 3010 at a distal transition 3011 may be accomplished by etching the braid at its distal end where it meets distal transition 3011. The etching may be performed prior to annealing. The etching may be performed after annealing. The etching may be performed prior to application of an inner liner 3014 and a tie layer 3012. The etching may be performed after application of an inner liner 3014 and a tie layer 3012. The etching may be applied to an outer surface of a proximal braid 3010, thus creating a proximal braid with a reduced outer diameter at a distal transition 3011. The etching may be applied to an inner surface of a proximal braid 3010, thus creating a proximal braid with an enlarged inner diameter at a distal transition 3011. The etching may be applied to an outer surface and an inner surface of a proximal braid 3010, thus creating a proximal braid with a reduced outer diameter and an enlarged inner diameter at a distal transition 3011. The etching may be performed to create about the same (e.g., ±10%) or different thickness profiles between an inner surface and an outer surface of a proximal braid 3010 at a distal transition 3011. Alternatively, a reduced thickness of a proximal braid 3010 at a distal transition 3011 may be accomplished by utilizing a braid with a thinner thickness where it meets distal transition 3011, such as by extrusion of a ribbon comprising the braid.

In one non-limiting example, etching a distal 2 cm of a stainless steel braid comprising stainless steel ribbon with a thickness of 0.0015" reduced the thickness of the braid to 0.0011". When catheters comprising this etched stainless steel braid were laminated with 0.0035" wall thickness Vestamid, the resulting etched catheters were found to be able to resist kinking in a U-bend kink test (i.e., bending an unsupported shaft of a catheter 180 degrees around a pin starting with a pin of a relatively large outer diameter and progressively testing on smaller diameter pins) until wrapped around a pin with an outer diameter of 18 mm. In practice, this enables a catheter of this embodiment to prolapse within an aortic arch of a human without kinking.

Figure 14A:
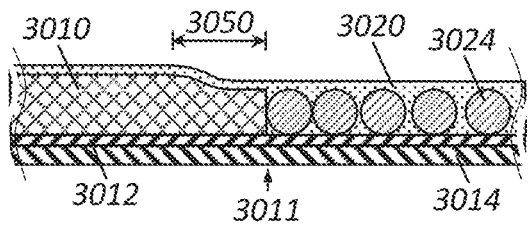
FIGS. 14A-14F illustrate cross-sectional elevational views of a catheter wall at a distal transition according to some embodiments.

Referring to FIG. 14A, shown is a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. In this embodiment, the zone of reduced thickness 3050 may allow for a reduced outer diameter of catheter 3000 in the distal direction, while the inner diameter of catheter 3000 may remain about the same (e.g., ±10%) between the proximal and distal zones at distal transition 3011. Also as shown, this embodiment may optionally comprise an inner liner 3014, a tie layer 3012, and a sleeve 3020 as described elsewhere herein.

Figure 14D:
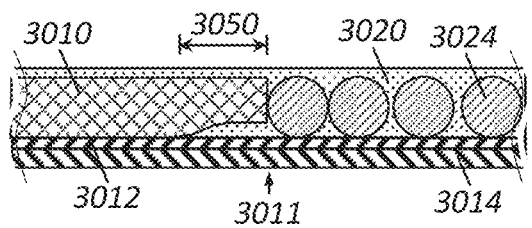
Figure 14B:
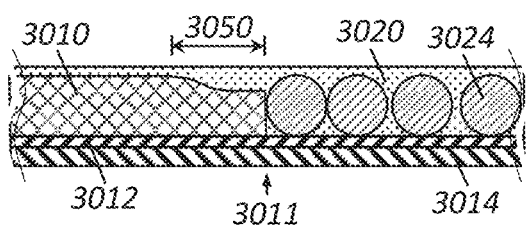

Referring to FIG. 14B, shown is a braid 3010 of a proximal zone with a zone of reduced thickness 3050 with an outer diameter that is smaller than an outer diameter of a coil 3024 of a distal zone, and an inner diameter that is about the same (e.g., ±10%) as an inner diameter of the coil 3024 of the distal zone at a distal transition 3011. In this embodiment, the outer diameter and inner diameter of catheter 3000 may be about the same (e.g., ±10%) between the proximal and distal zones at distal transition 3011. Also as shown, this embodiment may optionally comprise an inner liner 3014, a tie layer 3012, and a sleeve 3020 as described elsewhere herein.

Figure 14E:
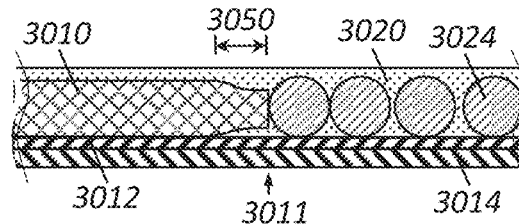
Figure 14C:
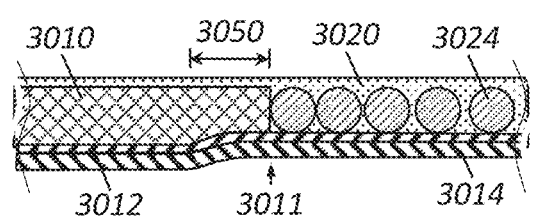

Referring to FIG. 14C, shown is a braid 3010 of a proximal zone with a zone of reduced thickness 3050 with an inner diameter that is about the same (e.g., ±10%) as an inner diameter of a coil 3024 of a distal zone, and an outer diameter that is about the same (e.g., ±10%) as the outer diameter of the coil 3024 at a distal transition 3011. In this embodiment, the zone of reduced thickness 3050 may allow for an enlarged inner diameter of catheter 3000 in the distal direction, while the outer diameter of catheter 3000 may remain about the same (e.g., ±10%) between the proximal and distal zones at distal transition 3011. Also as shown, this embodiment may optionally comprise an inner liner 3014, a tie layer 3012, and a sleeve 3020 as described elsewhere herein.

Referring to FIG. 14D, shown is a braid 3010 of a proximal zone with a zone of reduced thickness 3050 with an inner diameter that is larger than an inner diameter of a coil 3024 of a distal zone, and an outer diameter that is about the same (e.g., ±10%) as an outer diameter of the coil 3024 of the distal zone at a distal transition 3011. In this embodiment, the outer and inner diameter of catheter 3000 may be about the same (e.g., ±10%) between the proximal and distal zones at distal transition 3011. Also as shown, this embodiment may optionally comprise an inner liner 3014, a tie layer 3012, and a sleeve 3020 as described elsewhere herein.

Referring to FIG. 14E, shown is a braid 3010 of a proximal zone with a zone of reduced thickness 3050 with an outer diameter that is smaller than an outer diameter of a coil 3024 of a distal zone at a distal transition 3011, and an inner diameter that is larger than an inner diameter of the coil 3024 of the distal zone at the distal transition 3011. In this embodiment, the outer and inner diameter of catheter 3000 may be about the same (e.g., ±10%) between the proximal and distal zones at distal transition 3011. Also as shown, this embodiment may optionally comprise an inner liner 3014, a tie layer 3012, and a sleeve 3020 as described herein.

Figure 14F:
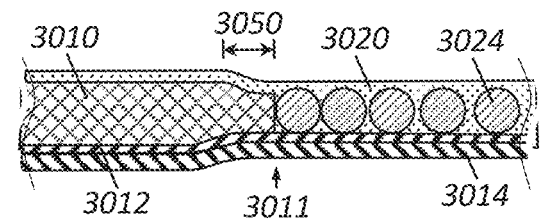

Referring to FIG. 14F, shown is a braid 3010 of a proximal zone with a zone of reduced thickness 3050 with an outer diameter that is about the same (e.g., ±10%) as an outer diameter of a coil 3024 of a distal zone at a distal transition 3011, and an inner diameter that is about the same (e.g., ±10%) as an inner diameter of the coil 3024 of the distal zone at the distal transition 3011. In this embodiment, the zone of reduced thickness 3050 may allow for a reduced outer diameter and an enlarged inner diameter of catheter 3000 in the distal direction between the proximal and distal zones at distal transition 3011. Also as shown, this embodiment may comprise an inner liner 3014, a tie layer 3012, and a sleeve 3020 as described herein.

Figure 15A:
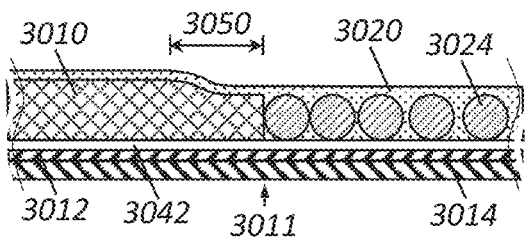
FIGS. 15A-15F illustrate cross-sectional elevational views of a catheter wall at a distal transition according to some embodiments, showing one or more axially extending filaments.

Referring to FIG. 15A, shown is a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. In this embodiment, the zone of reduced thickness 3050 may allow for a reduced outer diameter of catheter 3000 in the distal direction, while the inner diameter of catheter 3000 may remain about the same (e.g., ±10%) between the proximal and distal zones at distal transition 3011. Also as shown, this embodiment may optionally comprise an inner liner 3014, a tie layer 3012, an axially extending filament 3042, and a sleeve 3020 as described elsewhere herein.

Figure 15D:
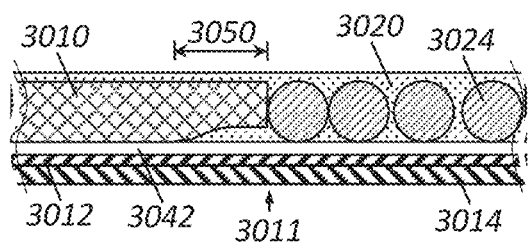
Figure 15B:
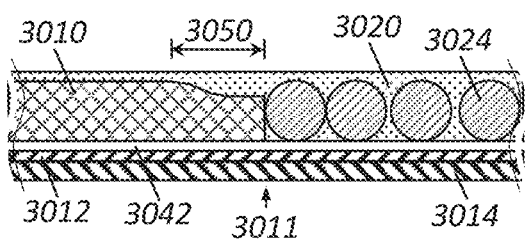

Referring to FIG. 15B, shown is a braid 3010 of a proximal zone with a zone of reduced thickness 3050 with an outer diameter that is smaller than an outer diameter of a coil 3024 of a distal zone, and an inner diameter that is about the same (e.g., ±10%) as an inner diameter of the coil 3024 of the distal zone at a distal transition 3011. In this embodiment, the outer diameter and inner diameter of catheter 3000 may be about the same (e.g., ±10%) between the proximal and distal zones at distal transition 3011. Also as shown, this embodiment may optionally comprise an inner liner 3014, a tie layer 3012, an axially extending filament 3042, and a sleeve 3020 as described elsewhere herein.

Figure 15E:
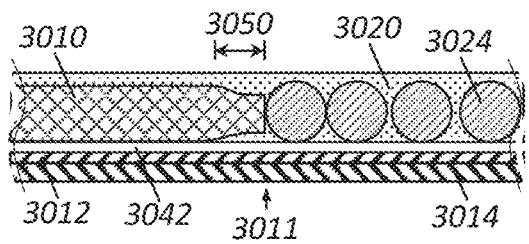
Figure 15C:
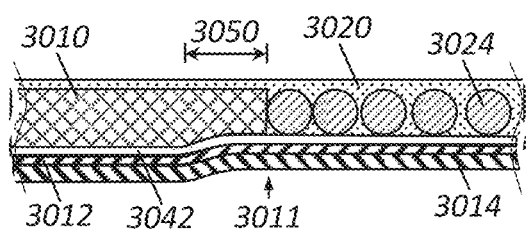

Referring to FIG. 15C, shown is a braid 3010 of a proximal zone with a zone of reduced thickness 3050 with an inner diameter that is about the same (e.g., ±10%) as an inner diameter of a coil 3024 of a distal zone, and an outer diameter that is about the same (e.g., ±10%) as the outer diameter of the coil 3024 at a distal transition 3011. In this embodiment, the zone of reduced thickness 3050 may allow for an enlarged inner diameter of catheter 3000 in the distal direction, while the outer diameter of catheter 3000 may remain about the same (e.g., ±10%) between the proximal and distal zones at distal transition 3011. Also as shown, this embodiment may optionally comprise an inner liner 3014, a tie layer 3012, an axially extending filament 3042, and a sleeve 3020 as described elsewhere herein.

Referring to FIG. 15D, shown is a braid 3010 of a proximal zone with a zone of reduced thickness 3050 with an inner diameter that is larger than an inner diameter of a coil 3024 of a distal zone, and an outer diameter that is about the same (e.g., ±10%) as an outer diameter of the coil 3024 of the distal zone at a distal transition 3011. In this embodiment, the outer and inner diameter of catheter 3000 may be about the same (e.g., ±10%) between the proximal and distal zones at distal transition 3011. Also as shown, this embodiment may optionally comprise an inner liner 3014, a tie layer 3012, an axially extending filament 3042, and a sleeve 3020 as described elsewhere herein.

Referring to FIG. 15E, shown is a braid 3010 of a proximal zone with a zone of reduced thickness 3050 with an outer diameter that is smaller than an outer diameter of a coil 3024 of a distal zone at a distal transition 3011, and an inner diameter that is larger than an inner diameter of the coil 3024 of the distal zone at the distal transition 3011. In this embodiment, the outer and inner diameter of catheter 3000 may be about the same (e.g., ±10%) between the proximal and distal zones at distal transition 3011. Also as shown, this embodiment may optionally comprise an inner liner 3014, a tie layer 3012, an axially extending filament 3042, and a sleeve 3020 as described elsewhere herein.

Figure 15F:
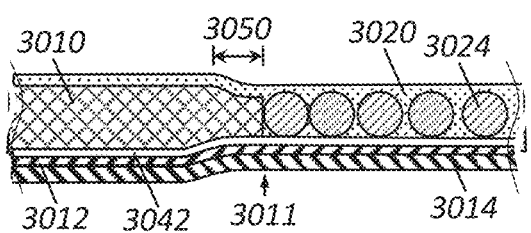

Referring to FIG. 15F, shown is a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. In this embodiment, the zone of reduced thickness 3050 may allow for a reduced outer diameter and an enlarged inner diameter of catheter 3000 in the distal direction between the proximal and distal zones at distal transition 3011. Also as shown, this embodiment may optionally comprise an inner liner 3014, a tie layer 3012, an axially extending filament 3042, and a sleeve 3020 as described elsewhere herein.

Referring to FIGS. 16A-16F, FIGS. 17A-17F, FIGS. 18A-18F, FIGS. 19A-19F, and FIG. 20, catheters of the various embodiments described herein may comprise a distal transition 3011 with a distal transition cover 3060. Also shown in FIG. 16C, FIG. 16F, FIG. 17C, FIG. 17F, FIG. 18B, FIG. 18E, FIG. 19B, FIG. 19E, and FIG. 20, catheters of the various embodiments described herein may comprise a distal transition 3011 with a distal transition cover 3060 and a distal transition cover sleeve 3070. Note that FIGS. 16A-16F, FIGS. 17A-17F, FIGS. 18A-18F, and FIGS. 19A-19F illustrate cross-sectional elevational views of a catheter wall according to some of these various embodiments.

In some embodiments, a distal transition cover 3060 may comprise a braid (e.g., a wire braid, a stainless steel wire braid, a stainless steel ribbon braid, a shape-memory or superelastic wire braid, a shape-memory or superelastic ribbon braid, a Nitinol wire braid, a Nitinol ribbon braid, a polymer braid, a nylon braid, a polypropylene braid, a polyester braid), a stent (e.g., a stainless steel stent, a shape-memory or superelastic stent, a Nitinol stent, a polymer stent, a nylon stent, a polypropylene stent, a polyester stent), a coil (e.g., a stainless steel coil, a shape-memory or superelastic coil, a polymer coil, a nylon coil, a polypropylene coil), a liquid crystal polymer (e.g., PET copolyester, copolyimide, polyester-amide, Vectran), a shrink-wrap or heat-shrink tubing, and a composite material. In some embodiments, a distal transition cover 3060 may extend about a distal transition 3011 in about equal lengths distally and proximally. In some embodiments, a distal transition cover 3060 may extend about a distal transition 3011 more in the proximal direction than in the distal direction (e.g., to cover more of the catheter's proximal zone than its distal zone). In some embodiments, a distal transition cover 3060 may extend about a distal transition 3011 more in the distal direction than in the proximal direction (e.g., to cover more of the catheter's distal zone than its proximal zone). In some embodiments, a distal transition cover 3060 may cover a catheter comprising a proximal zone comprising a braid and a distal zone comprising a coil. Parameters of braid, stent, coil, liquid crystal polymer, shrink-wrap or heat-shrink tubing, and composite materials that comprise a distal transition cover 3060 may be modified to tune the stiffness and flexibility of a catheter (e.g., braid wire thickness, braid wire width, stent strut orientation, stent window size, stent thickness, liquid crystal polymer orientation about the catheter axis, shrink-wrap or heat-shrink tubing thickness and composition).

In some embodiments, a catheter with a distal transition cover 3060 may comprise a distal transition cover sleeve 3070 that covers the distal transition cover 3060. In some embodiments, a distal transition cover sleeve 3070 may comprise a shrink-wrap or heat-shrink tubing, a polymer, and/or a composite material. An example of a distal transition cover sleeve material includes thin-walled PET. In some embodiments, a distal transition cover sleeve 3070 may extend beyond a distal transition cover 3060 and cover a proximal zone and a distal zone of a catheter 3000. In some embodiments, a distal transition cover sleeve 3070 may cover a distal transition cover 3060 and cover a proximal zone and a distal zone of a catheter 3000 in variable lengths.

In some embodiments, a distal transition cover 3060 may provide a transition in catheter stiffness between a proximal zone and a distal zone of the catheter and provide superior kink resistance. In some embodiments, a distal transition cover 3060 and a distal transition cover sleeve 3070 may provide a transition in catheter stiffness between a proximal zone and a distal zone of the catheter and provide superior kink resistance.

In some embodiments, a distal transition cover 3060 may be placed over a mandrel before assembly onto a catheter as described herein. In some embodiments, a distal transition cover sleeve may be assembled over a distal transition cover 3060 (e.g., a thin wall PET sleeve of about 0.00025" heat shrinked over the distal transition cover).

Figure 16A:
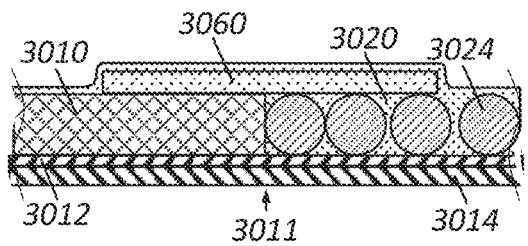
FIGS. 16A-16F illustrate cross-sectional elevational views of a catheter wall at a distal transition with a distal transition cover according to some embodiments.

Referring to FIG. 16A, shown is a catheter with a distal transition 3011 covered by a distal transition cover 3060 comprising a braid, a stent, a liquid crystal polymer, a shrink-wrap or heat-shrink tubing, and/or a composite material that directly abuts an underlying braid 3010 of a proximal zone and an underlying coil 3024 of a distal zone. Further as shown, distal transition cover 3060 may be covered by sleeve 3020 that covers at least a portion of the distal zone as described herein. Also as shown, this embodiment may optionally comprise an inner liner 3014 and a tie layer 3012 as described elsewhere herein.

Figure 16B:
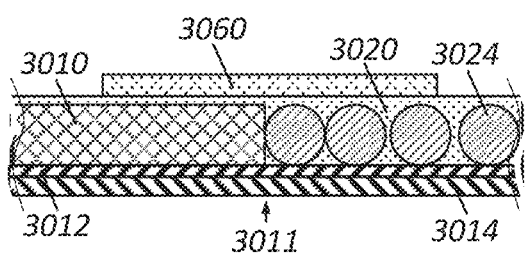

Referring to FIG. 16B, shown is a catheter with a distal transition 3011 covered by a distal transition cover 3060 comprising a braid, a stent, a liquid crystal polymer, a shrink-wrap or heat-shrink tubing, and/or a composite material. A cover sleeve 3020 separates a braid 3010 of a proximal zone and a coil 3024 of a distal zone from the distal transition cover 3060 (i.e., cover sleeve 3020 is formed under distal transition cover 3060). Also as shown, this embodiment may optionally comprise an inner liner 3014 and a tie layer 3012 as described elsewhere herein.

Figure 16C:
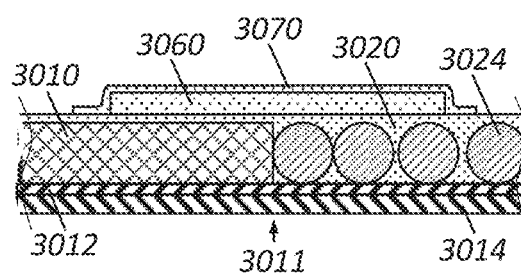

Referring to FIG. 16C, shown is a catheter with a distal transition 3011 covered by a distal transition cover 3060 comprising a braid, a stent, a liquid crystal polymer, a shrink-wrap or heat-shrink tubing, and/or a composite material. A cover sleeve 3020 separates a braid 3010 of a proximal zone and a coil 3024 of a distal zone from the distal transition cover 3060. Further as shown, distal transition cover 3060 may be covered by a distal transition cover sleeve 3070, which in this example extends proximally and distally beyond the distal transition cover 3060. Also as shown, this embodiment may optionally comprise an inner liner 3014 and a tie layer 3012 as described elsewhere herein.

Figure 16D:
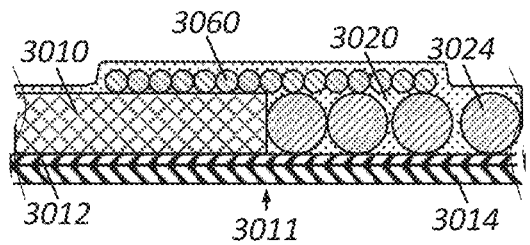

Referring to FIG. 16D, shown is a catheter with a distal transition 3011 covered by a distal transition cover 3060 comprising a coil that directly abuts an underlying braid 3010 of a proximal zone and an underlying coil 3024 of a distal zone. Further as shown, distal transition cover 3060 may be covered by sleeve 3020 that covers at least a portion of the distal zone as described herein. Also as shown, this embodiment may optionally comprise an inner liner 3014 and a tie layer 3012 as described elsewhere herein.

Figure 16E:
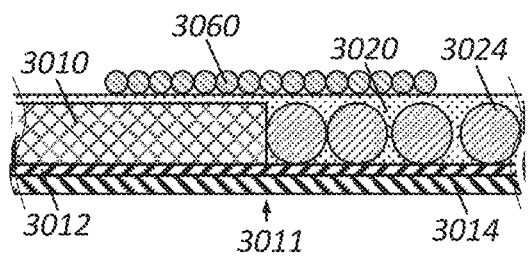

Referring to FIG. 16E, shown is a catheter with a distal transition 3011 covered by a distal transition cover 3060 comprising a coil. A cover sleeve 3020 separates a braid 3010 of a proximal zone and a coil 3024 of a distal zone from the distal transition cover 3060. Also as shown, this embodiment may optionally comprise an inner liner 3014 and a tie layer 3012 as described elsewhere herein.

Figure 16F:
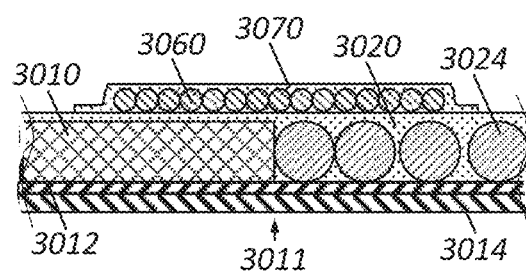

Referring to FIG. 16F, shown is a catheter with a distal transition 3011 covered by a distal transition cover 3060 comprising a coil. A cover sleeve 3020 separates a braid 3010 of a proximal zone and a coil 3024 of a distal zone from the distal transition cover 3060. Further as shown, distal transition cover 3060 may be covered by a distal transition cover sleeve 3070, which in this example extends proximally and distally beyond the distal transition cover 3060. Also as shown, this embodiment may optionally comprise an inner liner 3014 and a tie layer 3012 as described elsewhere herein.

Figure 17A:
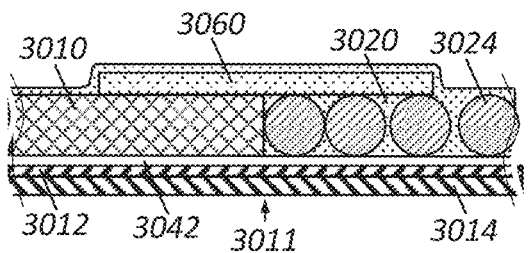
FIGS. 17A-17F illustrate cross-sectional elevational views of a catheter wall at a distal transition with a distal transition cover according to some embodiments, showing one or more axially extending filaments.

Referring to FIG. 17A, shown is a catheter with a distal transition 3011 covered by a distal transition cover 3060 comprising a braid, a stent, a liquid crystal polymer, a shrink-wrap or heat-shrink tubing, and/or a composite material that directly abuts an underlying braid 3010 of a proximal zone and an underlying coil 3024 of a distal zone. Further as shown, distal transition cover 3060 may be covered by sleeve 3020 that covers at least a portion of the distal zone as described herein. Also as shown, this embodiment may comprise an inner liner 3014, a tie layer 3012, and an axially extending filament 3042 as described elsewhere herein.

Figure 17D:
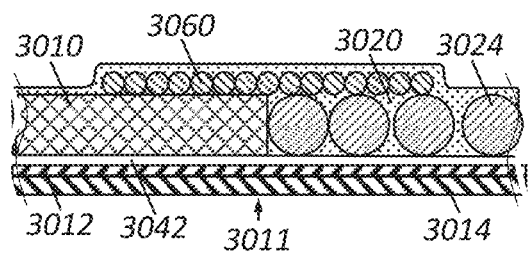
Figure 17B:
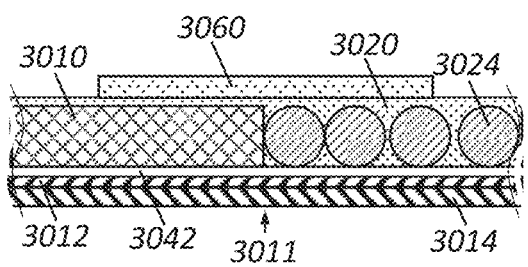

Referring to FIG. 17B, shown is a catheter with a distal transition 3011 covered by a distal transition cover 3060 comprising a braid, a stent, a liquid crystal polymer, a shrink-wrap or heat-shrink tubing, and a composite material. A cover sleeve 3020 separates a braid 3010 of a proximal zone and a coil 3024 of a distal zone from the distal transition cover 3060. Also as shown, this embodiment may optionally comprise an inner liner 3014, a tie layer 3012, and an axially extending filament 3042 as described elsewhere herein.

Figure 17E:
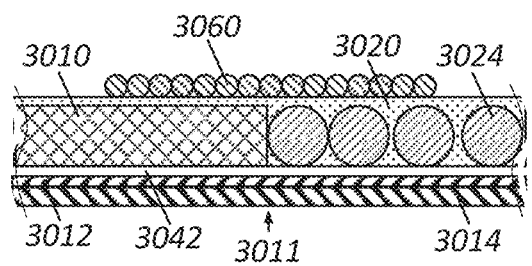
Figure 17C:
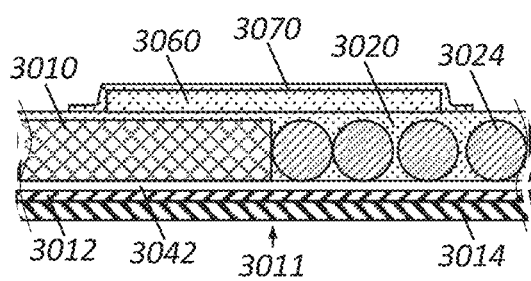

Referring to FIG. 17C, shown is a catheter with a distal transition 3011 covered by a distal transition cover 3060 comprising a braid, a stent, a liquid crystal polymer, a shrink-wrap or heat-shrink tubing, and a composite material. A cover sleeve 3020 separates a braid 3010 of a proximal zone and a coil 3024 of a distal zone from the distal transition cover 3060. Further as shown, distal transition cover 3060 may be covered by a distal transition cover sleeve 3070, which in this example extends proximally and distally beyond the distal transition cover 3060. Also as shown, this embodiment may optionally comprise an inner liner 3014, a tie layer 3012, and an axially extending filament 3042 as described elsewhere herein.

Referring to FIG. 17D, shown is a catheter with a distal transition 3011 covered by a distal transition cover 3060 comprising a coil that directly abuts an underlying braid 3010 of a proximal zone and an underlying coil 3024 of a distal zone. Further as shown, distal transition cover 3060 may be covered by sleeve 3020 that covers at least a portion of the distal zone as described herein. Also as shown, this embodiment may optionally comprise an inner liner 3014, a tie layer 3012, and an axially extending filament 3042 as described elsewhere herein.

Referring to FIG. 17E, shown is a catheter with a distal transition 3011 covered by a distal transition cover 3060 comprising a coil. A cover sleeve 3020 separates a braid 3010 of a proximal zone and a coil 3024 of a distal zone from the distal transition cover 3060. Also as shown, this embodiment may optionally comprise an inner liner 3014, a tie layer 3012, and an axially extending filament 3042 as described elsewhere herein.

Figure 17F:
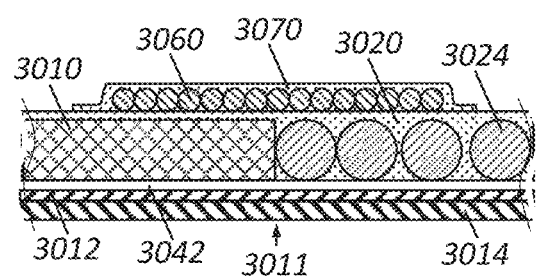

Referring to FIG. 17F, shown is a catheter with a distal transition 3011 covered by a distal transition cover 3060 comprising a coil. A cover sleeve 3020 separates a braid 3010 of a proximal zone and a coil 3024 of a distal zone from the distal transition cover 3060. Further as shown, distal transition cover 3060 may be covered by a distal transition cover sleeve 3070, which in this example extends proximally and distally beyond the distal transition cover 3060. Also as shown, this embodiment may optionally comprise an inner liner 3014, a tie layer 3012, and an axially extending filament 3042 as described elsewhere herein.

Figure 18A:
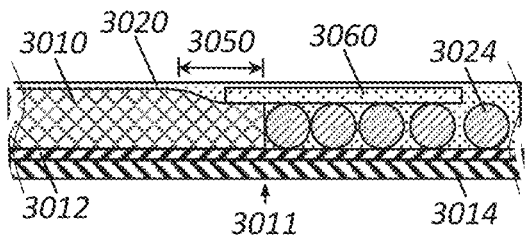
FIGS. 18A-18F illustrate cross-sectional elevational views of a catheter wall at a distal transition with a distal transition cover according to some embodiments.

In some embodiments, a catheter 3000 may combine multiple aspects of the various distal transitions described herein. Referring to FIG. 18A, shown is a catheter with a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. The distal transition 3011 is covered by a distal transition cover 3060 comprising a braid, a stent, a liquid crystal polymer, a shrink-wrap or heat-shrink tubing, and a composite material that directly abuts the underlying braid 3010 of the proximal zone and the underlying coil 3024 of the distal zone. Further as shown, distal transition cover 3060 may be covered by sleeve 3020 that covers at least a portion of the distal zone as described herein. Also as shown, this embodiment may optionally comprise an inner liner 3014 and a tie layer 3012 as described elsewhere herein.

Figure 18D:
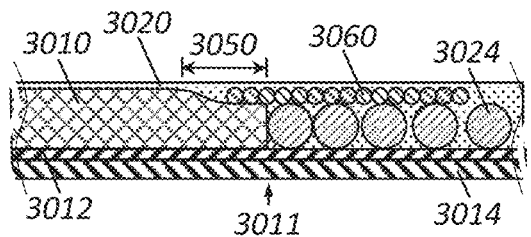
Figure 18B:
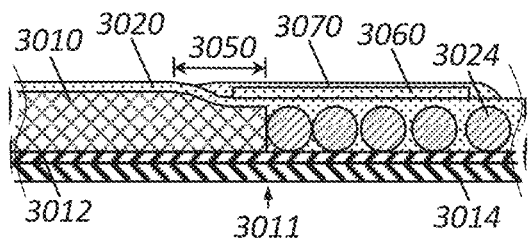

Referring to FIG. 18B, shown is a catheter with a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. The distal transition 3011 is covered by a distal transition cover 3060 comprising a braid, a stent, a liquid crystal polymer, a shrink-wrap or heat-shrink tubing, and/or a composite material. A cover sleeve 3020 separates the braid 3010 of the proximal zone and the coil 3024 of the distal zone from the distal transition cover 3060. Further as shown, distal transition cover 3060 may be covered by a distal transition cover sleeve 3070, which in this example extends proximally and distally beyond the distal transition cover 3060. Also as shown, this embodiment may optionally comprise an inner liner 3014 and a tie layer 3012 as described elsewhere herein.

Figure 18E:
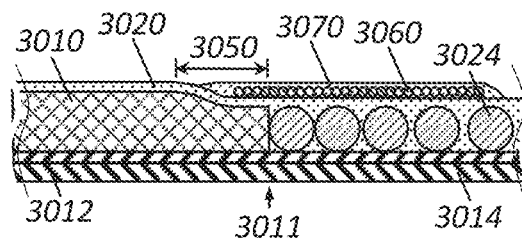
Figure 18C:
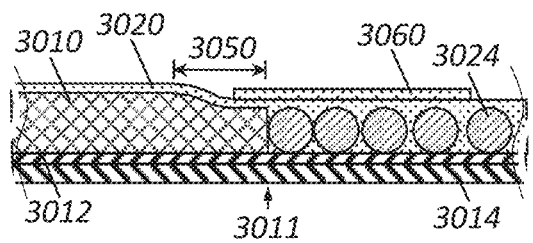

Referring to FIG. 18C, shown is a catheter with a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. The distal transition 3011 is covered by a distal transition cover 3060 comprising a braid, a stent, a liquid crystal polymer, a shrink-wrap or heat-shrink tubing, and/or a composite material. A cover sleeve 3020 separates the braid 3010 of the proximal zone and the coil 3024 of the distal zone from the distal transition cover 3060. Also as shown, this embodiment may optionally comprise an inner liner 3014 and a tie layer 3012 as described elsewhere herein.

Referring to FIG. 18D, shown is a catheter with a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. The distal transition 3011 is covered by a distal transition cover 3060 comprising a coil that directly abuts the underlying braid 3010 of the proximal zone and the underlying coil 3024 of the distal zone. Further as shown, distal transition cover 3060 may be covered by sleeve 3020 that covers at least a portion of the distal zone as described herein. Also as shown, this embodiment may optionally comprise an inner liner 3014 and a tie layer 3012 as described elsewhere herein.

Referring to FIG. 18E, shown is a catheter with a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. The distal transition 3011 is covered by a distal transition cover 3060 comprising a coil. A cover sleeve 3020 separates the braid 3010 of the proximal zone and the coil 3024 of the distal zone from the distal transition cover 3060. Further as shown, distal transition cover 3060 may be covered by a distal transition cover sleeve 3070, which in this example extends proximally and distally beyond the distal transition cover 3060. Also as shown, this embodiment may optionally comprise an inner liner 3014 and a tie layer 3012 as described elsewhere herein.

Figure 18F:
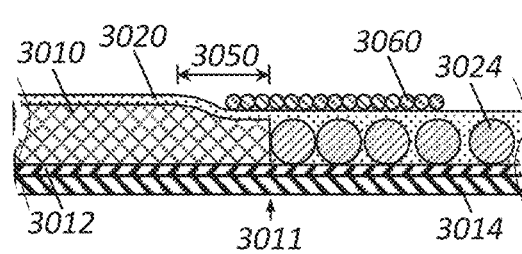

Referring to FIG. 18F, shown is a catheter with a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. The distal transition 3011 is covered by a distal transition cover 3060 comprising a coil. A cover sleeve 3020 separates the braid 3010 of the proximal zone and the coil 3024 of the distal zone from the distal transition cover 3060. Also as shown, this embodiment may optionally comprise an inner liner 3014 and a tie layer 3012 as described elsewhere herein.

Figure 19A:
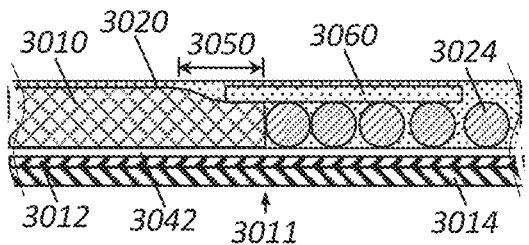
FIGS. 19A-19F illustrate cross-sectional elevational views of a catheter wall at a distal transition with a distal transition cover according to some embodiments, showing one or more axially extending filaments.

Referring to FIG. 19A, shown is a catheter with a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. The distal transition 3011 is covered by a distal transition cover 3060 comprising a braid, a stent, a liquid crystal polymer, a shrink-wrap or heat-shrink tubing, and/or a composite material that directly abuts the underlying braid 3010 of the proximal zone and the underlying coil 3024 of the distal zone. Further as shown, distal transition cover 3060 may be covered by sleeve 3020 that covers at least a portion of the distal zone as described herein. Also as shown, this embodiment may optionally comprise an inner liner 3014, a tie layer 3012, and an axially extending filament 3042 as described elsewhere herein.

Figure 19D:
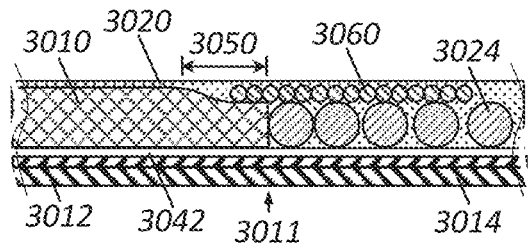
Figure 19B:
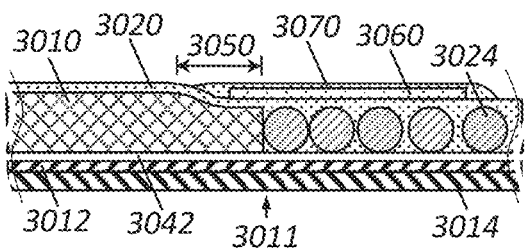

Referring to FIG. 19B, shown is a catheter with a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. The distal transition 3011 is covered by a distal transition cover 3060 comprising a braid, a stent, a liquid crystal polymer, a shrink-wrap or heat-shrink tubing, and/or a composite material. A cover sleeve 3020 separates the braid 3010 of the proximal zone and the coil 3024 of the distal zone from the distal transition cover 3060. Further as shown, distal transition cover 3060 may be covered by a distal transition cover sleeve 3070, which in this example, extends proximally and distally beyond the distal transition cover 3060. Also as shown, this embodiment may optionally comprise an inner liner 3014, a tie layer 3012, and an axially extending filament 3042 as described elsewhere herein.

Figure 19E:
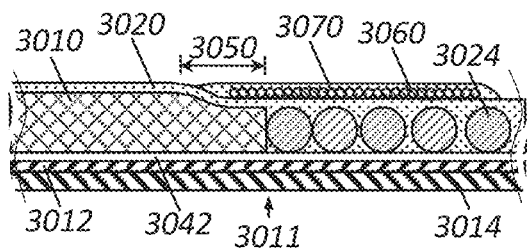
Figure 19C:
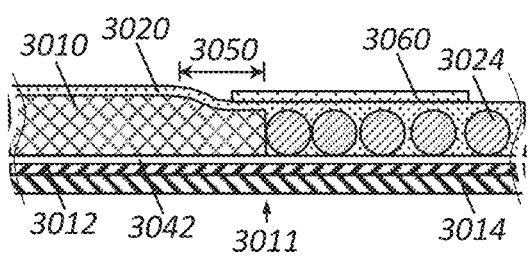

Referring to FIG. 19C, shown is a catheter with a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. The distal transition 3011 is covered by a distal transition cover 3060 comprising a braid, a stent, a liquid crystal polymer, a shrink-wrap or heat-shrink tubing, and/or a composite material. A cover sleeve 3020 separates the braid 3010 of the proximal zone and the coil 3024 of the distal zone from the distal transition cover 3060. Also as shown, this embodiment may comprise an inner liner 3014, a tie layer 3012, and an axially extending filament 3042 as described elsewhere herein.

Referring to FIG. 19D, shown is a catheter with a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. The distal transition 3011 is covered by a distal transition cover 3060 comprising a coil that directly abuts the underlying braid 3010 of the proximal zone and the underlying coil 3024 of the distal zone. Further as shown, distal transition cover 3060 may be covered by sleeve 3020 that covers at least a portion of the distal zone as described herein. Also as shown, this embodiment may optionally comprise an inner liner 3014, a tie layer 3012, and an axially extending filament 3042 as described elsewhere herein.

Referring to FIG. 19E, shown is a catheter with a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. The distal transition 3011 is covered by a distal transition cover 3060 comprising a coil. A cover sleeve 3020 separates the braid 3010 of the proximal zone and the coil 3024 of the distal zone from the distal transition cover 3060. Further as shown, distal transition cover 3060 may be covered by a distal transition cover sleeve 3070, which in this example, extends proximally and distally beyond the distal transition cover 3060. Also as shown, this embodiment may optionally comprise an inner liner 3014, a tie layer 3012, and an axially extending filament 3042 as described elsewhere herein.

Figure 19F:
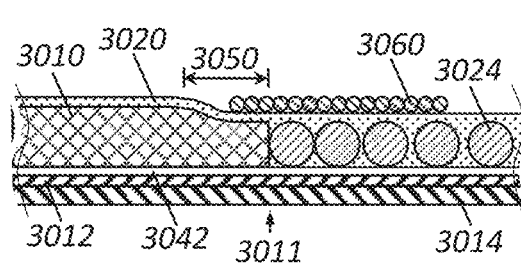

Referring to FIG. 19F, shown is a catheter with a braid 3010 of a proximal zone with a zone of reduced thickness 3050 with an outer diameter and an inner diameter that is about the same (e.g., ±10%) as an outer diameter and an inner diameter of a coil 3024 of a distal zone at a distal transition 3011. The distal transition 3011 is covered by a distal transition cover 3060 comprising a coil. A cover sleeve 3020 separates the braid 3010 of the proximal zone and the coil 3024 of the distal zone from the distal transition cover 3060. Also as shown, this embodiment may optionally comprise an inner liner 3014, a tie layer 3012, and an axially extending filament 3042 as described elsewhere herein.

Referring to FIG. 20, FIGS. 21A-21B, and FIGS. 22A-22B, catheters may be annealed to advantageously tune the stiffness, flexibility, and/or durometer of one or more portion of the catheters. While the annealing process in connection with FIGS. 20-22B may be discussed in connection with a catheter of one or more various embodiments described herein, it will be understood by one having ordinary skill in the art that one or more steps of the annealing process discussed herein may be used on any suitable catheter in an effort to advantageously tune one or more properties of the catheter.

With reference to the figures, catheters of the various embodiments described herein may comprise a proximal zone comprising a braid that is annealed at a distal transition 3011 to tune the stiffness, flexibility, and/or durometer of the braid. In some embodiments, annealing of the braid may be used to advantageously tune at least one of the stiffness, flexibility, and/or durometer of the braid. Annealing, in some instances, may allow for a smooth transition in catheter stiffness, flexibility, and/or durometer from the proximal zone to the distal zone and/or provide for a catheter with superior kink resistance. In some embodiments, annealing of the braid to tune the stiffness, flexibility, and/or durometer of the braid allows for a smooth transition in catheter stiffness, flexibility, and/or durometer from the proximal zone to the distal zone comprising a coil and provide for a catheter with superior kink resistance.

A catheter with a proximal zone comprising a braid may be annealed by any suitable heating process. In some embodiments, the heating process may include an induction heating process. The induction heating process may be performed by placing at least a portion of the braid over a mandrel. Some examples of a mandrel may include any one of a ferritic stainless steel mandrel, a martensitic stainless steel mandrel, and a duplex stainless steel mandrel. The induction heating process, in some instance, may include placing the braid and mandrel in a coil of an induction heater (e.g., an RDO induction heater). Induction heat generated in the mandrel may be transferred into the braid. In some instance, transfer of induction heat into the braid may perform the annealing.

The induction heating process may advantageously permit control of various parameters, such as induction power and time. Control of one or more of the parameters may, in some instances, may permit variation in the amount of heat transferred from the mandrel to the braid and may further permit variation in the amount of annealing performed.

Figures 21A, 21B:
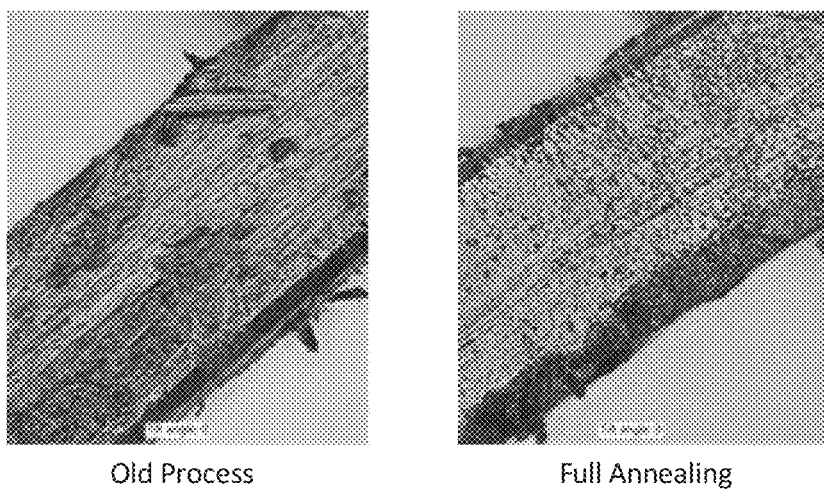
FIGS. 21A-21B show images of braid microstructure of some embodiments according to different annealing processes.

In some embodiments, the amount of braid annealing may be assessed by a visible parameter change in the wires comprising the braid. A visible parameter change may include at least one of a change in color, size, shape, or other physical property. For example, wires comprising the braid being annealed may change in color during the annealing process. FIGS. 21A and 21B illustrate an exemplary embodiment where the braid being annealed changes from silver, to blue, and then to yellow with increased annealing. In some situations, excessive annealing may cause the surface of the braid to oxidize and/or to potentially adhere to the mandrel that is being used to heat it. The ability to visually identify a parameter change in the anneal process may advantageously facilitate control of the annealing process in an effort to avoid excessive annealing.

Figure 20:
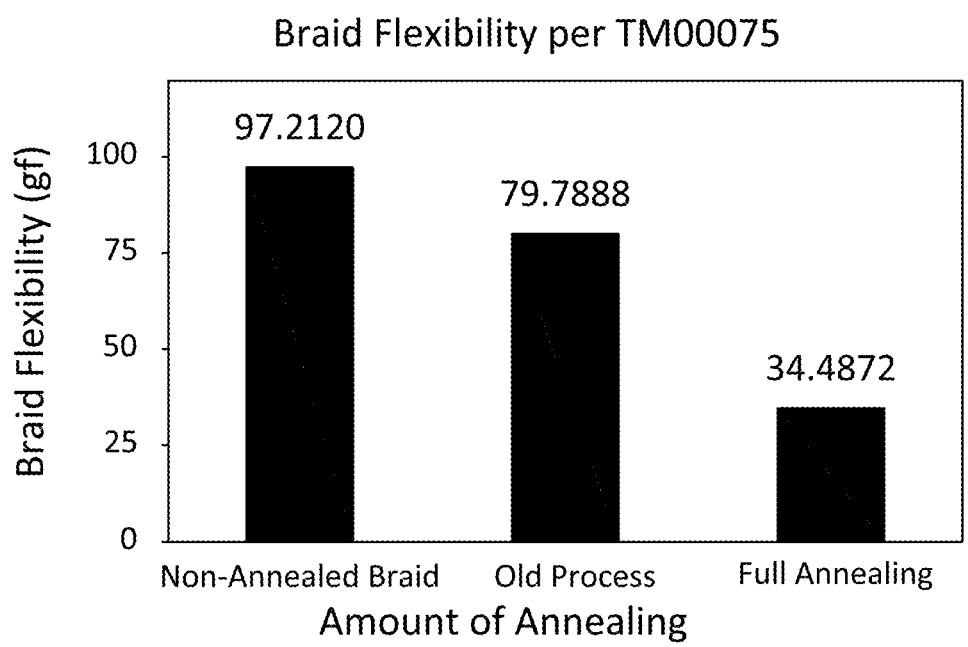
FIG. 20 shows flexibility of braids of some embodiments according to different annealing processes.

Annealing a braid as described herein may advantageously produce a braid with increased flexibility, decreased stiffness, and decreased durometer when compared to previous annealing processes. For example, a prior annealing process may have created a stress-relieved braid such that upon cutting the braid it would not fray. As shown in FIG. 21, the flexibility of braids according to braids of example catheters that underwent different annealing processes (i.e., a non-annealed braid (left bar), a braid annealed according to the prior process (middle bar), and a braid annealed according to a new process that created a fully annealed braid (right bar)) was tested using an Instron (e.g., TM00075) cantilever bending test. As seen in FIG. 20, increased annealing led to less grams-force (gf) being required to be applied to a braid to achieve the same amount of bending (as shown: about 97 gf required for a non-annealed braid, about 80 gf required for a braid annealed according to the old process, and about 34 gf required for a braid annealed according to the new process). In terms of percentages, this initial experimentation was found to increase braid flexibility by about 18% for the old annealing process, and by about 65% for the new annealing process. In some instances, an amount of spring back that occurs after a catheter has been crushed may advantageously decrease as a result of increasing annealing.

Referring to FIGS. 21A-21B, micrographs of a section of braids after annealing are shown according to the old annealing process (FIG. 21A) and the fully annealed process (FIG. 21B) as described herein and corresponding to FIG. 20.

Figure 22B:
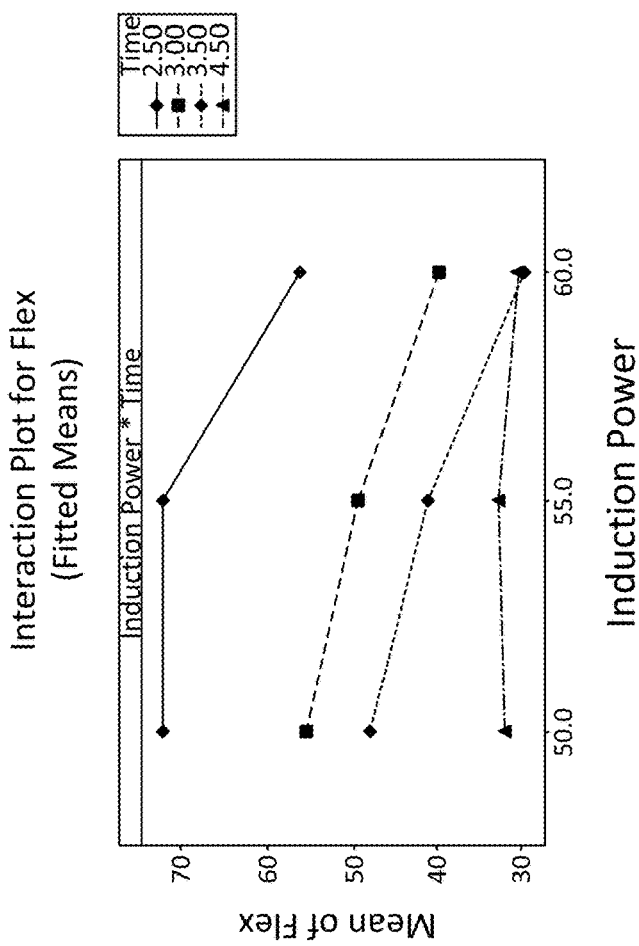
FIG. 22B shows a plot of braid flexibility versus annealing power for various annealing times according to some embodiments.
Figure 22A:
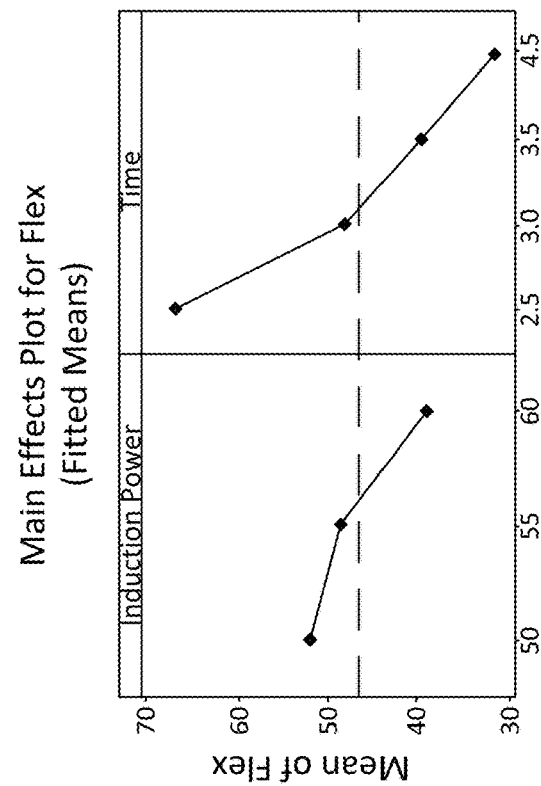
FIG. 22A shows plots of the effects of annealing power and time on the flexibility of braids according to some embodiments.

Referring to FIGS. 22A-22B, plots of the effects of annealing on braids are shown found through experimentation wherein annealing power and time were varied as inputs and braid wire color and braid flexibility were measured as outputs. Through this experimentation, parameters were found that produced braids with a flexibility of about 30 gf as measured per the Instron cantilever bending test described herein. Also found through experimentation, as annealing time increased, oxidation of annealed braids increased.

In some embodiments, annealing power may be increased to mitigate braid oxidation and/or to allows for decreased annealing time. The functional impact of braid annealing may be evaluated by kink testing. For example, braids annealed according to the fully annealed process described herein showed an improvement in kink resistance over samples processed according to the old annealing process. In production, the annealing process may be monitored and controlled by visually inspecting the color of the braid and measuring the amount of braid springback after crushing.

Referring to FIG. 23, FIGS. 24A-24B, and FIG. 25, in some embodiments, catheters as described herein may comprise a distal transition 3011 comprising a distal transition connector 3080. In some embodiments, the distal transition connector 3080 may comprise a connector, a stepped connector, a marker band, a stepped marker band, a stent, or a stepped stent. In some embodiments, the distal transition connector 3080 may comprise a weld, a braze, a solder, or an epoxy. In some embodiments, a weld, a braze, a solder, or an epoxy may be circumferential between a proximal zone and a distal zone of a catheter as described herein. In some embodiments, a weld, a braze, a solder, or an epoxy may be applied irregularly spaced or regularly spaced around a circumference between a proximal zone and a distal zone (e.g., spaced tack welds) of a catheter as described herein. In some embodiments, the distal transition connector 3080 may comprise a distal facing surface that matches at least a portion of a proximal facing surface of a distal zone. In some embodiments, a braid of a proximal zone of a catheter as described herein may comprise a step that matches at least a portion of a proximal facing surface of a coil of a distal zone. In some embodiments, a distal transition connector 3080 may comprise a proximal facing surface that is planar and a distal facing surface comprising a step. In some embodiments, a distal transition connector 3080 may comprise a proximal facing surface that is planar and a distal facing surface comprising a step created by removing a pitch from the distal facing surface. In some embodiments, a distal transition connector 3080 may comprise a distal facing surface that mirrors a proximal facing surface of a distal zone of a catheter as described herein so that a uniform or near uniform gap is created when the distal facing surface of the distal transition connector 3080 abuts the proximal facing surface of the distal zone. In some embodiments, a distal transition connector 3080 may comprise a distal facing surface that mirrors a proximal facing surface of a coil of a distal zone of a catheter as described herein so that a uniform or near uniform gap is created when the distal facing surface of the distal transition connector 3080 abuts the proximal facing surface of the coil of the distal zone. In some embodiments, a distal transition connector 3080 may comprise a distal facing surface with at least a portion of the surface that mirrors at least a portion of a proximal facing surface of a distal zone of a catheter as described herein so that a uniform or near uniform gap is created when the at least a portion of the distal facing surface of the distal transition connector 3080 abuts the at least a portion of the proximal facing surface of the distal zone. In some embodiments, a distal transition connector 3080 may comprise a distal facing surface with at least a portion of the surface that mirrors at least a portion of a proximal facing surface of a coil of a distal zone of a catheter as described herein so that a uniform or near uniform gap is created when the at least a portion of the distal facing surface of the distal transition connector 3080 abuts the at least a portion of the proximal facing surface of the coil of the distal zone.

Figure 23:
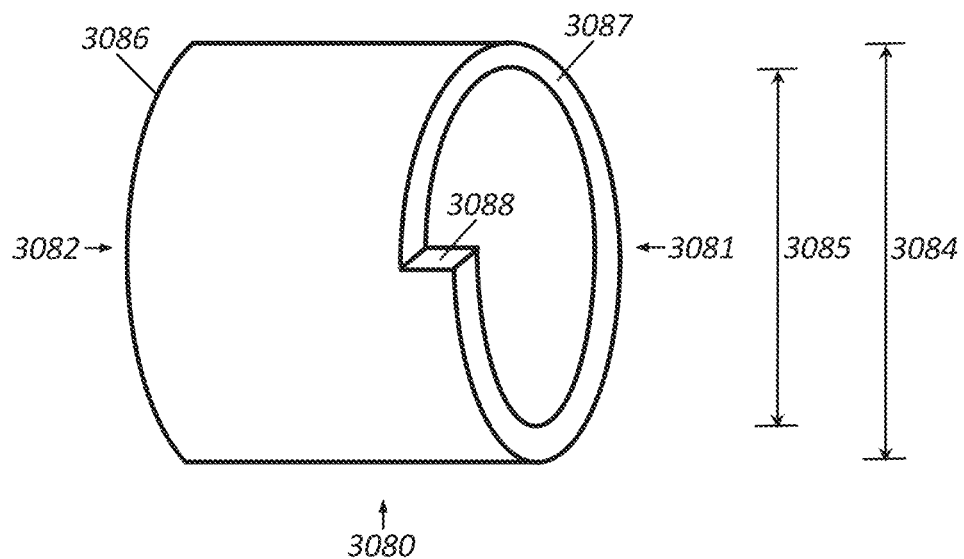
FIG. 23 illustrates a perspective view of a distal transition connector according to some embodiments.

Referring to FIG. 23, shown is a distal transition connector 3080 according to some embodiments. Distal transition connector 3080 may comprise a distal end 3081, a proximal end 3082, an outer diameter 3084, an inner diameter 3085, a proximal surface 3086, and a distal surface 3087. In some embodiments and as shown in FIG. 23, the distal surface 3087 of the distal transition connector 3080 may comprise a step creating a tangential surface 3088. In some embodiments, the step in the distal surface 3087 allows for a proximal end of a coil of a distal zone of a catheter as described herein to form a uniform or near uniform gap between the distal surface 3087 and the proximal end of the coil of the distal zone when the tangential surface 3088 abuts an end of the coil. In some embodiments, proximal surface 3086 of the distal transition connector 3080 is planar to form a uniform or near uniform gap between the proximal surface 3086 and a distal end of a braid of a proximal zone of a catheter as described herein. In some embodiments, the inner diameter 3085 of the distal transition connector 3080 creates an interior lumen in fluid communication with an interior lumen of a proximal zone and an interior lumen of a distal zone of a catheter as described herein.

Figure 24A:
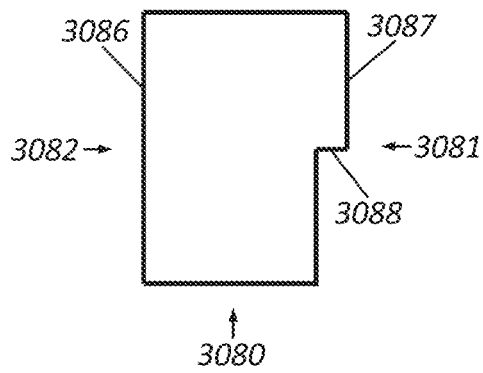
FIGS. 24A-24B illustrate side views of various configurations of a distal transition connector according to some embodiments.
Figure 24B:
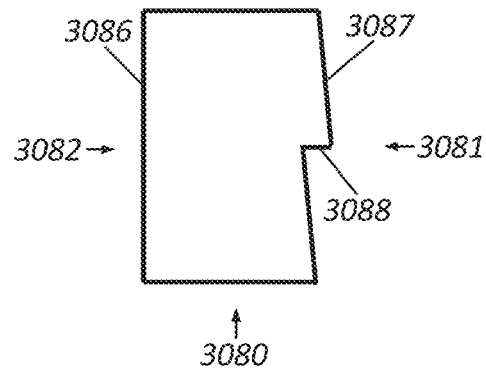

Referring to FIGS. 24A-24B, in some embodiments of a catheter as described herein, a distal transition connector 3080 may comprise a proximal end 3082 with a profile that is about perpendicular in angle to a side wall of the distal transition connector and a distal end 3081 with a profile comprised of a step cut out of the distal end 3081 to create a tangential surface 3088 in the distal end. In some embodiments of a catheter as described herein, a distal transition connector 3080 may comprise a proximal end 3082 with a profile that is about perpendicular in angle to a side wall of the distal transition connector and a distal end 3081 with a profile comprised of a step cut out of the distal end 3081 to create a near tangential surface 3088 in the distal end (e.g., the surface 3088 is at an angle relative to the surface 3087 of about 85 degrees, about 86 degrees, about 87 degrees, about 88 degrees, about 89 degrees, about 90 degrees, about 91 degrees, about 92 degrees, about 93 degrees, about 94 degrees, about 95 degrees, at least about 80 degrees, at most about 95 degrees, between about 85 degrees and about 95 degrees, between about 88 degrees and 91 degrees, between about 89 degrees and 90 degrees). In some embodiments, the step cut out of distal end 3081 of the distal transition connector 3080 comprises an about 5/1000 pitch, an about 4/1000 pitch, an about 3/1000 pitch, an about 6/1000 pitch, an about 7/1000 pitch, at least an about 3/1000 pitch, less than an about 7/1000 pitch, between an about 3/1000 pitch and an about 7/1000 pitch, and between an about 4/1000 pitch and an about 6/1000 pitch removed from the distal end 3081. In some embodiments, a step in the distal end 3081 of distal transition connector 3080 allows a coil 3024 of a distal zone of a catheter as described herein to join flush to the distal surface 3087 of the distal transition connector 3080. In some embodiments, a step in the distal end 3081 of distal transition connector 3080 allows a coil 3024 of a distal zone of a catheter as described herein to join flush to the distal surface 3087 of the distal transition connector 3080 and produce a uniform or near uniform gap between the distal transition connector 3080 and the coil 3024 to facilitate joining the components via a procedure comprising welding, brazing, and/or epoxying. In some embodiments, a step in the distal end 3081 of distal transition connector 3080 allows a coil 3024 of a distal zone of a catheter as described herein to join flush to the distal surface 3087 of the distal transition connector 3080 and produce a uniform or near uniform gap between the distal transition connector 3080 and the coil 3024 to facilitate joining the components via a procedure comprising welding, brazing, and/or epoxying that prevents damage to an underlying liner (e.g., tie layer 3012, inner liner 3014).

Figure 25:
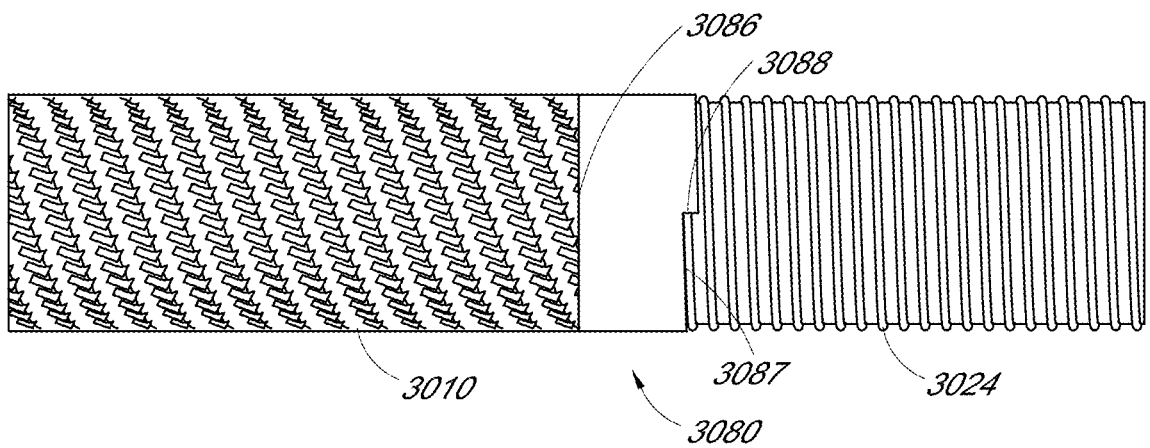
FIG. 25 illustrates a side view of a catheter with a distal transition connector according to some embodiments.

Referring to FIG. 25, illustrated is a side view of a catheter with a distal transition connector according to some embodiments. As shown in FIG. 25, the catheter of this embodiment comprises a proximal zone comprising a braid 3010, a distal transition connector 3080 according to FIG. 23, and a distal zone comprising a helical coil 3024, wherein the proximal surface 3086 of the distal transition connector joins to a distal end of the braid 3010, and wherein the distal surface 3087 and tangential surface 3088 of the distal transition connector join to a proximal end of the helical coil 3024. In this embodiment, the joining of the proximal end of the distal transition connector 3080 to the braid 3010 may comprise a weld, a braze, and/or a solder. In this embodiment, the joining of the distal end of the distal transition connector 3080 to the coil 3024 may comprise a weld, a braze, and/or a solder.

In some embodiments, a distal transition connector 3080 may comprise a material that facilitates welding, brazing, and/or soldering of a stainless steel braid 3010 of a proximal zone to a proximal end 3082 of the distal transition connector 3080 and welding, brazing, and/or soldering of a Nitinol coil 3024 of a distal zone to the distal end 3081 of the distal transition connector 3080. In some embodiments, the distal transition connector comprises Platinum, a Platinum alloy (e.g., 90% Platinum and 10% Iridium), Nickel, a Nickel alloy, Gold, or a Gold alloy (e.g., Au-22Ni-8Pd, Au-20Cu). In some embodiments, a distal transition connector may comprise a polymer, for example PEBAX, polyethylene, polyurethane, nylon, or similar material known to one of skill in the art. In some embodiments, the distal transition connector 3080 may be comprised of a material that allows for a transition in catheter flexibility, durometer, and/or stiffness between a proximal zone and a distal zone of the catheter. In some embodiments, the distal transition connector 3080 may be comprised of a material that allows for a smooth, a curved, a curvilinear, a linear, and/or a stepped transition in catheter flexibility, durometer, and/or stiffness between a proximal zone and a distal zone of the catheter. In some implementations, the distal transition connector is configured to prevent the outer jacket from sinking between or being pinched between the coil and braid interface or transition.

In some embodiments, a distal transition connector 3080 may comprise an inner diameter 3085 and an outer diameter 3084 that are consistent across a length of the distal transition connector. In some embodiments, a distal transition connector 3080 may comprise an inner diameter 3085 and an outer diameter 3084 that are different across a length of the distal transition connector. In some embodiments, a distal transition connector 3080 may comprise an inner diameter 3085 and an outer diameter 3084 that taper across a length of the distal transition connector. In some embodiments, a distal transition connector 3080 may comprise an inner diameter 3085 and an outer diameter 3084 that match at its proximal end 3082 an inner and outer diameter of a braid of a proximal zone of a catheter as described herein. In some embodiments, a distal transition connector 3080 may comprise an inner diameter 3085 and an outer diameter 3084 that match at its distal end 3081 an inner and outer diameter of a coil of a distal zone of a catheter as described herein.

In some embodiments, a distal transition connector 3080 may be rolled over a pin gauge to open its inside diameter 3085 and allow it to be added over an inner liner of a catheter as described herein. In some embodiments, a distal transition connector 3080 may be rolled over a pin gauge to open its inside diameter 3085 and allow it to be added over an inner liner of a catheter as described herein to prevent damage to the inner liner.

In an example, catheters according to the embodiment shown in FIG. 25 with a 5/1000 pitch removed from the distal end 3081 of the distal transition connector 3080 made of a 90% Platinum 10% Iridium alloy, welded at its proximal end 3082 to a stainless steel braid 3010, and welded at its distal end 3081 to a Nitinol helical coil 3024 kinked in the U-bend kink test as described herein over a pin with a 24 mm diameter (this diameter is slightly smaller than the typical inner diameter of the aortic arch), which would allow such a catheter to prolapse inside an aortic arch of a human without kinking.

In some embodiments of the catheters described herein, distal coil 3024 may be comprised of a wire with a variable thickness, cross-sectional diameter, and/or cross-sectional area. In some embodiments, distal coil 3024 may be comprised of a wire with a thickness, cross-sectional diameter, and/or cross-sectional area that decreases in the distal direction. In some embodiments, the distal coil 3024 may be comprised of a wire with a thickness, cross-sectional diameter, and/or cross-sectional area that decreases in the distal direction to provide for a catheter with increasing flexibility in the distal direction. In some embodiments, the distal coil 3024 may be comprised of a wire with a thickness, cross-sectional diameter, and/or cross-sectional area that decreases in the distal direction to provide for a catheter with decreasing durometer in the distal direction. In some embodiments, the distal coil 3024 may be comprised of a wire with a thickness, cross-sectional diameter, and/or cross-sectional area that decreases in the distal direction to provide for a catheter that has a durometer more closely matched to a durometer of a proximal braid 3010 at its proximal end, and with a decreasing durometer in the distal direction to provide for a catheter with increased distal flexibility. In some embodiments, the distal coil 3024 may be comprised of a wire with a thickness, cross-sectional diameter, and/or cross-sectional area that decreases in the distal direction to provide for a catheter that has a durometer more closely matched to a durometer of a distal transition connector 3080 at its proximal end, and with a decreasing durometer in the distal direction to provide for a catheter with increased distal flexibility. In some embodiments, a catheter as described herein may have a durometer that decreases in the distal direction, such that the decrease in durometer is smooth and without significant steps in durometer change. In some embodiments, a catheter as described herein may have a durometer that decreases in the distal direction, such that the decrease in durometer is smooth and without significant steps in durometer change to produce a catheter having superior kink resistance.

Although the present embodiments have been described in terms of certain preferred embodiments, they may be incorporated into other embodiments by persons of skill in the art in view of the disclosure herein. The scope of the embodiments are therefore not intended to be limited by the specific embodiments disclosed herein, but are intended to be defined by the full scope of the following claims.

EXAMPLE EMBODIMENTS

An enhanced flexibility catheter comprising one or more of the following:

an elongate flexible body having a proximal end, a distal end, and a side wall defining a central lumen, wherein the side wall comprises:

a proximal zone comprising a tubular braid and a first helical coil;

a distal zone comprising a second helical coil, and a transition between the distal zone and the proximal zone, wherein the transition comprises a distal end of the tubular braid within 1 cm of a proximal end of the second helical coil, and the first helical coil extends distally beyond the transition.

An enhanced flexibility catheter of any embodiment disclosed herein, wherein distal end of the tubular braid is within 5 mm of the proximal end of the second helical coil.

An enhanced flexibility catheter of any embodiment disclosed herein, wherein the first helical coil is formed from a wire having a first diameter, and the second helical coil is formed from a wire having a second, larger diameter.

An enhanced flexibility catheter of any embodiment disclosed herein, wherein the first helical coil comprises stainless steel.

An enhanced flexibility catheter of any embodiment disclosed herein, wherein the second helical coil comprises Nitinol.

An enhanced flexibility catheter of any embodiment disclosed herein, wherein a distal section of the braid has been heat annealed An enhanced flexibility catheter of any embodiment disclosed herein, wherein the first and second helical coils are intertwined over a length of at least about 5 mm.

An enhanced flexibility catheter of any embodiment disclosed herein, wherein the side wall further comprises a tubular inner liner and a tie layer separated from the lumen by the inner liner, wherein the second helical coil of the distal zone is adjacent the tie layer and the braid of the proximal zone is adjacent the tie layer.

An enhanced flexibility catheter of any embodiment disclosed herein, wherein the elongate flexible body further comprises an outer jacket formed from a plurality of axially adjacent tubular segments wherein a proximal one of the tubular segments has a durometer of at least about 60 D and a distal one of the tubular segments has a durometer of no more than about 35 D.

An enhanced flexibility catheter of any embodiment disclosed herein, wherein the elongate flexible body further comprises an axially extending filament within the side wall.

An enhanced flexibility catheter of any embodiment disclosed herein, further comprising a tubular support having a proximal end surrounding a distal portion of the braid and a distal end surrounding a proximal portion of the second coil.

An enhanced flexibility catheter of any embodiment disclosed herein, wherein the tubular support comprises a slotted metal tube.

An enhanced flexibility catheter comprising one or more of the following:
an elongate flexible body having a proximal end, a distal end, and a side wall defining a central lumen,
wherein the side wall comprises:
a proximal tubular braid having a distal end adjacent a proximal end of a helical coil to form a junction,
a tubular metal support spanning the junction; and
an outer jacket surrounding the tubular support.

An enhanced flexibility catheter of any embodiment disclosed herein, further comprising an axial filament extending distally from beneath the tubular support.

An enhanced flexibility catheter of any embodiment disclosed herein, wherein the side wall further comprises a tubular inner liner and a tie layer separated from the lumen by the inner liner, wherein the helical coil of the distal zone surrounds the tie layer and the braid of the proximal zone surrounds the tie layer.

An enhanced flexibility catheter of any embodiment disclosed herein, wherein the elongate flexible body further comprises an outer jacket formed from a plurality of axially adjacent tubular segments extending coaxially about the helical coil, wherein a proximal one of the tubular segments has a durometer of at least about 60 D and a distal one of the tubular segments has a durometer of no more than about 35 D.

A method of making an enhanced flexibility catheter, the method comprising one or more of the following:
forming a catheter comprising a braid in a proximal zone of the catheter;
placing at least a portion of the braid of the catheter over a mandrel;
annealing a distal section of the braid comprising induction heating the braid and mandrel in a coil; and
visibly monitoring a parameter change of the braid.

A method of making an enhanced flexibility catheter as disclosed in any embodiment herein. wherein induction heating the braid comprises placing the braid and mandrel within an ERDO induction heater.

A method of making an enhanced flexibility catheter as disclosed in any embodiment herein. wherein the parameter change comprises a color change of the braid.

A method of making an enhanced flexibility catheter as disclosed in any embodiment herein, wherein the distal section has an axial length of no more than about 2 cm.

An enhanced flexibility catheter comprising one or more of the following:
an elongate flexible tubular body, having a proximal end, a distal end, a longitudinal axis and a side wall defining a central lumen;
the elongate flexible tubular body comprising an outer jacket formed from a plurality of axially adjacent tubular segments;
wherein a distal end face of a first proximal tubular segment and a proximal end face of an adjacent distal tubular segment are inclined at a non normal angle with respect to the longitudinal axis, and joined together to form an inclined junction between the first proximal tubular segment and the adjacent first distal tubular segment.

An enhanced flexibility catheter as disclosed in any embodiment herein, wherein a midpoint of the first inclined junction is within the range of from about 40-80 mm from the distal end.

An enhanced flexibility catheter as disclosed in any embodiment herein, wherein the midpoint of the first inclined junction is within the range of from about 55-65 mm from the distal end.

An enhanced flexibility catheter as disclosed in any embodiment herein, further comprising a second inclined junction having a midpoint within the range of from about 70 mm to about 110 mm from the distal end.

An enhanced flexibility catheter as disclosed in any embodiment herein, further comprising a second inclined junction having a midpoint within the range of from about 80 mm to about 100 mm.

An enhanced flexibility catheter as disclosed in any embodiment herein, wherein the first inclined junction is inclined by an angle within the range of from about 10 degrees to about 20 degrees from the longitudinal axis.

An enhanced flexibility catheter as disclosed in any embodiment herein, wherein the second inclined junction is inclined by an angle within the range of from about 20 degrees to about 30 degrees from the longitudinal axis.

An enhanced flexibility catheter as disclosed in any embodiment herein, wherein the first proximal tubular segment has a higher durometer than the first distal tubular segment.

An enhanced flexibility catheter as disclosed in any embodiment herein, wherein the first inclined junction and the second inclined junction are formed at the axial ends of the first proximal tubular segment.

An enhanced flexibility catheter as disclosed in any embodiment herein, wherein the first proximal tubular segment has an axial length within the range of from about 10 mm to about 50 mm.

An enhanced flexibility catheter as disclosed in any embodiment herein, wherein the first proximal tubular segment has an axial length within the range of from about 20 mm to about 40 mm.

An enhanced flexibility catheter as disclosed in any embodiment herein, further comprising an axially extending filament within the side wall, extending at least about the most distal 10 cm of the length of the catheter.

An enhanced flexibility catheter as disclosed in any embodiment herein, further comprising a tubular radiopaque marker in the side wall.

An enhanced flexibility catheter as disclosed in any embodiment herein, wherein the filament wraps around the marker.

An enhanced flexibility catheter as disclosed in any embodiment herein, wherein the filament comprises multiple fibers.

An enhanced flexibility catheter as disclosed in any embodiment herein, wherein the side wall further comprises an inner liner and a spring coil, and the filament extends axially in between the coil and the inner liner.

An enhanced flexibility catheter as disclosed in any embodiment herein, wherein the outer jacket is formed from at least five discrete tubular segments.

An enhanced flexibility catheter as disclosed in any embodiment herein, wherein the outer jacket is formed from at least nine discrete tubular segments.

An enhanced flexibility catheter as disclosed in any embodiment herein, wherein the difference in durometer between a proximal one of the tubular segments and a distal one of the tubular segments is at least about 20 D.

An enhanced flexibility catheter as disclosed in any embodiment herein, wherein the difference in durometer between a proximal one of the tubular segments and a distal one of the tubular segments is at least about 30 D.

An enhanced flexibility catheter as disclosed in any embodiment herein, wherein the catheter can withstand at least about 3.5 pounds tension before failure.

An enhanced flexibility catheter as disclosed in any embodiment herein, wherein the catheter can withstand at least about 5 pounds tension before failure.

An enhanced flexibility catheter as disclosed in any embodiment herein, wherein an axial length of the marker band on a leading edge side of the tubular body is at least about 20% longer than an axial length of the marker band on a trailing edge side of the tubular body.

An enhanced flexibility catheter as disclosed in any embodiment herein, wherein the axial length of the marker band on a leading edge side of the tubular body is within the range of from about 1 mm to about 5 mm.

What is claimed is:

1. An enhanced flexibility catheter, comprising:
   an elongate flexible tubular body comprising:
      a proximal end,
      a distal end,
      a longitudinal axis,
      a side wall defining a central lumen, and
      an outer jacket being formed from a plurality of axially adjacent tubular segments;
   wherein a distal end face of a first tubular segment of the plurality of axially adjacent tubular segments and a proximal end face of a second tubular segment of the plurality of axially adjacent tubular segments are positioned adjacent to each other and form an inclined junction between the first tubular segment and the second tubular segment,
   wherein the inclined junction extends along an entire circumference of at least one of the distal end face of the first tubular segment or the proximal end face of the second tubular segment, and
   wherein the inclined junction entirely resides on a plane inclined at a non-normal angle with respect to the longitudinal axis of the elongate flexible tubular body.

2. An enhanced flexibility catheter as in claim 1, wherein a midpoint of the inclined junction is within a range of from about 40 mm to about 80 mm from the distal end.

3. An enhanced flexibility catheter as in claim 2, wherein the midpoint of the inclined junction is within a range of from about 55 mm to about 65 mm from the distal end.

4. An enhanced flexibility catheter as in claim 2, further comprising a second inclined junction having a midpoint within a range of from about 70 mm to about 110 mm from the distal end.

5. An enhanced flexibility catheter as in claim 4, wherein the midpoint of the second inclined junction is within a range of from-about 80 mm to about 100 mm from the distal end.

6. An enhanced flexibility catheter as in claim 4, wherein the inclined junction is inclined by an angle within a range of from about 10 degrees to about 20 degrees relative to the longitudinal axis.

7. An enhanced flexibility catheter as in claim 4, wherein the second inclined junction is inclined by an angle within a range of from about 20 degrees to about 30 degrees from the longitudinal axis.

8. An enhanced flexibility catheter as in claim 1, wherein the first tubular segment has a higher durometer than the second tubular segment.

9. An enhanced flexibility catheter as in claim 4, wherein the inclined junction is formed at the distal end of the first tubular segment, and wherein the second inclined junction is formed at the proximal end of the first tubular segment.

10. An enhanced flexibility catheter as in claim 9, wherein the first tubular segment has an axial length within a range of from about 10 mm to about 50 mm.

11. An enhanced flexibility catheter as in claim 10, wherein the axial length of the first tubular segment is within a range of from about 20 mm to about 40 mm.

12. An enhanced flexibility catheter as in claim 1, further comprising an axially extending filament within the side wall, the axially extending filament extending at least about a most distal 10 cm of a length of the elongate flexible tubular body.

13. An enhanced flexibility catheter as in claim 12, further comprising a tubular radiopaque marker in the side wall.

14. An enhanced flexibility catheter as in claim 12, wherein the filament comprises multiple fibers.

15. An enhanced flexibility catheter as in claim 12, wherein the side wall further comprises an inner liner and a spring coil, and the filament extends axially in between the spring coil and the inner liner.

16. An enhanced flexibility catheter as in claim 1, wherein the outer jacket is formed from at least five discrete tubular segments.

17. An enhanced flexibility catheter as in claim 16, wherein the outer jacket is formed from at least nine discrete tubular segments.

18. An enhanced flexibility catheter as in claim 16, wherein a difference in durometer between a proximal tubular segment of the plurality of axially adjacent tubular segments and a distal tubular segment of the plurality of axially adjacent tubular segments is at least about 20D.

19. An enhanced flexibility catheter as in claim 18, wherein the difference in durometer between the proximal tubular segment and the distal tubular segment is at least about 30D.

20. An enhanced flexibility catheter as in claim 1, wherein the enhanced flexibility catheter can withstand at least about 3.5 pounds tension before failure.

21. An enhanced flexibility catheter as in claim 20, wherein the enhanced flexibility catheter can withstand at least about 5 pounds tension before failure.

22. An enhanced flexibility catheter as in claim 13, the tubular radiopaque marker comprising a first axial length on a first side of the elongate flexible tubular body and a second axial length on a second side of the elongate flexible tubular body, the first axial length being at least about 20% longer than the second axial length.

23. An enhanced flexibility catheter as in claim 22, wherein the first axial length of the tubular radiopaque marker is within a range of from about 1 mm to about 5 mm.

24. An enhanced flexibility catheter as in claim 1, wherein the inclined junction extends along an entire circumference of the distal end face of the first tubular segment and an entire circumference of the proximal end face of the second tubular segment.

* * * * *